United States Patent [19]

Bradfisch et al.

[11] Patent Number: 5,508,264

[45] Date of Patent: Apr. 16, 1996

[54] PESTICIDAL COMPOSITIONS

[75] Inventors: Gregory A. Bradfisch, San Diego; Mark Thompson, Del Mar; George E. Schwab, La Jolla, all of Calif.

[73] Assignee: Mycogen Corporation, San Diego, Calif.

[21] Appl. No.: 349,867

[22] Filed: Dec. 6, 1994

[51] Int. Cl.$^6$ .......................... A61K 38/16; C07K 14/325
[52] U.S. Cl. ............................................. 514/12; 530/350
[58] Field of Search ................................ 530/350; 514/12

[56] References Cited

U.S. PATENT DOCUMENTS

| | | | |
|---|---|---|---|
| 4,448,885 | 5/1984 | Schnepf et al. | 435/253 |
| 4,467,036 | 8/1984 | Schnepf et al. | 435/317 |
| 4,797,276 | 1/1989 | Hernstadt et al. | 424/84 |
| 4,849,217 | 7/1989 | Soares et al. | 424/93 |
| 4,853,331 | 8/1989 | Hernstadt et al. | 435/252.1 |
| 4,918,006 | 4/1990 | Ellar et al. | 435/69.1 |
| 4,948,734 | 8/1990 | Edwards et al. | 435/252.5 |
| 5,055,294 | 10/1991 | Gilroy | 424/93 |
| 5,128,130 | 7/1992 | Gilroy et al. | 424/93 |
| 5,151,363 | 9/1992 | Payne | 435/252.5 |

OTHER PUBLICATIONS

Gaertner, F. H., L. Kim (1988) "Current Applied Recombinant DNA Projects" TIBTECH 6:S4–S7.

Gaertner, F. H. (1989) "Cellular delivery systems for insecticidal proteins: living and non–living microorganisms" in Controlled Deliver of Crop–Protection Agents, pp. 245–255.

Couch, T. L. (1980) "Mosquito Pathogenicity of *Bacillus thuringiensis* var. *israelensis*" Developments in Industrial Microbiology 22:61–76.

Beegle, C. C. (1978) "Use of Entomogenous Bacteria in Agroecosystems" in Developments in Industrial Microbiology 20:97–104.

Krieg, A. et al. (1983) "*Bacillus thuringiensis* var. *tenebrionis*: ein neuer, gegenuber Larven von Coleopteren Wirksamer Pathotyp" Z. ang. Ent. 96:500–508.

Hofte, H., H. R. Whiteley (1989) "Insecticidal Crystal Proteins of *Bacillus thuringiensis*" Microbiological Reviews 52(2):242–255.

Feitelson, J. S. et al. (1992) "*Bacillus thuringiensis:* Insects and Beyond" Bio/Technology 10:271–275.

Schnepf, H. E., H. R. Whiteley (1981) "Cloning and expression of the *Bacillus thuringiensis* crystal protein gene in *Escherichia coli*" Proc. Natl. Acad. Sci. USA 78(5):2893–2897.

Li, J., J. Carroll, D. J. Ellar (1991) "Crystal structure of insecticidal δ–endotoxin from *Bacillus thuringiensis* at 2.5 Å resolution" Nature 353:815–821.

Arvidson, H. et al. (1989) "Specificity of *Bacillus thuringiensis* for lepidopteran larvae: factors involved in vivo and in the structure of a purified protoxin" Molecular Microbiology 3(11):1533–1543.

Choma, C. T. et al. (1990) "Unusual proteolysis of the protoxin and toxin from *Bacillus thuringiensis*" Eur. J. Biochem. 189:523–527.

Haider, M. Z., et al. (1986) "Specificity of *Bacillus thuringiensis* var. *colmeri* insecticidal δ–endotoxin is determined by differential protolytic processing of the protoxin" Eur. J. Biochem. 156:531–540.

Aronson, A. I. et al. (1991) "The Solubility of Inclusion Proteins from *Bacillus thuringiensis* is Dependent upon Protoxin Composition and is a Factor in Toxicity to Insects" Appl. Environ. Microbiol. 57(4):981–986.

Honee, G. et al. (1991) "The C–terminal domain of the toxic fragment of a *Bacillus thuringiensis* crystal protein determines receptor binding" Molecular Microblology 5(11):2799–2806.

Honee, G. et al. (1990) "A Translation Fusion Product of Two Different Insecticidal Crystal Protein Genes of *Bacillus thuringiensis* Exhibits an Enlarged Insecticidal Spectrum" Appl. Environ. Microbiol. 56(3):823–825.

Moar, W. J. et al. (1986) "Potentiation of *Bacillus thuringiensis* var. *kurstaki* with Thuringiensin on Beet Armyworm (Lepidoptera: Noctuidae)" Journal of Economic Entomology 79(6):1443–1446.

Chilcott, C. N., D. J. Ellar (1988) "Comparative Toxicity of *Bacillus thuringiensis* var. *israelensis* Crystal Proteins in in vivo and in vitro" Journal of General Microbiology 134:2551–2558.

Wu, D., F. N. Chang (1985) "Synergism in Mosquitocidal activity of 26 and 65 kDa proteins from *Bacillus thuringiensis* subsp. *israelensis* crystal" FEBS Letters 190(2):232–236.

Angsuthanasombat, C. et al. (1992) "Comparison of *Bacillus thuringiensis* subsp. *israelensis* CryIVA and CryIVB cloned toxins reveals synergism in vivo" FEMS Microbiology Letters 94:63–68.

*Primary Examiner*—Robert A. Wax
*Assistant Examiner*—Kawai Lau
*Attorney, Agent, or Firm*—Saliwanchik & Saliwanchik

[57] ABSTRACT

Disclosed are compositions and processes for controlling lepidopteran pests. These compositions comprise synergistic combinations of a CryIF chimeric and CryIA(c) chimeric *Bacillus thuringiensis* δ-endotoxin. These compositions have been found to exhibit excellent activity against lepidopteran pests.

17 Claims, 10 Drawing Sheets

Fig. 9A

```
                                                                                              90
Cons   MENNIQNQCV PYNCLNNPEV EILNEERSTG RLPLDISLSL TRFLLSEFVP GVGVAFGLFD LIWGFITPSD WSLFLLQIEQ LIEQRIETLE
                                                                                             180
Cons   RNRAITTLRG LADSYEIYIE ALREWEANPN NAQLREDVRI RFANTDDALI TAINNFTLTS FEIPLLSVYV QAANLHLSLL RDAVSFGQGW
                                                                                             270
Cons   GLDIATVNNH YNRLINLIHR YTKHCLDTYN QGLENLRGTN TRQWARFNQF RRDLTLTVLD IVALFPNYDV RTYPIQTSSQ LTREIYTSSV
                                                                                             360
Cons   IEDSPVSANI PNGFNRAEFG VRPPHLMDFM NSLFVTAETV RSQTVWGGHL VSSRNTAGNR INFPSYGVFN PGGAIWIADE DPRPFYRTLS
                                                                                             450
Cons   DPVFVRGGFG NPHYVLGLRG VAFQQTGTNH TRTFRNSGTI DSLDEIPPQD NSGAPWNDYS HVLNHVTFVR WPGEISGSDS WRAPMFSWTH
                                                                                             540
Cons   RSATPTNTID PERITQIPLV KAHTLQSGTT VVRGPGFTGG DILRRTSGGP FAYTIVNING QLPQRYRARI RYASTTNLRI YVTVAGERIF
        541                                                                                 630
                                                                                 t
                                                                                 i
Alt                                                                              p     l i
Alt                                                                e      a
Cons   AGQFNKTMDT GDPLTFQSFS YATINTAFTF PMSQSSFTVG ADTFSSGNEV YIDRFELIPV TATFEAEYdL ERAQKAVNEL FTSSNQIGLK
                                                                                             720
                   e                                        s
Alt                r                         ng                 kd   p     g g     r          p
Alt    n    Q    t                                                                          s
Cons   TDVTDYHIDI VSNLVECLSD EFCLDEKKEL SEKVKHAKRL SDERNLLQDP NFRGINRQLD RGWRGSTDIT IQGGDDVFKE NYVTLLGTFD
        721                                                                                 810
                                                                       vq
Alt            l                   p                                   fe   s  rKCGE PNRCAPHLEW NPDLDCSCRD
Alt
Cons   ECYPTYLYQK IDESKLKAYT RYQLRGYIED SQDLEIYLIR YNAKHETVNV PGTGSLWPLS APSPIG----  ----------  ----------
```

Fig. 9B

```
                                                       e    i   gra                                  ql              900
Alt         811                           i    d
Cons        GE --KCAHHSHH FSLDIDVGCT DLNEDLGVWV IFKIKTQDGH ARLGNLEFLE EK-PLVGEAL ARVKRAEKKW RDKREKLEWE TNIVYKEAKE q                       t    r q       d                 f    k                              990
Alt         901                                          vg
Cons        SVDALFVNSQ YDRLQADTNI AMIHAADKRV HSIREAYLPE LSVIPGVNAA IFEELEGRIF TAFSLYDARN VIKNGDFNNG LSCWNVKGHV q                                t                 f                             n    g     1080
Alt         991
Cons        DVEEQNNHRS VLVVPEWEAE VSQEVRVCPG RGYILRVTAY KEGYGEGCVT IHEIENNTDE LKFSNCVEEE VYPNNTVTCN DYTATQEEYE a    c    et g    y              v                                            q                        1170
Alt         1081
Cons        GTYTSRNRGY DGAYESNSSV PADYASAYEE KAYTDGRRDN. PCESNRGYGD YTPLPAGYVT KELEYFPETD KVWIEIGETE GTFIVDSVEL Cons        1171
            LLMEE
```

PESTICIDAL COMPOSITIONS

BACKGROUND OF THE INVENTION

The soil microbe *Bacillus thuringiensis* (B.t) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain *B.t.* toxin genes have been isolated and sequenced, and recombinant DNA-based *B.t.* products have been produced and approved for use. In addition, with the use of genetic engineering techniques, new approaches for delivering these *B.t.* endotoxins to agricultural environments are under development, including the use of plants genetically engineered with endotoxin genes for insect resistance and the use of stabilized intact microbial cells as *B.t.* endotoxin delivery vehicles (Gaertner, F. H., L. Kim [1988] TIBTECH 6:S4–S7). Thus, isolated *B.t.* endotoxin genes are becoming commercially valuable.

Until the last ten years, commercial use of *B.t.* pesticides has been largely restricted to a narrow range of lepidopteran (caterpillar) pests. Preparations of the spores and crystals of *B. thuringiensis* subsp. kurstaki have been used for many years as commercial insecticides for lepidopteran pests. For example, *B. thuringiensis* var. kurstaki HD-1 produces a crystal called a δ-endotoxin which is toxic to the larvae of a number of lepidopteran insects.

In recent years, however, investigators have discovered *B.t.* pesticides with specificities for a much broader range of pests. For example, other species of B.t., namely israelensis and tenebrionis (a.k.a. *B.t.* M-7, a.k.a. *B.t.* san diego), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255). See also Couch, T. L. (1980) "Mosquito Pathogenicity of *Bacillus thuringiensis* var. israelensis," *Developments in Industrial Microbiology* 22:61–76; Beegle, C. C., (1978) "Use of Entomogenous Bacteria in Agroecosystems," *Developments in Industrial Microbiology* 20:97–104. Krieg, A., A. M. Huger, G. A. Langenbruch, W. Schnetter (1983) Z. ang. Ent. 96:500–508, describe *Bacillus thuringiensis* var. tenebrionis, which is reportedly active against two beetles in the order Coleoptera. These are the Colorado potato beetle, *Leptinotarsa decemlineata*, and *Agelastica alni*.

Recently, new subspecies of *B.t.* have been identified, and genes responsible for active δ-endotoxin proteins have been isolated (Höfte, H., H. R. Whiteley [1989] *Microbiological Reviews* 52(2):242–255). Höfte and Whiteley classified *B.t.* crystal protein genes into 4 major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported. (Feitelson, J. S., J. Payne, L. Kim [1992] *Bio/Technology* 10:271–275).

The cloning and expression of a *B.t.* crystal protein gene in *Escherichia coli* has been described in the published literature (Schnepf, H. E., H. R. Whiteley [1981] *Proc. Natl. Acad. Sci. USA* 78:2893–2897). U.S. Pat. No. 4,448,885 and U.S. Pat. No. 4,467,036 both disclose the expression of a *B.t.* crystal protein in *E. coli*. Hybrid *B.t.* crystal protein genes have been constructed that exhibit increased toxicity and display an expanded host range to a target pest. See U.S. Pat. Nos. 5,128,130 and 5,055,294. U.S. Pat. Nos. 4,797,276 and 4,853,331 disclose *B. thuringiensis* strain san diego (a.k.a. *B.t.* tenebrionis, a.k.a. M-7) which can be used to control coleopteran pests in various environments. U.S. Pat. No. 4,918,006 discloses *B.t.* toxins having activity against dipterans. U.S. Pat. No. 4,849,217 discloses *B.t.* isolates which have activity against the alfalfa weevil. U.S. Pat. No. 5,151,363 and U.S. Pat. No. 4,948,734 disclose certain isolates of *B.t.* which have activity against nematodes.

As a result of extensive research and investment of resources, other patents have issued for new *B.t.* isolates and new uses of *B.t.* isolates. However, the discovery of new *B.t.* isolates and new uses of known *B.t.* isolates remains an empirical, unpredictable art.

A majority of *Bacillus thuringiensis* δ-endotoxin crystal protein molecules are composed of two functional segments: The protease-resistant core toxin is the first segment and corresponds to about the first half of the protein molecule. The three-dimensional structure of a core segment of a cryIIIA *B.t.* δ-endotoxin is known and it is proposed that all related toxins have that same overall structure (Li, J., J. Carroll, D. J. Ellar [1991] *Nature* 353:815–821). The second half of the molecule is the second segment. For purposes of this application, this second segment will be referred to herein as the "protoxin segment." The protoxin segment is believed to participate in toxin crystal formation (Arvidson, H., P. E. Dunn, S. Strand, A. I. Aronson [1989] *Molecular Microbiology* 3:1533–1534; Choma, C. T., W. K. Surewicz, P. R. Carey, M. Pozsgay, T. Raynor, H. Kaplan [1990] *Eur. J. Biochem.* 189:523–527). The full 130 kDa toxin molecule is rapidly processed to the resistant core segment by protease in the insect gut. The protoxin segment may thus convey a partial insect specificity for the toxin by limiting the accessibility of the core to the insect by reducing the protease processing of the toxin molecule (Haider, M. Z., B. H. Knowles, D. J. Ellar [1986] *Eur. J. Biochem.* 156:531–540) or by reducing toxin solubility (Aronson, A. I., E. S. Han, W. McGaughey, D. Johnson [1991] *Appl. Environ. Microbiol.* 57:981–986).

Chimeric proteins joined within the toxin domains have been reported between CryIC and CryIA(b) (Honee, G., D. Convents, J. Van Rie, S. Jansens, M. Perferoen, B. Visser [1991] *Mol. Microbiol.* 5:2799–2806); however, the activity of these chimeric proteins was either much less, or undetectable, when compared to CryIC on a relevant insect.

Honee et al. (Honee, G., W. Vriezen, B. Visser [1990] *Appl. Environ. Microbiol.* 56:823–825) also reported making a chimeric fusion protein by linking tandem toxin domains of CryIC and CryIA(b). The resulting protein had an increased spectrum of activity equivalent to the combined activities of the individual toxins; however, the activity of the chimeric was not increased toward any one of the target insects.

When toxins or biologically active agents are blended together, the biological activity of the resulting mixture can be affected in several ways. The resultant biological activity can be the sum of the activity of each of the toxins. Biological activity of the mixture may be less than the sum of the activity of each of the agents, or the resultant activity may be greater than the sum of the activity of each of the agents.

A nucleotide β-exotoxin produced by a particular *B.t.* strain was found to act in synergy with the protein δ-endotoxins in *B.t.* var. kurstaki to yield increased activity against the lepidopteran pest *Spodoptera exigua* (Moar, W. J., W. L. A. Osbrink, J. T> Trumble [1986] *J. Econ. Entomol.*

79:1443–1446). Enhanced toxicity to mosquito larvae occurs with the mixture of the 27 kDa and the 65 or 130 kDa proteins from *B.t.* var. *israelensis* (Chilcott, C. N., D. J. Ellar [1988] *J. Gen. Microbiology* 132:2551– 2558; Yu et al., 1987; Wu, D., F. N. Chang [1985] *FEBS* 190(2):232–236). The CryIVA and CryIVB toxins from *B.t.* var. *israelensis* have also been used together (Angsuthanasomat, C., N. Crickmore, D. J. Ellar [1992] *FEMS Microbiol. Lett.* 94:63–68).

BRIEF SUMMARY OF THE INVENTION

The subject invention concerns the discovery of advantageous increased activity against lepidopteran pests achieved by the combination of two *Bacillus thuringiensis* (B.t.) δ-endotoxin proteins. More specifically, a CryIF chimeric toxin combined with a CryIA(c) chimeric toxin act in synergy to yield unexpected enhanced toxicity to lepidopteran pests.

The synergistic effect of the subject invention may be achieved by combining, as in a mixture, isolates that each produce one of the toxin proteins. Recombinant hosts engineered to express both of the toxins of the subject invention can also be used to achieve the synergistic effect. Suitable recombinant hosts include prokaryotes and lower eukaryotes, as well as plants.

Chimeric CryIF genes useful according to the subject invention can be assembled that substitute a heterologous protoxin segment for all or part of the native cryIF protoxin segment. In particular, all or part of the protoxin-encoding region of a cryIA(b) gene can be used in place of all or part of the region which encodes the protoxin for a native cryIF toxin. Similarly, a chimeric gene can be constructed wherein the region encoding all or part of the protoxin of a cryIF toxin is replaced by DNA encoding all or part of the protoxin of a cryIA(c)/cryIA(b) chimeric gene. In a specific embodiment, the cryIA(c)/cryIA(b) chimeric gene is that which has been denoted 436 and which is described in U.S. Pat. No. 5,128,130. This gene can be obtained from the plasmid in *P. fluorescens* MR436.

The chimeric gene can be introduced into a wide variety of microbial or plant hosts. A transformed host expressing the chimeric gene can be used to produce the lepidopteran-active toxins of the subject invention. Transformed hosts can be used to produce the insecticidal toxins or, in the case of a plant cell transformed to produce the toxins, the plant will become resistant to insect attack. The subject invention further pertains to the use of the chimeric toxins, or hosts containing the genes encoding the chimeric toxins, in methods for controlling lepidopteran pests.

Still further, the invention includes combinations of substantially intact treated *B.t.* cells, or recombinant cells expressing the genes and producing the toxins of the invention. The cells can be treated to prolong the pesticidal activity when the substantially intact cells are applied to the environment of the target pest. Such treatment can be by chemical or physical means, or a combination of chemical and physical means, so long as the technique does not deleteriously affect the synergistic properties of the pesticides, nor diminish the cellular capability in protecting the pesticides. The treated cell acts as a protective coating for the pesticidal toxins. The toxins become available to act as such upon ingestion by a target pest.

BRIEF DESCRIPTION OF THE DRAWINGS

FIG. 9—A CryIF/CryIA(b) chimeric protein sequence and residue-by-residue substitutions. The 'Cons' line shows a CryIF/CryIA(b) chimeric sequence. The 'Alt' lines show residue-by-residue substitutions found in the 436 protein, CryIA(b) variant proteins and CryIF protoxins.

BRIEF DESCRIPTION OF THE SEQUENCES

Figure 1:
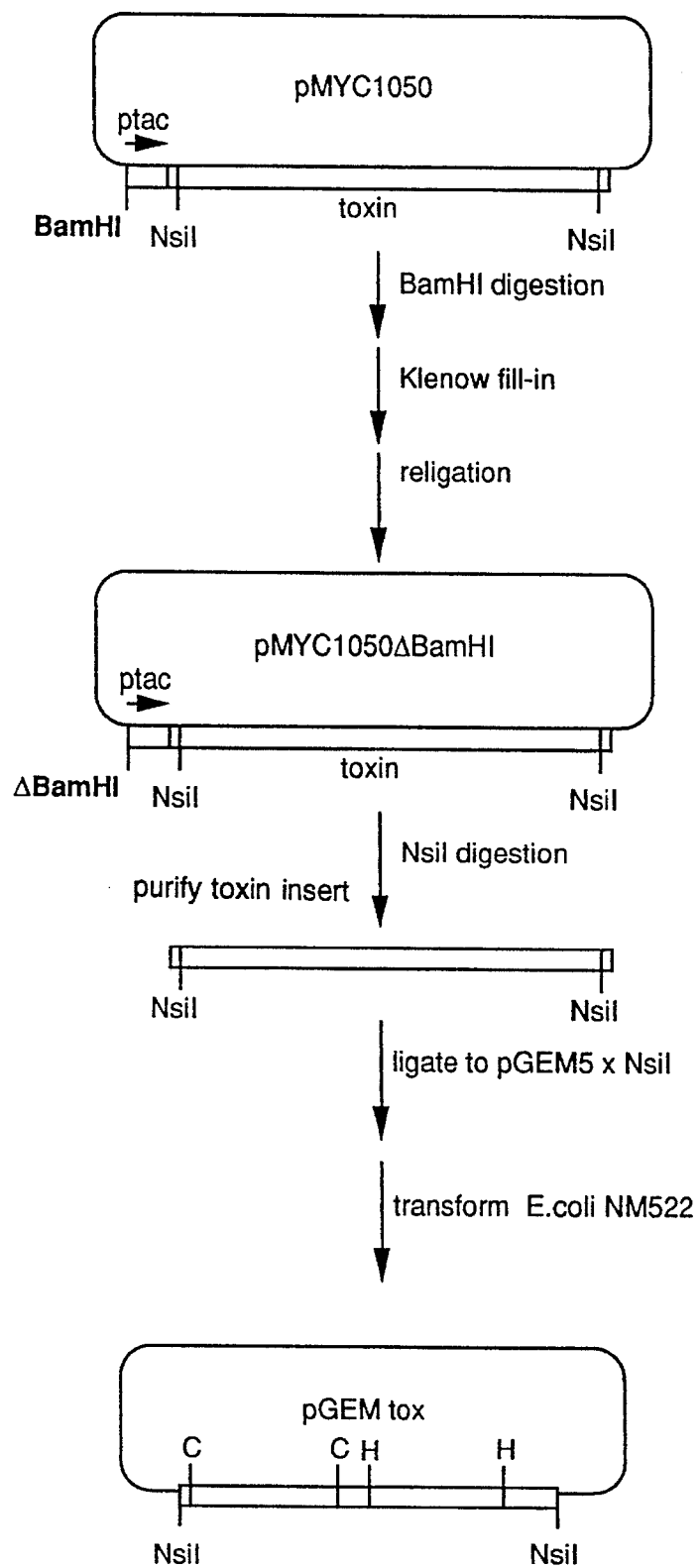
FIG. 1—The BamHI site is removed from pMYC1050 by a fill-in reaction with Klenow polymerase to give plasmid pMYC1050ΔBamHI. To facilitate cloning, an NsiI DNA fragment that contains most of the toxin open reading frame is cloned into pGEM5. The resulting plasmid is called pGEMtox. C=ClaI, H=HindIII.

SEQ ID NO. 1 is oligonucleotide primer "A"

SEQ ID NO. 2 is oligonucleotide primer "B"

SEQ ID NO. 3 is oligonucleotide primer "C"

SEQ ID NO. 4 is oligonucleotide primer "D"

SEQ ID NO. 5 is oligonucleotide primer "E"

SEQ ID NO. 6 is oligonucleotide primer "F"

SEQ ID NO. 7 is oligonucleotide primer "G"

SEQ ID NO. 8 is oligonucleotide primer "L"

SEQ ID NO. 9 is oligonucleotide primer "N"

SEQ ID NO. 10 is oligonucleotide primer "O"

SEQ ID NO. 11 is oligonucleotide primer "H"

SEQ ID NO. 12 is oligonucleotide primer "I"

SEQ ID NO. 13 is oligonucleotide primer "J"

SEQ ID NO. 14 is oligonucleotide primer "K"

SEQ ID NO. 15 is oligonucleotide primer "P"

SEQ ID NO. 16 is oligonucleotide primer "Q"

SEQ ID NO. 17 is oligonucleotide primer "M"

SEQ ID NO. 18 shows the toxin-encoding DNA sequence of pMYC2224.

SEQ ID NO. 19 shows the predicted amino acid sequence of the toxin encoded by pMYC2224.

SEQ ID NO. 20 shows the toxin-encoding DNA sequence of pMYC2239.

SEQ ID NO. 21 shows the predicted amino acid sequence of the toxin encoded by pMYC2239.

SEQ ID NO. 22 shows the toxin-encoding DNA sequence of pMYC2244, which encodes a cryIF/cryIA(b) chimeric toxin.

SEQ ID NO. 23 shows the predicted amino acid sequence of the cryIF/cryIA(b) chimeric toxin encoded by pMYC2244.

SEQ ID NO. 24 shows the toxin-encoding DNA sequence of pMYC2243.

SEQ ID NO. 25 shows the predicted amino acid sequence of the toxin encoded by pMYC2243.

SEQ ID NO. 26 shows the toxin-encoding DNA sequence of pMYC2523, which encodes a cryIF/cryIA(b) chimeric toxin with codon rework.

SEQ ID NO. 27 shows the predicted amino acid sequence of the toxin encoded by pMYC2523.

SEQ ID NO. 28 shows the toxin-encoding DNA sequence of pMYC2254, which encodes a cryIF/436 chimeric toxin.

SEQ ID NO. 29 shows the predicted amino acid sequence of the toxin encoded by pMYC2254.

SEQ ID NO. 30 is a characteristic sequence of cryI toxins. This sequence ends at residue 601 of SEQ ID NO. 23.

SEQ ID NO. 31 is the eight amino acids preceding amino acid 1043 in SEQ ID NO. 23.

SEQ ID NO. 32 shows the amino acid sequence of a native cryIF/cryIA(b) toxin.

SEQ ID NO. 33 shows the amino acid sequence of a native cryIA(b) toxin.

SEQ ID NO. 34 shows the amino acid sequence of a cryIA(c)/cryIA(b) toxin.

DETAILED DISCLOSURE OF THE INVENTION

The subject invention concerns the unexpected enhanced pesticidal activity resulting from the combination of a CryIF chimeric toxin and a CryIA(c) chimeric toxin. The combination surprisingly has increased activity against lepidopteran pests. Preparations of combinations of isolates that produce the two chimeric toxins can be used to practice the subject invention. *Pseudomonas fluorescens* cells transformed with *B.t.* genes can serve as one source of the toxins of the subject invention. For example, a lactose-inducible *P. fluorescens* strain comprising a gene encoding a CryIF/CryIA(b) toxin, and *P. fluorescens* MR436, which comprises a gene encoding a CryIA(c)/CryIA(b) chimeric toxin, can be used to practice the subject invention. These two Pseudomonas strains can be combined in a physical blend that exhibits advantageous enhanced pesticidal activity. Genes encoding the toxins of the invention can be used to transform suitable hosts so that a single host will produce the two toxins providing the advantageous effect.

Bacteria harboring plasmids useful according to the subject invention are the following:

| Culture | Repository No. | U.S. Pat. No. |
|---|---|---|
| *P. fluorescens* (pM3,130–7) | NRRL B-18332 | 5,055,294 |
| *P. fluorescens* MR436 (pM2,16–11, aka pMYC436) | NRRL B-18292 | 5,128,130 |
| *E. coli* NM522 (pMYC1603) | NRRL B-18517 | 5,188,960 |

It should be understood that the availability of a deposit does not constitute a license to practice the subject invention in derogation of patent rights granted by governmental action.

In accordance with the subject invention, it has been discovered that products comprising the two chimeric toxins have been discovered to require a lower total protein content for product application, thus providing the user greater economy. Insects which are less susceptible to the action of a single toxin will be more greatly affected by the combination of toxins of the subject invention, rendering a product containing the two toxins more efficacious than products containing a single toxin. Additionally, pests are less likely to develop a rapid resistance to a product containing the two toxins, than to products containing a single toxin.

Combinations of the toxins described in the invention can be used to control lepidopteran pests. Adult lepidopterans, i.e., butterflies and moths, primarily feed on flower nectar and are a significant effector of pollination. The larvae, i.e., caterpillars, nearly all feed on plants, and many are serious pests. Caterpillars feed on or inside foliage or on the roots or stem of a plant, depriving the plant of nutrients and often destroying the plant's physical support structure. Additionally, caterpillars feed on fruit, fabrics, and stored grains and flours, ruining these products for sale or severely diminishing their value. As used herein, reference to lepidopteran pests refers to various life stages of the pest, including larval stages.

The chimeric toxins of the subject invention comprise a full core N-terminal toxin portion of a *B.t.* toxin and, at some point past the end of the toxin portion, the protein has a transition to a heterologous protoxin sequence. The N-terminal toxin portion of a *B.t.* toxin is referered to herein as the "core" toxin. The transition to the heterologous protoxin segment can occur at approximately the toxin/protoxin junction or, in the alternative, a portion of the native protoxin (extending past the toxin portion) can be retained with the transition to the heterologous protoxin occurring downstream. As an example, one chimeric toxin of the subject invention has the full toxin portion of cryIF (amino acids 1–601) and a heterologous protoxin (amino acids 602 to the C-terminus). In a preferred embodiment, the heterologous portion of the protoxin is derived from a cryIA(b) or 436 toxin.

A person skilled in this art will appreciate that *B.t.* toxins, even within a certain class such as cryIF, will vary to some extent in length and the precise location of the transition from toxin portion to protoxin portion. Typically, the cryIA(b) and cryIF toxins are about 1150 to about 1200 amino acids in length. The transition from toxin portion to protoxin portion will typically occur at between about 50% to about 60% of the full length toxin. The chimeric toxin of the subject invention will include the full expanse of this core N-terminal toxin portion. Thus, the chimeric toxin will comprise at least about 50% of the full length cryIF *B.t.* toxin. This will typically be at least about 590 amino acids. With regard to the protoxin portion, the full expanse of the cryIA(b) protoxin portion extends from the end of the toxin portion to the C-terminus of the molecule. It is the last about 100 to 150 amino acids of this portion which are most critical to include in the chimeric toxin of the subject invention. In a chimeric toxin specifically exemplified herein, at least amino acids 1043 (of SEQ ID NO. 23) to the C-terminus of the cryIA(b) molecule are utilized. Amino acid 1043 in SEQ ID NO. 23 is preceded by the sequence Tyr Pro Asn Ash Thr Val Thr Cys (SEQ ID NO. 31). This amino acid sequence marks the location in the protoxin segment of the molecule beyond which heterologous amino acids will always occur in the chimeric toxin. In another example, the peptide shown as SEQ ID NO. 31 occurs at amino acids 1061 to 1068. In this case, amino acids 1069 to the C-terminus are preferably heterologous (SEQ ID NO. 29). The peptide shown in SEQ ID NO. 31 can be found at positions 1061 to 1068 in FIG. 9. Thus, it is at least the last approximately 5 to 10% of the overall *B.t.* protein which should comprise heterologous DNA (compared to the cryIF core N-terminal toxin portion) in the chimeric toxin of the subject invention. In the specific examples contained herein, heterologous protoxin sequences occur from amino acid 640 to the C-terminus.

Thus, a preferred embodiment of the subject invention is a chimeric *B.t.* toxin of about 1150 to about 1200 amino acids in length, wherein the chimeric toxin comprises a cryIF core N-terminal toxin portion of at least about 50 to 60% of a full cryIF molecule, but no more than about 90 to 95% of the full molecule. The chimeric toxin further comprises a cryIA(b) or a 436 protoxin C-terminal portion which comprises at least about 5 to 10% of the cryIA(b) or 436 molecule. The transition from cryIF to cryIA(b) or 436 sequence thus occurs within the protoxin segment (or at the junction of the toxin and protoxin segments) between about 50% and about 95% of the way through the molecule. In the specific examples provided herein, the transitions from the cryIF sequence to the heterologous protoxin sequences occur prior to the end of the peptide sequence shown in SEQ ID NO. 31.

A specific embodiment of the subject invention is the chimeric toxin shown in FIG. 9. Other constructs may be made and used by those skilled in this art having the benefit of the teachings provided herein. The core toxin segment of cryI proteins characteristically ends with the sequence: Val/Leu Tyr/Ile Ile Asp Arg/Lys Ile/Phe Glu Ile/Phe/Leu Ile/Leu/Val Pro/Leu Ala/Val Glu/Thr/Asp (SEQ ID NO. 30), which ends at residue 601 of SEQ ID NO. 23. Additionally, the protoxin segments of the cryI toxins (which follow residue 601) bear more sequence similarity than the toxin segments. Because of this sequence similarity, the transition point in the protoxin segment for making a chimeric protein between the cryIF sequence and the cryIA(b) or 436 sequence can be readily determined by one skilled in the art. From studies of data regarding the partial proteolysis of CryI genes, the heterogeneity and least-conserved amino acid regions are found after the conserved cryI protoxin sequence, positions 1061–1068 of FIG. 9.

Therefore a chimeric toxin of the subject invention can comprise the full cryIF toxin and a portion of the cryIF protoxin, transitioning to the corresponding cryIA(b) or 436 sequence at any position between the end of the toxin segment (as defined above) and the end of the peptide sequence shown in SEQ ID NO. 31. Preferably, the amino acid sequence of the C-terminus of the chimeric toxin comprises a cryIA(b) sequence or a sequence from the 436 gene or an equivalent of one of these sequences.

CryIF toxins, and genes which encode these toxins, are well known in the art. CryIF genes and toxins have been described in, for example, Chambers et al. (1991) *J. Bacteriol.* 173:3966. CryIA(b) genes and toxins have been described in, for example, Höfte et al. (1986) *Eur. J. Biochem.* 161:273; Geiser et al. (1986) *Gene* 48:109; and Haider et al. (1988) *Nucleic Acids Res.* 16:10927. The skilled artisan having the benefit of the teachings contained herein could readily identify and use DNA which encodes the toxin N-terminal portion of a cryIF molecule and the C-terminal protoxin portion of the cryIA(b) toxins.

FIG. 9 provides examples of amino acid substitutions which can be used in the toxins of the subject invention. It is also well known in the art that various mutations can be made in a toxin sequence without changing the activity of a toxin. Furthermore, due to the degeneracy of the genetic code, a variety of DNA sequences can be used to encode a particular toxin. These alternative DNA and amino acid sequences can be used according to the subject invention by a person skilled in this art.

The protoxin substitution techniques of the subject invention can be used with other classes of *B.t.* endotoxins to enhance expression of the toxin. The technique would be most applicable to other *B.t.* toxins which have the characteristic sequence shown in SEQ ID NO. 30.

The flow charts of FIGS. 1–8 provide a general overview of vector construction that can be carried out according to the subject invention. BamHI and PvuI cloning sites can be introduced into a cryIA(c)/cryIA(b) chimeric toxin gene by mutagenesis using the PCR technique of Splice Overlap Extension (SOE) (Horton, R. M., H. D. Hunt, S. N. Ho, J. K. Pullen, L. R. Pease [1989] *Gene* 77:61–68) to give plasmid pMYC2224. A region of the cryIF gene from a cryIF-containing plasmid such as pMYC1260 can be generated by PCR and substituted for the BamHI-PvuI cryIA(c)/cryIA(b) gene fragment of pMYC2224. The new plasmid, which we designated pMYC2239, consisted of a short segment of cryIA(c) followed by cryIF to the toxin/protoxin segment junction. Thus, the protoxin segment was now derived from cryIA(b) (pMYC1050). An ApaI fragment derived from the cryIF clone (pMYC2047) was substituted for the ApaI fragment in pMYC2239. The resulting clone (pMYC2244) consisted of cryIF from the initiator methionine to the toxin/protoxin segment junction and cryIA(b) to the end of the coding region. Clone pMYC2243 was constructed by SOE to introduce silent codon changes in a limited region. The ApaI fragment from pMYC2243 that contained the silent changes was substituted for the ApaI fragment in pMYC2244 to give clone pMYC2523. The chimeric pMYC2523 showed an expression improvement over pMYC2243, which contains unchanged cryIF protein sequence.

A cryIF/436 chimera can be assembled by substituting the PvuI-BstEII protein segment-containing fragment of pMYC2523 with an equivalent fragment generated by PCR from a plasmid containing a cryIA(c)/cryIA(b) gene. One such gene is the 436 gene (e.g., pMYC467, as disclosed in U.S. Pat. Nos. 5,055,294 and 5,169,760). This construction also results in improved expression compared to the native cryIF protein sequence.

Genes and toxins. The genes and toxins useful according to the subject invention include not only the full length sequences disclosed but also fragments of these sequences, variants, mutants, and fusion proteins which retain the characteristic pesticidal activity of the toxins specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins.

It should be apparent to a person skilled in this art that genes encoding active toxins can be identified and obtained through several means. The specific genes or gene portions exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

A further method for identifying the toxins and gene portions useful according to the subject invention is through the use of oligonucleotide probes. These probes are detectable nucleotide sequences. These sequences may be detectable by virtue of an appropriate label or may be made inherently fluorescent as described in International Application No. WO93/16094. As is well known in the art, if the probe molecule and nucleic acid sample hybridize by forming a strong bond between the two molecules, it can be reasonably assumed that the probe and sample have substantial homology. Preferably, hybridization is conducted under stringent conditions by techniques well-known in the art, as described, for example, in Keller, G. H., M. M. Manak (1987)*DNA Probes,* Stockton Press, New York, N.Y., pp. 169–170. Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using DNA synthesizer and standard procedures. These nucleotide sequences can also be used as PCR primers to amplify genes of the subject invention.

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. This amino acid homology will typically be greater than 75%, preferably be greater than 90%, and most preferably be greater than 95%. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

Recombinant hosts. The genes encoding the toxins of the subject invention can be introduced into a wide variety of microbial or plant hosts. Expression of the toxin gene results, directly or indirectly, in the intracellular production and maintenance of the pesticide. Conjugal transfer and recombinant transfer can be used to create a *B.t.* strain that expresses both toxins of the subject invention. Other host organisms may also be transformed with one or both of the toxin genes then used to accomplish the synergistic effect. With suitable microbial hosts, e.g., Pseudomonas, the microbes can be applied to the situs of the pest, where they will proliferate and be ingested. The result is control of the pest. Alternatively, the microbe hosting the toxin gene can be treated under conditions that prolong the activity of the toxin and stabilize the cell. The treated cell, which retains the toxic activity, then can be applied to the environment of the target pest.

Where the *B.t.* toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing a *B.t.* gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Treatment of cells. *Bacillus thuringiensis* or recombinant cells expressing the *B.t.* toxins can be treated to prolong the toxin activity and stabilize the cell. The pesticide microcapsule that is formed comprises the *B.t.* toxin or toxins within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the *B.t.* toxin gene or genes, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as glutaraldehyde; anti-infectives, such as zephiran chloride and cetylpyridimum chloride; alcohols, such as isopropyl and ethanol; various histologic fixatives, such as Lugol iodine, Bouin's fixative, various acids and Helly's fixative (See: Humason, Gretchen L., *Animal Tissue Techniques,* W. H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bioavailability or bioactivity of the toxin.

Characteristics of particular interest in selecting a host cell for purposes of production include ease of introducing the *B.t.* gene or genes into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the *B.t.* insecticidal gene or genes may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells producing the toxins of the invention can be cultured using standard art media and fermentation techniques. Upon completion of the fermentation cycle the bacteria can be harvested by first separating the *B.t.* spores and crystals from the fermentation broth by means well known in the art. The recovered *B.t.* spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations. Formulated bait granules containing an attractant and spores, crystals, and toxins of the *B.t.* isolates, or recombinant microbes comprising the genes obtainable from the *B.t.* isolates disclosed herein, can be applied to the soil. Formulated product can also be applied as a seed-coating or root treatment or total plant treatment at later stages of the crop cycle. Plant and soil treatments of *B.t.* cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest, e.g., foliage or soil, by spraying, dusting, sprinkling, or the like.

MATERIALS AND METHODS

NACS (Bethesda Research Labs, Gaithersburg, Md.) column chromatography was used for purification of electroeluted DNA. It was performed according to the manufacturer's directions, except that the buffers were modified to 0.5X TBE/0.2M NaCl for binding, and 0.5X TBE/2.0M NaCl for elution.

Random priming labeling of DNA with α-[$^{32}$P]dATP was done with a kit (Boehringer-Mannheim Biochemicals, Indianapolis, Ind.) according to the manufacturer's directions.

Gel purification refers to sequential application of agarose-TBE gel electrophoresis, electroelution, and NACS column chromatography for purification of selected DNA fragments, methods which are well known in the art.

Polymerase chain reaction (PCR) amplification of DNA was done for 25 cycles on a Perkin Elmer (Norwalk, Conn.) thermal cycler with the following cycle parameters: 94° C. for 1 minute, 37° C. for 2 minutes, 72° C. for 3 minutes (each 72° C. cycle has a 5 second extension time). PCR DNA products were proteinase K treated to improve cloning efficiency (Crowe, J. S., Cooper, H. J., Smith, M. A., Sims, M. J., Parker, D., Gewert, D. [1991] *Nucl. Acids Res.* 19:184).

Oligodeoxyribonucleotides (oligonucleotides) were synthesized on an Applied Biosystems (Foster City, Calif.) model 381A DNA synthesizer. Purification was done with Nensorb columns (New England Nuclear-Dupont, Wilmington, Del.), if necessary, according to the manufacturer's instructions.

Electroporation of Pseudomonas fluorescens was done with log-phase cells grown in L-broth (LB) at 30° C. on a rotary shaker. Cells were washed 2 to 3 times with ice-cold sterile distilled water and concentrated to 0.03x starting volume in distilled water. DNA in 1–20 μl was mixed with 50–300 μl of cells. Parameters selected for the Biorad Gene Pulser (Bio-Rad, Richmond, Calif.) were 200 ohms, 25 microfarads, and 2.25 kilovolts in a cuvette with a 0.2 cm electrode gap. Following electroporation, one milliliter of LB was added and cells were held on ice for at least 2 minutes. Cells were then incubated for 2 hours to overnight at 30° C. without shaking.

*B.t.* toxin expression in *P. fluorescens* was done in the recommended medium found in the *Manual of Methods for General Bacteriology* (P. Gerhardt et al., 1981, American Society for Microbiology, Washington, D.C.). Glycerol was substituted for glucose. The recipe was made with tap water and the pH adjusted to 7.2. Seed flasks were made from L-broth. The following recipes apply:

| Base Medium (for 1 liter) | |
|---|---|
| glycerol | 65 g |
| $(NH_4)_2SO_4$ | 1.0 g |
| $Na_2HPO_4$ | 5.24 g |
| $KH_2PO_4$ | 2.77 g |
| Yeast extract | 5.0 g |
| Casamino acids | 1.0 g |
| Metals 44 (for 100 ml) | |
| EDTA | 250 mg |
| $ZnSO_4.7H_2O$ | 1095 mg |
| $FeSO_4.7H_2O$ | 500 mg |
| $MnSO_4.H_2O$ | 154 mg |
| $CuSO_4.5H_2O$ | 39.2 mg |
| $Co(NO_3)_2.6H_2O$ | 24.8 mg |
| $Na_2B_4O_7.10H_2O$ | 17.7 mg |

| Huntner's Mineral Mix (for 1 liter) | |
|---|---|
| Nitriloacetic acid (dissolved and neutralized with KOH) | 10 g |
| $MgSO_4.7H_2O$ | 14.45 g |
| $CaCl_2.2H_2O$ | 3.33 g |
| $(NH_4)_6Mo_7O_{24}.4H_2O$ | 9.25 g |
| $FeSO_4.7H_2O$ | 99 mg |
| Metals 44 | 50 ml |
| pH adjusted to 6.6–6.8 | |

At inoculation for analysis of *B.t.* toxin expression, 4 ml of Huntner's Mineral Mix was added per 200 ml of broth. Flasks were then given a 2% inoculum, by volume, of an overnight culture. Cultures were allowed to grow for 24 hours at 32° C. at ≧200 rpm. At this point, they were induced with 0.75 mM IPTG and supplemented with 2 g yeast extract. Protein gels were run on samples pulled at 48 and 72 hours. The 130 kDa protein was quantified by laser densitometry.

Following are examples which illustrate procedures, including the best mode, for practicing the invention. These examples should not be construed as limiting. All percentages are by weight and all solvent mixture proportions are by volume unless otherwise noted.

EXAMPLE 1

Expression Vector Modification by Splice Overlap Extension (SOE)

A cloning vector can be constructed based on pTJS260, a broad host-range plasmid derived from RSF1010 (pTJS260 can be obtained from Dr. Donald Helinski, U.C. San Diego). An example of the system used in the vector construction can be found in EPO patent application 0 471 564. A cryIA(c)/cryIA(b) gene, referred to herein as the 436 gene and toxin, are described in U.S. Pat. No. 5,055,294. A plasmid designated pMYC1050 contains the 436 gene. pMYC1050 was constructed by re-cloning the toxin gene and promoter of pM3,130-7 (disclosed in U.S. Pat. No. 5,055,294) into a pTJS260-based vector such as pMYC467 (disclosed in U.S. Pat. No. 5,169,760) by methods well known in the art. In particular, the pM3,130-7 promoter and toxin gene can be obtained as a BamHI to NdeI fragment and placed into the pMYC467 plasmid replacing a fragment bounded by the same sites (BamHI near base 12100 and NdeI near base 8000).

The improved vector ideally contains a unique BamHI cloning site. The plasmid BamHI site, located upstream from the tac promoter (Ptac), can be removed by blunting with Klenow and religating (FIG. 1). Absence of the site can be confirmed by restriction digestion. A plasmid produced according to this procedure was called pMYC1050ΔBamHI. The construct can now have a BamHI site added to the plasmid by SOE mutagenesis. SOE mutagenesis can be facilitated by subcloning an NsiI toxin-containing DNA fragment into the smaller pGEM5 (Promega Corp., Madison, Wis.) vector which uses the ampicillin resistance (bla) gene as a selectable marker (FIG. 1). The fragment can be oriented by restriction digestion. A plasmid produced according to this procedure was called pGEMtox.

Figure 2:
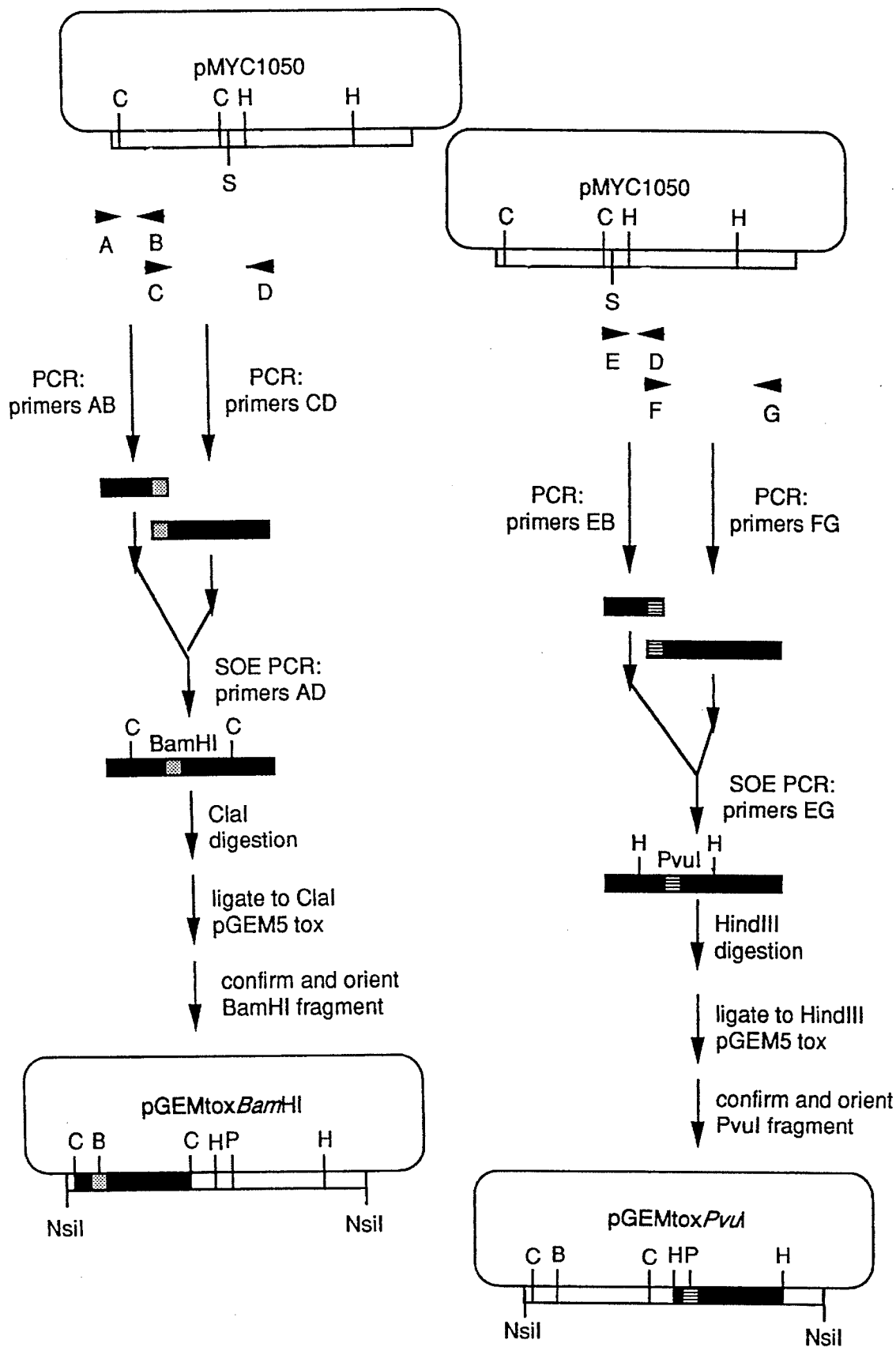
FIG. 2—BamHI or PvuI cloning sites were introduced into toxin DNA by the technique of Splice Overlap Extension (SOE). DNA fragments with the new sites are used to replace homologous DNA fragments in pGEMtox. The resulting plasmids are pGEMtoxBamHI or pGEMtoxPvuI. The letters A through G below the arrows correspond to oligonucleotide primers in the text. Letters above vertical lines correspond to restriction enzyme sites. B=BamHI, C=ClaI, H=HindIII, P=PvuI, S=SacI.
Figure 3:
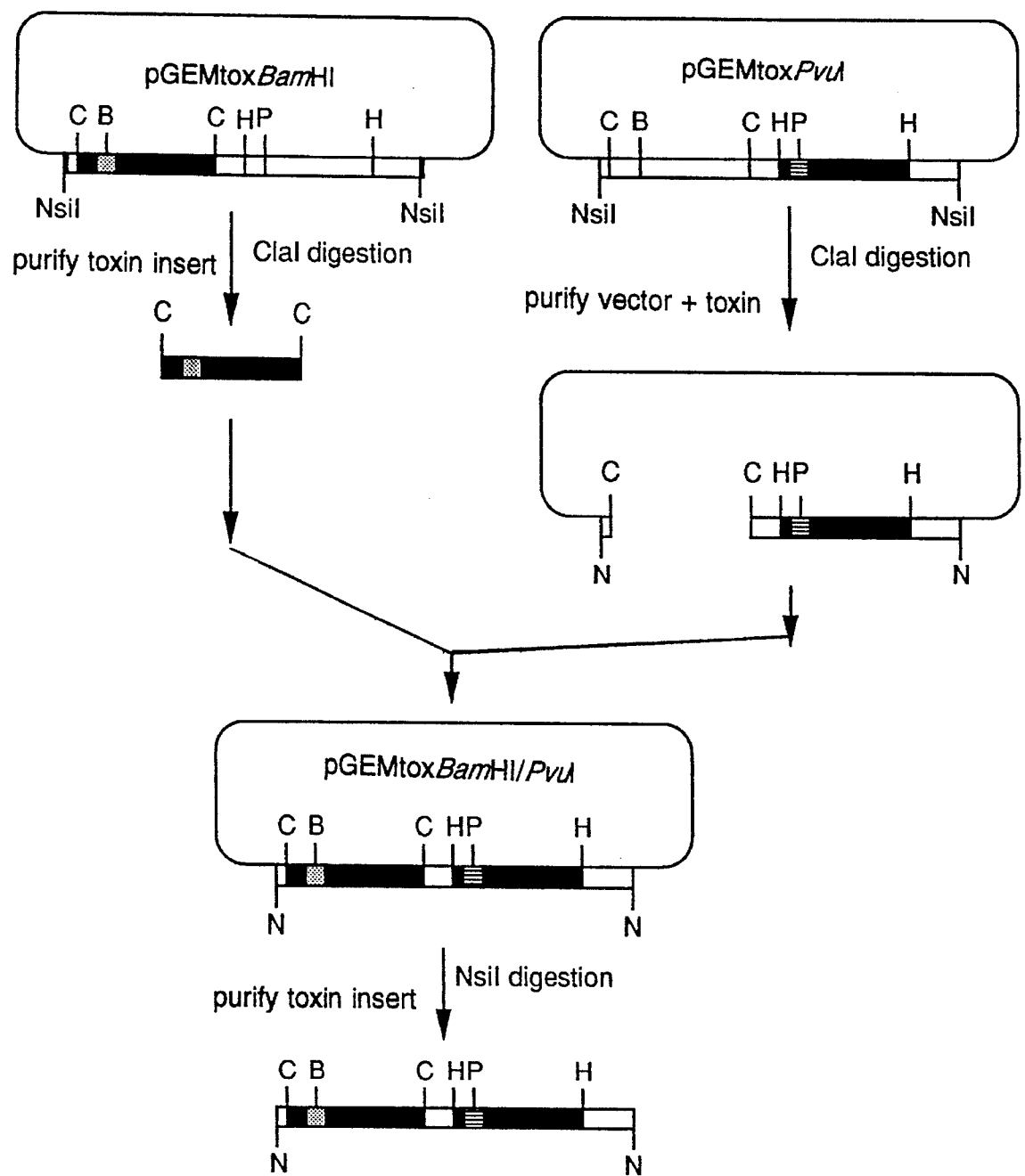
FIG. 3—The DNA fragment containing the BamHI mutation is used to replace the homologous fragment in pGEMtoxPvuI. The resulting plasmid which contains both cloning sites is pGEMtoxBamHI/PvuI. To construct an expression plasmid, the toxin-containing NsiI fragment is excised for cloning into the pTJS260 broad host-range vector. B=BamHI, C=ClaI, H=HindIII, P=PvuI.
Figure 4:
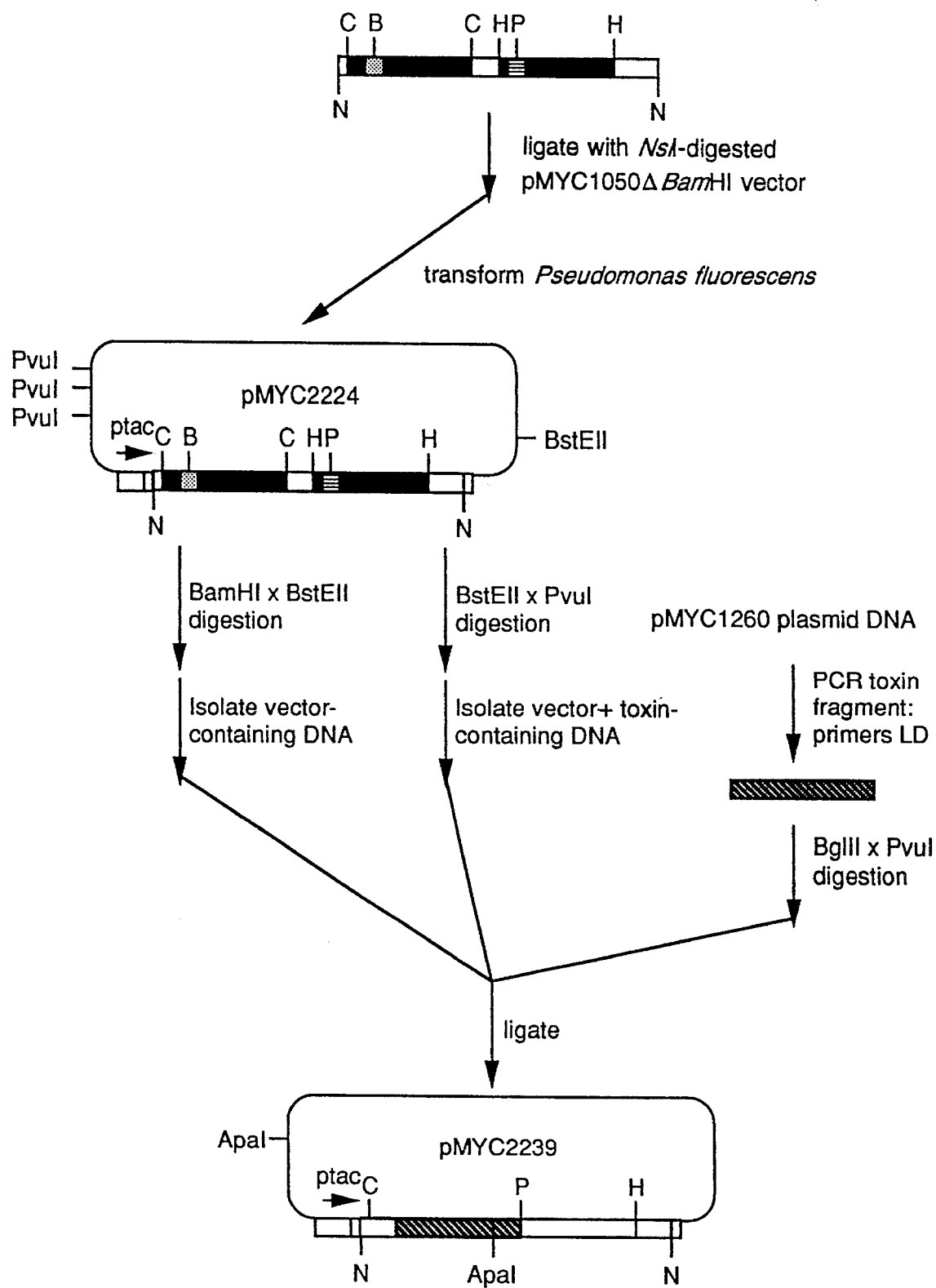
FIG. 4—The NsiI toxin-containing fragment with the new restriction sites is ligated to the vector-containing DNA from pMYC1050ΔBamHI to give pMYC2244. ABamHI-PvuI PCR-derived DNA fragment containing the cryIF toxin is exchanged for the equivalent fragment in pMYC2244. The resulting chimera is called pMYC2239. B=BamHI, C=ClaI, H=HindIII, N=NsiI, P=PvuI.
Figure 5:
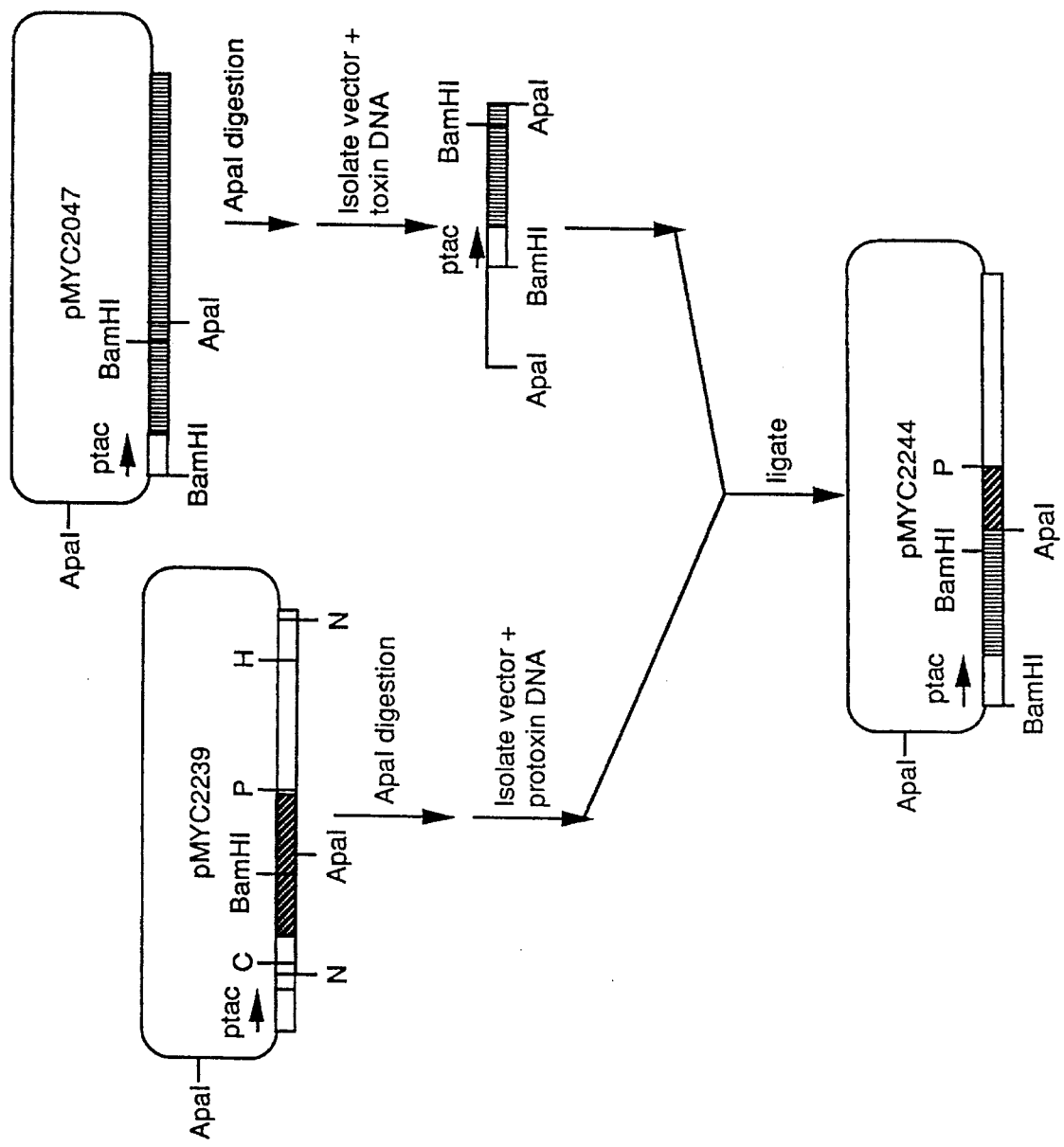
FIG. 5—The small ApaI DNA fragment of pMYC2047 is substituted for the homologous region of pMYC2239 to give plasmid pMYC2244. This chimera consists of cryIF in the toxin region and cryIA(b) in the protoxin. C=ClaI, H=HindIII, N=NsiI, P=PvuI.
Figure 6:
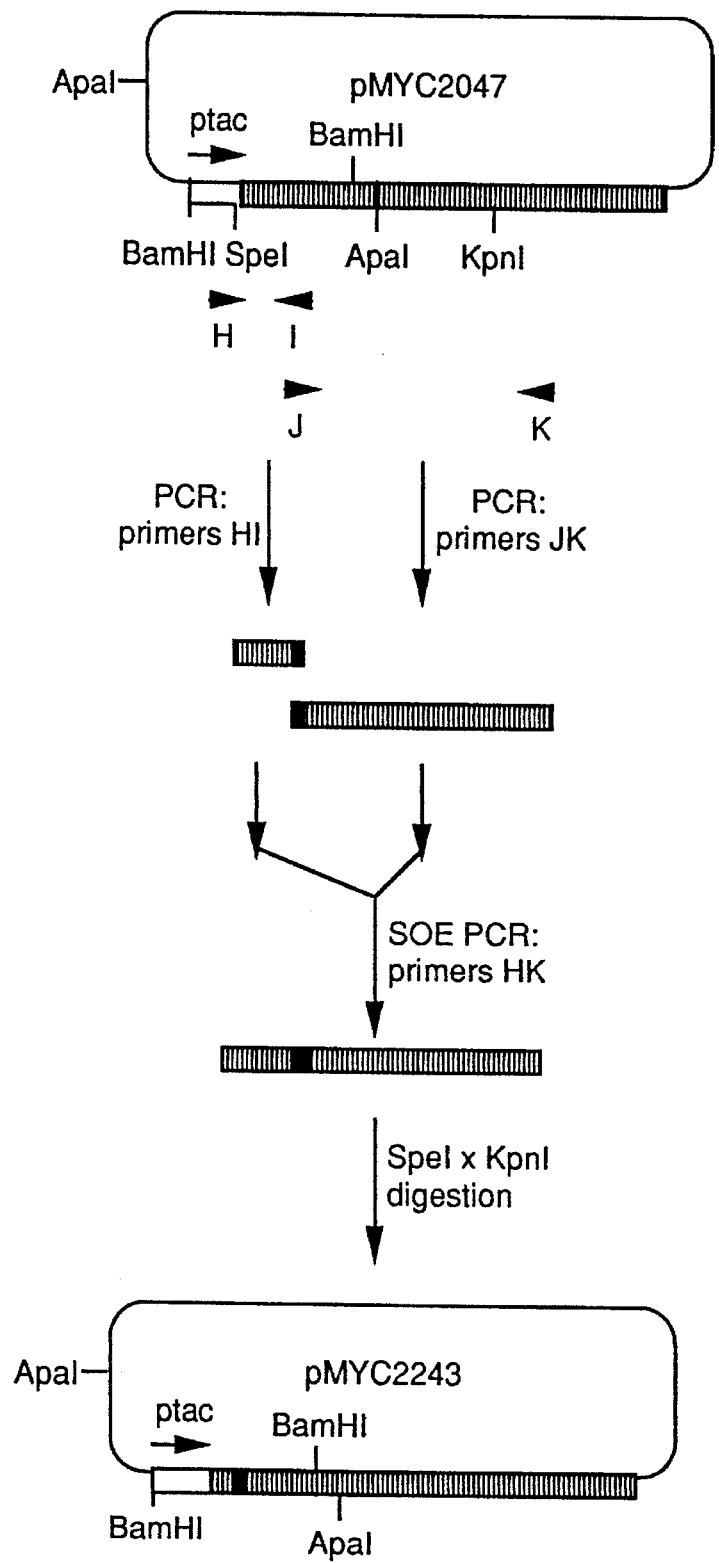
FIG. 6—Silent codon changes are introduced into the cryIF toxin by SOE. The SpeI-KpnI PCR DNA fragment with the changes is substituted for the homologous toxin-containing fragment in pMYC2047. The resulting plasmid is pMYC2243. Letters H through K below the arrows correspond to oligonucleotide primers in the text.
Figure 7:
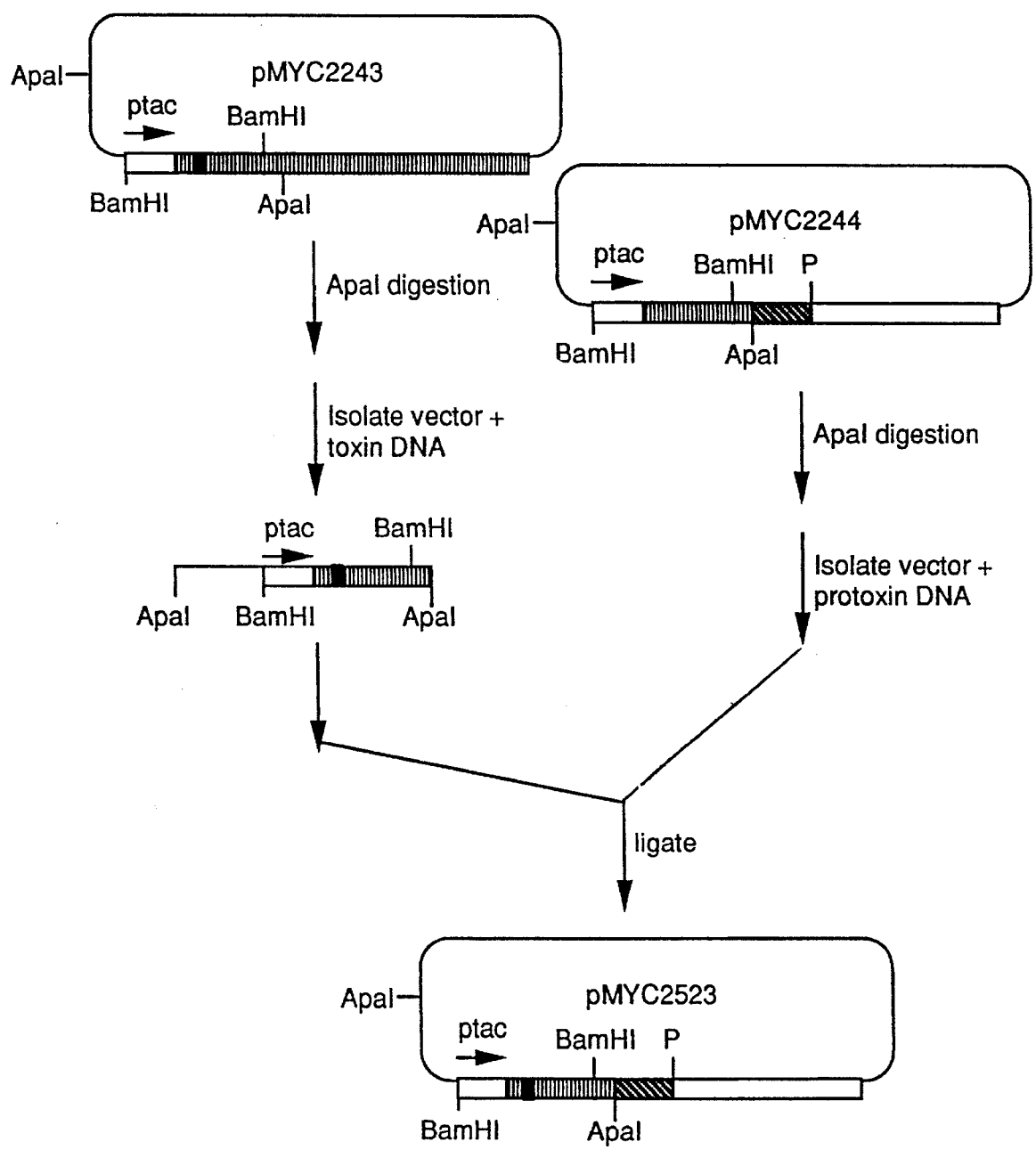
FIG. 7—Silent codon changes are introduced into pMYC2244 by substitution of the homologous fragment with the small ApaI DNA fragment of pMYC2243. The final plasmid is pMYC2523. P=PvuI.

DNA in the toxin coding region can be mutated by the PCR-mediated technique of SOE to introduce restriction enzyme cloning sites as shown in FIG. 2. Oligonucleotides useful as primers are shown below:

"A" (SEQ ID NO. 1)
5' GCATACTAGTAGGAGATTTCCATGGATAACAATC-CGAAC 3'
"B" (SEQ ID NO. 2)
5' GGATCCGCTTCCCAGTCT 3'
"C" (SEQ ID NO. 3)
5' AGAGAGTGGGAAGCGGATCCTACTAATCC 3'
"D" (SEQ ID NO. 4)
5' TGGATACTCGATCGATATGATAATCCGT 3'
"E" (SEQ ID NO. 5)
5' TAATAAGAGCTCCTATGT 3'
"F" (SEQ ID NO. 6)
5' TATCATATCGATCGAGTATCCAATTTAG 3'
"G" (SEQ ID NO. 7)
5' GTCACATAGCCAGCTGGT 3' pMYC1050 DNA was used as the template for PCR amplification using primer sets A/B, C/D, E/D, and F/G. Amplified DNA fragments were named AB, CD, ED, and FG. Amplified DNAs were purified by agarose-TBE gel electrophoresis, electroelution, and NACS column chromatography, methods all well-known in the art. Purified template DNAs were used in a second set of PCR reactions. Fragments AB and CD were mixed and amplified with primers A and D. In a separate reaction, fragments ED and FG were mixed and amplified with primers E and G. Amplified DNA was resolved by agarose-TBE gel electrophoresis and the fragments with the corresponding increase in size were excised, electroeluted, and purified over NACS columns by means well known in the art. Amplified DNA fragments are called AD or EG for reference.

DNA fragments AD or EG with the new restriction enzyme sites were incorporated into the toxin-containing DNA by several subcloning procedures (FIGS. 2 and 3). pGEMtox was digested with ClaI or HindIII. Vector-containing DNA was gel-purified. Fragment AD was digested with ClaI and ligated to ClaI-digested pGEMtox vector DNA. Fragment EG was digested with HindIII and ligated to HindIII-digested pGEMtox vector DNA. *E. coli* strain NM522 was transformed with ligation mixes. Correctly assembled constructs were identified by restriction enzyme digestion of plasmid DNA from isolated colonies. The plasmid with the new BamHI site was called pGEM tox BamHI. The plasmid with the new PvuI site was called pGEMtox PvuI. The ClaI fragment containing the BamHI site from plasmid pGEMtox BamHI was ligated to the phosphatased ClaI vector-containing fragment from pGEMtox PvuI. *E. coli* strain NM522 was transformed with ligation mixes. Correctly assembled constructs were identified by PCR analysis with primer set C/D, and by restriction digestion. The plasmid with both new restriction enzyme sites was called pGEMtox BamHI/PvuI.

A completed expression vector was assembled with insert from pGEMtox BamHI/PvuI and vector from pMYC1050ΔBamHI (FIGS. 3 and 4). Gel-purified insert was prepared from pGEMtox BamHI/PvuI by NsiI digestion, and ScaI digestion (to remove contaminating vector). It was ligated to gel-purified NsiI-digested vector-containing pMYC1050ΔBamHI DNA. *E. coli* strain NM522 was transformed with the ligation mixes, and transformation mixes were plated on LB agar containing tetracycline at 12 μg/ml. Colonies containing the NsiI insert were identified by colony hybridization and autoradiography. Inserts were oriented by PCR, using primer set A/D, which bridges an NsiI cloning site, and agarose-TBE gel electrophoresis. The correctly assembled plasmid is called pMYC2224. DNA and protein sequences of the toxin are found in SEQ ID NOS. 18 and 19, respectively. A lactose-inducible *P. fluorescens* strain was electroporated with correctly assembled plasmid DNA. Transformation mixes were plated on LB agar containing tetracycline at 20 μg/ml. Plasmid DNA was prepared from *P. fluorescens* for use in subsequent cloning experiments.

EXAMPLE 2

Subcloning the cryIF Hypervariable Region into pMYC2224

A DNA fragment containing the hypervariable region from cryIF (pMYC1260) was exchanged for the BamHI-PvuI toxin-containing DNA fragment from pMYC2224 (FIG. 4). Since the coding sequence contains a preexisting BamHI site, BglII was chosen for cloning. The 4-base overhangs of BamHI and BglII are compatible, permitting ligation while eliminating both sites from the junction. It was necessary to synthesize a new primer for PCR:

"L" (SEQ ID NO. 8)

5' GAGTGGGAAGCAGATCTTAATAATGCA-CAATTAAGG 3'

A toxin-containing DNA fragment was generated by PCR with primers L/D on template pMYC1260. The DNA was digested with BglII and PvuI for subcloning. Since the tetAR locus contains multiple PvuI sites, it was necessary to isolate the vector-containing DNA on two separate fragments. To obtain the first fragment, pMYC2224 was digested with BamHI x BstEII, and the large DNA fragment containing the Ptac-tetAR locus-rep functions was gel-purified. To obtain the second fragment, pMYC2224 was digested with BstEII x PvuI, and the DNA fragment containing the vector-protoxin module was gel-purified. A three-piece ligation was set up and used for *E. coli* strain NM522 transformation. Grossly correct plasmids were identified by PCR analysis and agarose-TBE gel electrophoresis using the primer set N/O, which bridges the BamHI/BglII fusion junction.

"N" (tac promoter) (SEQ ID NO. 9)

5' TTAATCATCGGCTCGTA 3'

"O" (SEQ ID NO. 10)

5' ACTCGATCGATATGATA(GA)TCCGT 3'

The correct plasmid was named pMYC2239. It consists of cryIA(c) at the amino-terminus, cryIF up to the toxin/protoxin junction, and cryIA(b) through the protoxin segment. The toxin DNA and protein sequences are in SEQ ID NOS. 20 and 21, respectively.

EXAMPLE 3

Construction of the *P. fluorescens* Expression Plasmids pMYC1260 and pMYC2047

The cloned toxin gene cryIF can be modified for expression in *P. fluorescens* in the following way:

1. A plasmid containing the pKK223-3 rrnB termination sequences in the pTJS260-derived vector (Dr. Donald Helinski, U.C. San Diego) can be made by ligating the BamHI-ScaI fragment containing the Ptac promoter and rrnB terminator from pKK223-3 (Pharmacia E. coli vector) into the BamHI to blunted KpnI vector fragment of pMYC1197 (described in EP 0 417 564). The assembled plasmid is recovered following transformation of E. coli and growth under tetracycline selection.

2. A plasmid containing the Ptac-promoted cryIF toxin gene can be made by ligating toxin gene-containing NdeI-Nde-I fragment (with ends blunted using DNA polymerase and dNTPs) of about 3800 bp from pMYC1603 (from NRRL B-18517) into the blunted EcoRI and HindIII sites of pKK223-3. The Ptac-promoted cryIF toxin plasmid can be recovered following transformation of E. coli, grown under ampicillin selection, and screening for plasmids with inserts in the proper orientation for expression from the Ptac promoter by techniques well known in the art.

3. The Ptac-promoted cryIF toxin can be assembled into the pTJS260-derived vector in a three-piece ligation using the 2.4 kb DNA fragment having BamHI and ApaI ends from the plasmid pTJS260, ApaI to HindIII fragment of 8.5 kb containing the replication region of the plasmid from step 1 above, and a HindIII to partial BamHI fragment containing the Ptac promoter and cryIF toxin gene from step 2 above.

The resulting pTJS260-derived cryIF toxin expression plasmid (pMYC1260) can be introduced into *P. fluorescens* by electroporation.

4. pMYC2047 can be constructed by ligating an SpeI to KpnI fragment obtained through PCR of a suitable cryIF template with primers H and K followed by digestion with SpeI and KpnI and gel purification, an ApaI to KpnI fragment of ca. 10 kb from the plasmid of step 3, and the ApaI to SpeI fragment of ca. 2600 bp from pMYC1197 containing the Ptac promoter. The correct cryIF toxin expression plasmids are determined by restriction enzyme digestion of plasmids following electroporation into *Pseudomonas fluorescens.*

EXAMPLE 4

Construction of a cryIF/cryIA(b) Chimera

The cryIA(c) segment at the amino-terminus can be replaced by the cryIF coding sequence by a simple, straightforward swap (FIG. 5). Both the tetAR locus and cryIF coding sequence contain an ApaI site. A small ApaI fragment containing a portion of the tetAR genes and the amino-terminus of cryIF can be isolated from pMYC2047 and ligated to the large ApaI vector-containing fragment from pMYC2239. A *P. fluorescens* lactose-inducible strain can be electroporated with the ligation mix and plated on LB agar containing tetracycline at 20 μg/ml. Lactose-inducible strains are known to those skilled in the art and are described, for example, in U.S. Pat. No. 5,169,760. Correct orientation of the ApaI fragment reconstitutes tetracycline resistance. A clone produced in this manner was shown to be grossly correct by restriction enzyme digestion, and it was named pMYC2244. The toxin DNA sequence is shown in SEQ ID NO. 22, and the predicted protein sequence is shown in SEQ ID NO. 23.

EXAMPLE 5

Construction of a Limited Codon Rework of cryIF

Codon usage in Pseudomonas spp. favors G or C in the wobble position of triplet codons, as determined by analysis of genes in the GenBank/EMBL sequence libraries. A limited region of the cryIF gene was reworked by SOE to incorporate favored wobble position changes that were silent (FIG. 6). Oligos used are shown below:

"H" (SEQ ID NO. 11)

5' GGACTAGTAAAAAGGAGATAACCATGGAAAATA-ATATTCAAAATC 3'

"I" (SEQ ID NO. 12)

5' TCCAGCGGCAGGCGGCCGGTGCTGCGTTCTTC-GTTCAGTATTTCTACT TCAGGATTATTTAAAC 3'

"J" (SEQ ID NO. 13)

5' AACGCAGCACCGGCCGCCTGCCGCTGGACATCA-GCCTGAGCCTTACAC GTTTCCTTTTGAGTGAA 3'

"K" (SEQ ID NO. 14)

5' CATCAAAGGTACCTGGT 3'

Two separate PCR reactions were done on pMYC2047 template with primer sets H/I or J/K. Amplified DNA fragments were called HI or JK. A second PCR reaction was set up by mixing fragments HI and JK and PCR amplifying with primer set H/K. The larger SOE DNA was gel-purified and digested with SpeI x KpnI. A three-piece ligation was set up with SpeI-ApaI Ptac-tetAR locus DNA, ApaI-KpnI vector-protoxin module DNA, and SpeI-KpnI PCR DNA. A *P. fluorescens* lactose-inducible strain can be electroporated with the ligation mix. Grossly correct clones can be identified by PCR analysis using the primer set P/Q and agarose-TBE gel electrophoresis. Oligo P (SEQ ID NO. 15) was designed to discriminate between the wild-type and codon-reworked gene.

"P" (SEQ ID NO. 15)

5' TGCCGCTGGACATCAGCCTGAG 3'

"Q" (SEQ ID NO. 16)

5' TCTAGAGCGGCCGCTTATAC(CT)CGATC-GATATGATA(GA)TCCGT 3'

The complete plasmid was named pMYC2243. The toxin DNA sequence is shown in SEQ ID NO. 24. The toxin protein sequence is predicted to be unchanged, and is shown in SEQ ID NO. 25.

EXAMPLE 6

Construction of the cryIF/cryIA(b) Chimera Containing the Limited Codon Rework The construct was assembled (FIG. 7) using the same ApaI fragment exchange strategy as for pMYC2244 (cryIF/cryIA(b)) above. The small, toxin-tetAR locus ApaI DNA fragment was gel-purified from pMYC2243. The larger vector-protoxin module ApaI DNA fragment was gel-purified from pMYC2244. The completed plasmid was named pMYC2523. Predicted DNA and protein sequences are in SEQ ID NOS. 26 and 27, respectively:

EXAMPLE 7

Comparative Expression of Toxins from pMYC2244 and pMYC2523

Toxin expression in *P. fluorescens* was analyzed as described above. At 24 and 48 hours post-induction, the pMYC2523-containing strain produced more toxin than the pMYC2244-containing strain. Toxin specific activity on *Spodoptera exigua* was statistically unchanged.

EXAMPLE 8

Construction of the cryIF/436 Chimera Containing the Limited Codon Rework

Figure 8:
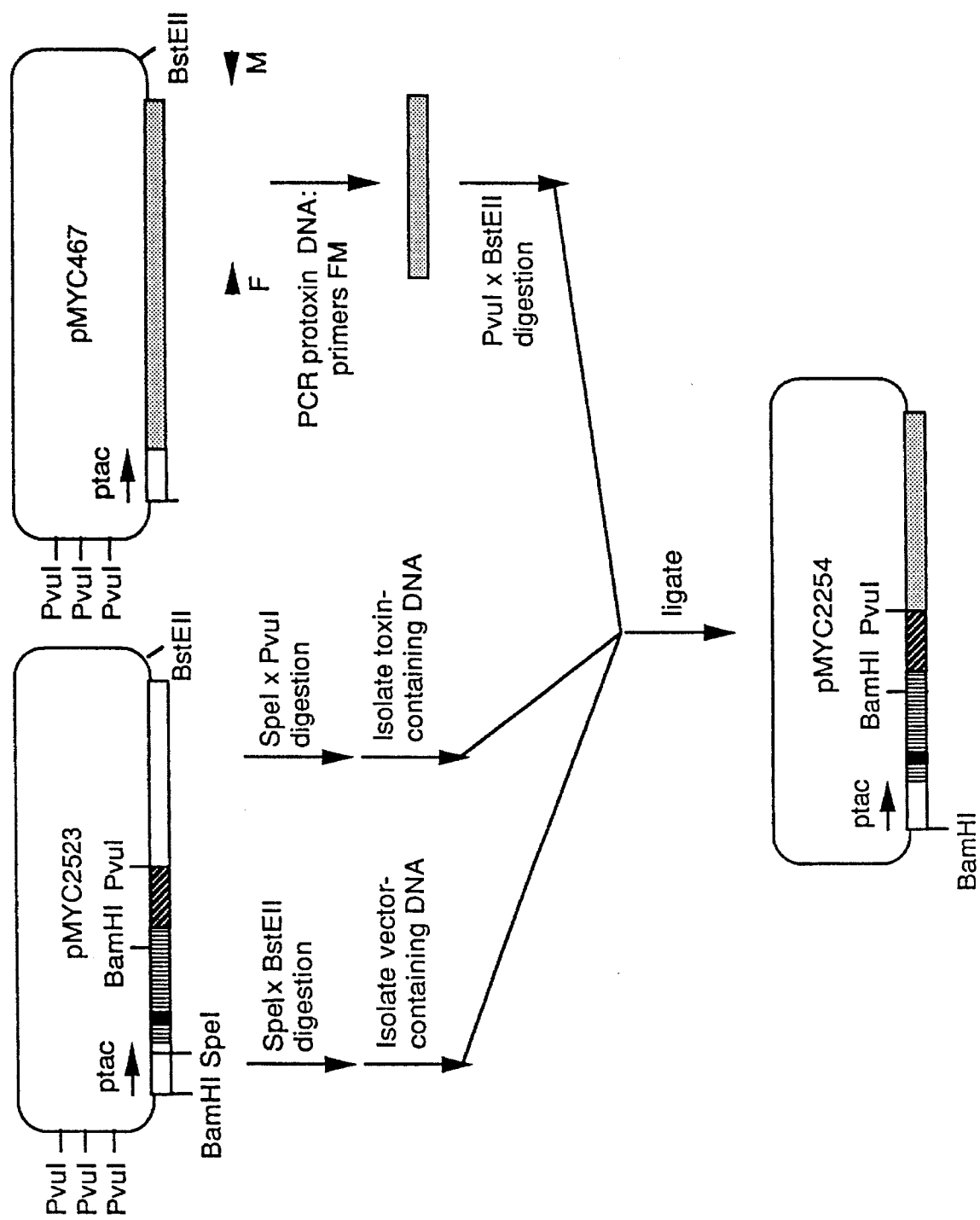
FIG. 8—A chimeric toxin containing the 436 protoxin is constructed by substituting a PCR-generated PvuI-BstEII protoxin DNA for the homologous fragment in pMYC2523. The final plasmid is pMYC2254. Letters F and M below the arrows correspond to oligonucleotide primers in the text.

A second type of chimeric toxin was assembled by substituting the 436 protoxin module for the cryIA(b) protoxin in pMYC2523 (FIG. 8). The 436 protoxin sequence consists of cryIA(c) sequence except at the very C-terminus (See U.S. Pat. Nos. 5,128,130 and 5,169,760, incorporated herein by reference in their entirety). Protoxin DNA for cloning was generated by PCR with the primer set F/M using a plasmid such as pMYC467 (U.S. Pat. No. 5,169,760) as a template.

"M" (SEQ ID NO. 17)
5' AGGCTTCCATAGATACCTTGTGCG 3'

PCR DNA was digested with PvuI x BstEII. A three-piece ligation was set up with SpeI-PvuI toxin DNA from pMYC2523, SpeI-BstEII vector DNA from pMYC2523, and PvuI-BstEII PCR protoxin module DNA. A lactose-inducible *P. fluorescens* strain was electroporated with the ligation mix. Grossly correct plasmids were identified by PCR with primer set F/G and screening for slight size increase by agarose-TBE gel electrophoresis. The construct was named pMYC2254. Predicted DNA and protein sequences are found in SEQ ID NOS. 28 and 29, respectively.

EXAMPLE 9

Comparative Expression of Toxins from pMYC2243 and pMYC2254

Toxin expression in *P. fluorescens* was analyzed as described above. Toxin expression from pMYC2254 was improved over pMYC2243 expression.

EXAMPLE 10

Analysis for Synergy Between CryIF Chimeric Toxin and CryIA(c) Chimeric Toxin Against the Corn Earworm, *Heliothis zea*

Twenty-four *Heliothis zea* first instar larvae were exposed to agar diet containing various concentrations of toxin. At 7 days post treatment, assays were graded for growth inhibition. Larvae were inhibited if the molt from first to second instar was inhibited. Calculations for estimating synergy factor (SF) and expected activity (E[exp]) are shown below.

SF=E(obs)/E(exp)

where,
SF=synergy factor
E(obs)=observed mortality
E(exp)=expected mortality

E(exp)=a+b−(ab/100)

where,
a=activity from compound A
b=activity from compound B

TABLE 2

| | % INHIBITION | | | | |
|---|---|---|---|---|---|
| Rate | cryIF/cryIA(b) | cryIA(c)/cryIA(b) | 1:1 mix of the two chimeric toxins | | |
| μg toxin/g diet | a | b | E(exp) | E(obs) | SF |
| 50.0 | — | — | 50 | 78 | 1.6 |
| 25.0 | 13 | 23 | 22 | 62 | 2.8 |
| 12.5 | 9 | 14 | 22 | 31 | 1.4 |
| 6.25 | 9 | 14 | — | — | — |

An SF greater than 1 indicates synergy (Levy, Y., M. Benderly, Y. Cohen, U. Gisi, D. Bassard [1986] Bulletin OEPP/EPPO Bulletin 16:651–657).
Abbott, W.S. (1925) J. Economic Entomology 18:265–267.

EXAMPLE 11

Analysis for Synergy Between CryIF Chimeric Toxin and CryIA(c) Chimeric Toxin Against the Corn Earworm, *Heliothis zea*

Twenty-four *Heliothis zea* first instar larvae were exposed to agar diet containing various concentrations of toxin. At 7 days post treatment, assays were graded for growth inhibition. Larvae were inhibited if the molt from first to second instar was inhibited. The dosage required to inhibit 50 percent of the populations ($ED_{50}$) was estimated using standard probit analysis techniques. Calculations for estimating synergy factor (SF) and expected effective dosages (ED[exp]) are shown below.

SF=ED(exp)/ED(obs)

where,
ED(exp)=expected effective dose of a mixture
ED(obs)=observed effective dose of a mixture ED(exp)=(a+b)/a/$ED_A$+b/$ED_B$ where,
a=proportion of compound A in mixture
b=proportion of compound B in mixture
$ED_A$ and $ED_B$=equally effective doses of A and B in mixture.

TABLE 3

| Treatment | ED(obs) (μg toxin/g diet) | ED(exp) | SF |
|---|---|---|---|
| cryIA(c)/cryIA(b) (A) | 36 | — | — |
| cryIF/cryIA(b) (B) | 135 | — | — |
| A:B (1:1) | 21 | 57 | 2.6 |
| A:B (3:1) | 14 | 44 | 3.1 |
| A:B (1:3) | 35 | 80 | 2.3 |

A SF greater than 1 indicates synergy (Levy et al. [1986], supra). [CITE for Wadley method]

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A composition for controlling lepidopteran pests comprising a CryIF chimeric core toxin-containing protein and a CryIA(c) chimeric core toxin-containing protein.

2. The composition, according to claim 1, wherein said CryIF chimeric core toxin-containing protein comprises a CryIF core N-terminal protein portion and a heterologous C-terminal toxin portion from a CryIA(b) toxin or CryIA(b)/CryIA(c) chimeric toxin.

3. The composition, according to claim 2, wherein said CryIF chimeric core toxin-containing protein has approximately 1150 to 1200 amino acids and comprises a CryIF core N-terminal sequence of at least about 590 amino acids and no more than about 1100 amino acids, wherein said CryIA(b) or CryIA(c)/CryIA(b) portion comprises at least 100 amino acids at the C-terminus of said protein.

4. The composition, according to claim 2, wherein the transition from CryIF core N-terminal toxin portion to heterologoos portion occurs after the sequence shown in SEQ ID NO. 30 and before the end of the peptide sequence of SEQ ID NO. 31.

5. The composition, according to claim 4, wherein said core toxin portion comprises the first about 601 amino acids of a CryIF toxin and wherein said C-terminal protoxin portion comprises the CryIA(b) or CryIA(c)/CryIA(b) amino acid sequence which follows the peptide sequence shown in SEQ ID NO. 31.

6. The composition, according to claim 4, wherein said core toxin-containing protein comprises of the amino acid sequence shown in SEQ ID NO. 23.

7. The composition, according to claim 4, wherein said core toxin-containing protein comprises essentially of the amino acid sequence shown in SEQ ID NO. 29.

8. The composition, according to claim 1, wherein said CryIA(c) chimeric core toxin-containing protein has an amino acid sequence comprising the sequence shown in SEQ ID NO. 34.

9. A method for controlling lepidopteran pests comprising contacting said pests, or the environment of said pests, with an effective amount of a composition comprising a CryIF chimeric core toxin-containing protein and a CryIA(c) chimeric core toxin-containing protein.

10. The method, according to claim 9, wherein said CryIF chimeric core toxin-containing protein comprises a CryIF core N-terminal toxin portion and a heterologous C-terminal protoxin portion from a CryIA(b) toxin or CryIA(b)/CryIA(c) chimeric toxin.

11. The method, according to claim 10, wherein said CryIF chimeric core toxin-containing protein has approximately 1150 to 1200 amino acids and comprises a CryIF core N-terminal sequence of at least about 590 amino acids and no more than about 1100 amino acids, wherein said CryIA(b) or CryIA(c)/CryIA(b) protoxin portion comprises at least 100 amino acids at the C-terminus of said protein.

12. The method, according to claim 10, wherein the transition from CryIF core N-terminal toxin portion to heterologous protoxin portion occurs after the sequence shown in SEQ ID NO. 30 and before the end of the peptide sequence of SEQ ID NO. 31.

13. The method, according to claim 12, wherein said core toxin portion comprises the first about 601 amino acids of a CryIF toxin and wherein said C-terminal protoxin portion comprises the CryIA(b) or CryIA(c)/CryIA(b) amino acid sequence which follows the peptide sequence shown in SEQ ID NO. 31.

14. The method, according to claim 12, wherein said core toxin-containing protein comprises of the amino acid sequence shown in SEQ ID NO. 23.

15. The method, according to claim 12, wherein said core toxin-containing protein comprises of the amino acid sequence shown in SEQ ID NO. 29.

16. The method, according to claim 10, wherein said CryIA(c) chimeric core toxin-containing protein has an amino acid sequence comprising the sequence shown in SEQ ID NO. 34.

17. The method, according to claim 10, wherein said CryIF chimeric and CryIA(c) chimeric core toxin-containing proteins are from a host cell transformed to express SEQ ID NO. 23 and SEQ ID NO. 34.

\* \* \* \* \*

UNITED STATES PATENT AND TRADEMARK OFFICE
CERTIFICATE OF CORRECTION

PATENT NO. : 5,508,264
DATED : April 16, 1996
INVENTOR(S) : Gregory A. Bradfisch, Mark Thompson; George E. Schwab It is certified that error appears in the above-indentified patent and that said Letters Patent is hereby corrected as shown below:

Column 2: Line 17: "core toxin. is" should read --core toxin is--.
Column 4: Line 49: "A CryIF/CryIA(b)" should read --A CryIF/CryIA(b)--.
Column 5: Line 31: "cryIF/cryIA(b)" should read --cryIF/cryIA(b)--.
Column 6: Line 16: "fights" should read --rights--.
Column 7: Line 12: "Ash" should read --Asn--.
Column 14: Lines 17-18: "   " should read --Add a few drops of 6NH$_2$SO$_4$ to retard precipitation.--
Column 16: Line 30: "BgIII" should read --BgII--; Line 31: "BgIII" should read --BgII--; Line 39: "BgIII" should read --BgII--; Line 50: "BgIII" should read --BgII--.
Column 18: Line 54: "respectively:" should read --respectively.--
Column 97: Line 38: "heterologoos" should read --heterologous--; Line 50: "comprises of the amino" should read --comprises the amino--; Lines 54-55: "comprises essentially of the amino" should read --comprises the amino--.

Signed and Sealed this

Fifteenth Day of October, 1996

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 39 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:1:

GCATACTAGT AGGAGATTTC CATGGATAAC AATCCGAAC         39

( 2 ) INFORMATION FOR SEQ ID NO:2:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

GGATCCGCTT CCCAGTCT         18

( 2 ) INFORMATION FOR SEQ ID NO:3:

( i ) SEQUENCE CHARACTERISTICS:
        ( A ) LENGTH: 29 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:3:

AGAGAGTGGG AAGCGGATCC TACTAATCC         29

( 2 ) INFORMATION FOR SEQ ID NO:4:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:4:

TGGATACTCG ATCGATATGA TAATCCGT         28

( 2 ) INFORMATION FOR SEQ ID NO:5:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:5:

```
TAATAAGAGC TCCTATGT                                                               18
```

( 2 ) INFORMATION FOR SEQ ID NO:6:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:6:

```
TATCATATCG ATCGAGTATC CAATTTAG                                                    28
```

( 2 ) INFORMATION FOR SEQ ID NO:7:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:7:

```
GTCACATAGC CAGCTGGT                                                               18
```

( 2 ) INFORMATION FOR SEQ ID NO:8:

( i ) SEQUENCE CHARACTERISTICS:
        ( A ) LENGTH: 36 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:8:

```
GAGTGGGAAG CAGATCTTAA TAATGCACAA TTAAGG                                           36
```

( 2 ) INFORMATION FOR SEQ ID NO:9:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:9:

```
TTAATCATCG GCTCGTA                                                                17
```

( 2 ) INFORMATION FOR SEQ ID NO:10:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:10:

```
ACTCGATCGA TATGATARTC CGT                                                         23
```

( 2 ) INFORMATION FOR SEQ ID NO:11:

( i ) SEQUENCE CHARACTERISTICS:

( A ) LENGTH: 45 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:11:

GGACTAGTAA AAAGGAGATA ACCATGGAAA ATAATATTCA AAATC    45

( 2 ) INFORMATION FOR SEQ ID NO:12:

( i ) SEQUENCE CHARACTERISTICS:
( A ) LENGTH: 64 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:12:

TCCAGCGGCA GGCGGCCGGT GCTGCGTTCT TCGTTCAGTA TTTCTACTTC AGGATTATTT    60

AAAC    64

( 2 ) INFORMATION FOR SEQ ID NO:13:

( i ) SEQUENCE CHARACTERISTICS:
( A ) LENGTH: 65 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:13:

AACGCAGCAC CGGCCGCCTG CCGCTGGACA TCAGCCTGAG CCTTACACGT TTCCTTTTGA    60

GTGAA    65

( 2 ) INFORMATION FOR SEQ ID NO:14:

( i ) SEQUENCE CHARACTERISTICS:
( A ) LENGTH: 17 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:14:

CATCAAAGGT ACCTGGT    17

( 2 ) INFORMATION FOR SEQ ID NO:15:

( i ) SEQUENCE CHARACTERISTICS:
( A ) LENGTH: 22 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:15:

TGCCGCTGGA CATCAGCCTG AG    22

( 2 ) INFORMATION FOR SEQ ID NO:16:

( i ) SEQUENCE CHARACTERISTICS:
( A ) LENGTH: 41 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:16:

| | | | | |
|---|---|---|---|---|
| TCTAGAGCGG | CCGCTTATAC | YCGATCGATA | TGATARTCCG | T |

41

( 2 ) INFORMATION FOR SEQ ID NO:17:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:17:

AGGCTTCCAT AGATACCTTG TGCG     24

( 2 ) INFORMATION FOR SEQ ID NO:18:

( i ) SEQUENCE CHARACTERISTICS:
        ( A ) LENGTH: 3465 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

| | | | | | | |
|---|---|---|---|---|---|---|
| ATGGATAACA | ATCCGAACAT | CAATGAATGC | ATTCCTTATA | ATTGTTTAAG | TAACCCTGAA | 60 |
| GTAGAAGTAT | TAGGTGGAGA | AAGAATAGAA | ACTGGTTACA | CCCCAATCGA | TATTTCCTTG | 120 |
| TCGCTAACGC | AATTTCTTTT | GAGTGAATTT | GTTCCCGGTG | CTGGATTTGT | GTTAGGACTA | 180 |
| GTTGATATAA | TATGGGGAAT | TTTTGGTCCC | TCTCAATGGG | ACGCATTTCT | TGTACAAATT | 240 |
| GAACAGTTAA | TTAACCAAAG | AATAGAAGAA | TTCGCTAGGA | ACCAAGCCAT | TTCTAGATTA | 300 |
| GAAGGACTAA | GCAATCTTTA | TCAAATTTAC | GCAGAATCTT | TTAGAGAGTG | GGAAGCGGAT | 360 |
| CCTACTAATC | CAGCATTAAG | AGAAGAGATG | CGTATTCAAT | TCAATGACAT | GAACAGTGCC | 420 |
| CTTACAACCG | CTATTCCTCT | TTTTGCAGTT | CAAAATTATC | AAGTTCCTCT | TTTATCAGTA | 480 |
| TATGTTCAAG | CTGCAAATTT | ACATTTATCA | GTTTTGAGAG | ATGTTTCAGT | GTTTGGACAA | 540 |
| AGGTGGGGAT | TGATGCCGC | GACTATCAAT | AGTCGTTATA | ATGATTAAC | TAGGCTTATT | 600 |
| GGCAACTATA | CAGATTATGC | TGTACGCTGG | TACAATACGG | GATTAGAACG | TGTATGGGGA | 660 |
| CCGGATTCTA | GAGATTGGGT | AAGGTATAAT | CAATTTAGAA | GAGAATTAAC | ACTAACTGTA | 720 |
| TTAGATATCG | TTGCTCTGTT | CCCGAATTAT | GATAGTAGAA | GATATCCAAT | TCGAACAGTT | 780 |
| TCCCAATTAA | CAAGAGAAAT | TTATACAAAC | CCAGTATTAG | AAAATTTTGA | TGGTAGTTTT | 840 |
| CGAGGCTCGG | CTCAGGGCAT | AGAAGAAGT | ATTAGGAGTC | CACATTTGAT | GGATATACTT | 900 |
| AACAGTATAA | CCATCTATAC | GGATGCTCAT | AGGGGTTATT | ATTATTGGTC | AGGGCATCAA | 960 |
| ATAATGGCTT | CTCCTGTAGG | GTTTTCGGGG | CCAGAATTCA | CTTTTCCGCT | ATATGGAACT | 1020 |
| ATGGGAAATG | CAGCTCCACA | ACAACGTATT | GTTGCTCAAC | TAGGTCAGGG | CGTGTATAGA | 1080 |
| ACATTATCGT | CCACTTTATA | TAGAAGACCT | TTTAATATAG | GGATAAATAA | TCAACAACTA | 1140 |
| TCTGTTCTTG | ACGGGACAGA | ATTTGCTTAT | GGAACCTCCT | CAAATTTGCC | ATCCGCTGTA | 1200 |
| TACAGAAAAA | GCGGAACGGT | AGATTCGCTG | GATGAAATAC | CGCCACAGAA | TAACAACGTG | 1260 |
| CCACCTAGGC | AAGGATTTAG | TCATCGATTA | AGCCATGTTT | CAATGTTTCG | TTCAGGCTTT | 1320 |
| AGTAATAGTA | GTGTAAGTAT | AATAAGAGCT | CCTATGTTCT | CTTGGATACA | TCGTAGTGCT | 1380 |
| GAATTTAATA | ATATAATTCC | TTCATCACAA | ATTACACAAA | TACCTTTAAC | AAAATCTACT | 1440 |

```
AATCTTGGCT CTGGAACTTC TGTCGTTAAA GGACCAGGAT TTACAGGAGG AGATATTCTT   1500
CGAAGAACTT CACCTGGCCA GATTTCAACC TTAAGAGTAA ATATTACTGC ACCATTATCA   1560
CAAAGATATC GGGTAAGAAT TCGCTACGCT TCTACCACAA ATTTACAATT CCATACATCA   1620
ATTGACGGAA GACCTATTAA TCAGGGGAAT TTTTCAGCAA CTATGAGTAG TGGGAGTAAT   1680
TTACAGTCCG GAAGCTTTAG GACTGTAGGT TTTACTACTC CGTTTAACTT TTCAAATGGA   1740
TCAAGTGTAT TTACGTTAAG TGCTCATGTC TTCAATTCAG GCAATGAAGT TTATATAGAT   1800
CGAATTGAAT TTGTTCCGGC AGAAGTAACC TTTGAGGCAG AATATGATTT AGAAAGAGCA   1860
CAAAAGGCGG TGAATGAGCT GTTTACTTCT TCCAATCAAA TCGGGTTAAA AACAGATGTG   1920
ACGGATTATC ATATCGATCG AGTATCCAAT TTAGTTGAGT GTTTATCTGA TGAATTTTGT   1980
CTGGATGAAA AAAAGAATT  GTCCGAGAAA GTCAAACATG CGAAGCGACT TAGTGATGAG   2040
CGGAATTTAC TTCAAGATCC AAACTTTAGA GGGATCAATA GACAACTAGA CCGTGGCTGG   2100
AGAGGAAGTA CGGATATTAC CATCCAAGGA GGCGATGACG TATTCAAAGA GAATTACGTT   2160
ACGCTATTGG GTACCTTTGA TGAGTGCTAT CCAACGTATT TATATCAAAA AATAGATGAG   2220
TCGAAATTAA AAGCCTATAC CCGTTACCAA TTAAGAGGGT ATATCGAAGA TAGTCAAGAC   2280
TTAGAAATCT ATTTAATTCG CTACAATGCC AAACACGAAA CAGTAAATGT GCCAGGTACG   2340
GGTTCCTTAT GGCCGCTTTC AGCCCCAAGT CCAATCGGAA AATGTGCCCA TCATTCCCAT   2400
CATTTCTCCT TGGACATTGA TGTTGGATGT ACAGACTTAA ATGAGGACTT AGGTGTATGG   2460
GTGATATTCA AGATTAAGAC GCAAGATGGC CATGCAAGAC TAGGAAATCT AGAATTTCTC   2520
GAAGAGAAAC CATTAGTAGG AGAAGCACTA GCTCGTGTGA AAGAGCGGA  GAAAAAATGG   2580
AGAGACAAAC GTGAAAAATT GGAATGGGAA ACAAATATTG TTTATAAAGA GGCAAAAGAA   2640
TCTGTAGATG CTTTATTTGT AAACTCTCAA TATGATAGAT ACAAGCGGA  TACCAACATC   2700
GCGATGATTC ATGCGGCAGA TAAACGCGTT CATAGCATTC GAGAAGCTTA TCTGCCTGAG   2760
CTGTCTGTGA TTCCGGGTGT CAATGCGGCT ATTTTTGAAG AATTAGAAGG GCGTATTTTC   2820
ACTGCATTCT CCCTATATGA TGCGAGAAAT GTCATTAAAA ATGGTGATTT TAATAATGGC   2880
TTATCCTGCT GGAACGTGAA AGGGCATGTA GATGTAGAAG AACAAAACAA CCACCGTTCG   2940
GTCCTTGTTG TTCCGGAATG GGAAGCAGAA GTGTCACAAG AAGTTCGTGT CTGTCCGGGT   3000
CGTGGCTATA TCCTTCGTGT CACAGCGTAC AAGGAGGGAT ATGGAGAAGG TTGCGTAACC   3060
ATTCATGAGA TCGAGAACAA TACAGACGAA CTGAAGTTTA GCAACTGTGT AGAAGAGGAA   3120
GTATATCCAA ACAACACGGT AACGTGTAAT GATTATACTG CGACTCAAGA AGAATATGAG   3180
GGTACGTACA CTTCTCGTAA TCGAGGATAT GACGGAGCCT ATGAAAGCAA TTCTTCTGTA   3240
CCAGCTGATT ATGCATCAGC CTATGAAGAA AAAGCATATA CAGATGGACG AAGAGACAAT   3300
CCTTGTGAAT CTAACAGAGG ATATGGGGAT TACACACCAC TACCAGCTGG CTATGTGACA   3360
AAAGAATTAG AGTACTTCCC AGAAACCGAT AAGGTATGGA TTGAGATCGG AGAAACGGAA   3420
GGAACATTCA TCGTGGACAG CGTGGAATTA CTTCTTATGG AGGAA                  3465
```

( 2 ) INFORMATION FOR SEQ ID NO:19:

( i ) SEQUENCE CHARACTERISTICS:
        ( A ) LENGTH: 1155 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:19:

```
Met Asp Asn Asn Pro Asn Ile Asn Glu Cys Ile Pro Tyr Asn Cys Leu
 1               5                  10                  15
```

| | | | | | | | | | | | | | | |
|---|---|---|---|---|---|---|---|---|---|---|---|---|---|---|
|Ser|Asn|Pro|Glu|Val|Glu|Val|Leu|Gly|Gly|Glu|Arg|Ile|Glu|Thr|Gly|
| | | |20| | |25| | | |30| | | | |

Ser Asn Pro Glu Val Glu Val Leu Gly Gly Glu Arg Ile Glu Thr Gly
                20              25                  30

Tyr Thr Pro Ile Asp Ile Ser Leu Ser Leu Thr Gln Phe Leu Leu Ser
            35              40              45

Glu Phe Val Pro Gly Ala Gly Phe Val Leu Gly Leu Val Asp Ile Ile
        50              55              60

Trp Gly Ile Phe Gly Pro Ser Gln Trp Asp Ala Phe Leu Val Gln Ile
65              70              75                          80

Glu Gln Leu Ile Asn Gln Arg Ile Glu Glu Phe Ala Arg Asn Gln Ala
                85              90                          95

Ile Ser Arg Leu Glu Gly Leu Ser Asn Leu Tyr Gln Ile Tyr Ala Glu
            100             105             110

Ser Phe Arg Glu Trp Glu Ala Asp Pro Thr Asn Pro Ala Leu Arg Glu
            115             120             125

Glu Met Arg Ile Gln Phe Asn Asp Met Asn Ser Ala Leu Thr Thr Ala
            130             135             140

Ile Pro Leu Phe Ala Val Gln Asn Tyr Gln Val Pro Leu Leu Ser Val
145             150             155                         160

Tyr Val Gln Ala Ala Asn Leu His Leu Ser Val Leu Arg Asp Val Ser
                165             170             175

Val Phe Gly Gln Arg Trp Gly Phe Asp Ala Ala Thr Ile Asn Ser Arg
            180             185             190

Tyr Asn Asp Leu Thr Arg Leu Ile Gly Asn Tyr Thr Asp Tyr Ala Val
            195             200             205

Arg Trp Tyr Asn Thr Gly Leu Glu Arg Val Trp Gly Pro Asp Ser Arg
    210             215             220

Asp Trp Val Arg Tyr Asn Gln Phe Arg Arg Glu Leu Thr Leu Thr Val
225             230             235                         240

Leu Asp Ile Val Ala Leu Phe Pro Asn Tyr Asp Ser Arg Arg Tyr Pro
            245             250             255

Ile Arg Thr Val Ser Gln Leu Thr Arg Glu Ile Tyr Thr Asn Pro Val
            260             265             270

Leu Glu Asn Phe Asp Gly Ser Phe Arg Gly Ser Ala Gln Gly Ile Glu
    275             280             285

Arg Ser Ile Arg Ser Pro His Leu Met Asp Ile Leu Asn Ser Ile Thr
    290             295             300

Ile Tyr Thr Asp Ala His Arg Gly Tyr Tyr Tyr Trp Ser Gly His Gln
305             310             315                         320

Ile Met Ala Ser Pro Val Gly Phe Ser Gly Pro Glu Phe Thr Phe Pro
            325             330             335

Leu Tyr Gly Thr Met Gly Asn Ala Ala Pro Gln Gln Arg Ile Val Ala
            340             345             350

Gln Leu Gly Gln Gly Val Tyr Arg Thr Leu Ser Ser Thr Leu Tyr Arg
            355             360             365

Arg Pro Phe Asn Ile Gly Ile Asn Asn Gln Gln Leu Ser Val Leu Asp
    370             375             380

Gly Thr Glu Phe Ala Tyr Gly Thr Ser Ser Asn Leu Pro Ser Ala Val
385             390             395                         400

Tyr Arg Lys Ser Gly Thr Val Asp Ser Leu Asp Glu Ile Pro Pro Gln
            405             410             415

Asn Asn Asn Val Pro Pro Arg Gln Gly Phe Ser His Arg Leu Ser His
            420             425             430

Val Ser Met Phe Arg Ser Gly Phe Ser Asn Ser Ser Val Ser Ile Ile
            435             440             445

Arg Ala Pro Met Phe Ser Trp Ile His Arg Ser Ala Glu Phe Asn Asn

|     |     |     |     |     |     |     |     |     |     |     |     |     |     |     |     |
|---|---|---|---|---|---|---|---|---|---|---|---|---|---|---|---|
| Ile | Ile | Pro | Ser | Ser | Gln | Ile | Thr | Gln | Ile | Pro | Leu | Thr | Lys | Ser | Thr |
| 465 |     |     |     |     | 470 |     |     |     | 475 |     |     |     |     |     | 480 |
| Asn | Leu | Gly | Ser | Gly | Thr | Ser | Val | Val | Lys | Gly | Pro | Gly | Phe | Thr | Gly |
|     |     |     |     | 485 |     |     |     |     | 490 |     |     |     |     | 495 |     |
| Gly | Asp | Ile | Leu | Arg | Arg | Thr | Ser | Pro | Gly | Gln | Ile | Ser | Thr | Leu | Arg |
|     |     |     | 500 |     |     |     |     | 505 |     |     |     |     | 510 |     |     |
| Val | Asn | Ile | Thr | Ala | Pro | Leu | Ser | Gln | Arg | Tyr | Arg | Val | Arg | Ile | Arg |
|     |     |     | 515 |     |     |     | 520 |     |     |     |     | 525 |     |     |     |
| Tyr | Ala | Ser | Thr | Thr | Asn | Leu | Gln | Phe | His | Thr | Ser | Ile | Asp | Gly | Arg |
|     |     | 530 |     |     |     | 535 |     |     |     |     | 540 |     |     |     |     |
| Pro | Ile | Asn | Gln | Gly | Asn | Phe | Ser | Ala | Thr | Met | Ser | Ser | Gly | Ser | Asn |
| 545 |     |     |     |     | 550 |     |     |     |     | 555 |     |     |     |     | 560 |
| Leu | Gln | Ser | Gly | Ser | Phe | Arg | Thr | Val | Gly | Phe | Thr | Thr | Pro | Phe | Asn |
|     |     |     |     | 565 |     |     |     |     | 570 |     |     |     |     | 575 |     |
| Phe | Ser | Asn | Gly | Ser | Ser | Val | Phe | Thr | Leu | Ser | Ala | His | Val | Phe | Asn |
|     |     |     | 580 |     |     |     |     | 585 |     |     |     |     | 590 |     |     |
| Ser | Gly | Asn | Glu | Val | Tyr | Ile | Asp | Arg | Ile | Glu | Phe | Val | Pro | Ala | Glu |
|     |     | 595 |     |     |     | 600 |     |     |     |     | 605 |     |     |     |     |
| Val | Thr | Phe | Glu | Ala | Glu | Tyr | Asp | Leu | Glu | Arg | Ala | Gln | Lys | Ala | Val |
|     | 610 |     |     |     |     | 615 |     |     |     |     | 620 |     |     |     |     |
| Asn | Glu | Leu | Phe | Thr | Ser | Ser | Asn | Gln | Ile | Gly | Leu | Lys | Thr | Asp | Val |
| 625 |     |     |     |     | 630 |     |     |     |     | 635 |     |     |     |     | 640 |
| Thr | Asp | Tyr | His | Ile | Asp | Arg | Val | Ser | Asn | Leu | Val | Glu | Cys | Leu | Ser |
|     |     |     |     | 645 |     |     |     |     | 650 |     |     |     |     | 655 |     |
| Asp | Glu | Phe | Cys | Leu | Asp | Glu | Lys | Lys | Glu | Leu | Ser | Glu | Lys | Val | Lys |
|     |     |     | 660 |     |     |     |     | 665 |     |     |     |     | 670 |     |     |
| His | Ala | Lys | Arg | Leu | Ser | Asp | Glu | Arg | Asn | Leu | Leu | Gln | Asp | Pro | Asn |
|     |     | 675 |     |     |     |     | 680 |     |     |     |     | 685 |     |     |     |
| Phe | Arg | Gly | Ile | Asn | Arg | Gln | Leu | Asp | Arg | Gly | Trp | Arg | Gly | Ser | Thr |
|     | 690 |     |     |     |     | 695 |     |     |     |     | 700 |     |     |     |     |
| Asp | Ile | Thr | Ile | Gln | Gly | Gly | Asp | Asp | Val | Phe | Lys | Glu | Asn | Tyr | Val |
| 705 |     |     |     |     | 710 |     |     |     |     | 715 |     |     |     |     | 720 |
| Thr | Leu | Leu | Gly | Thr | Phe | Asp | Glu | Cys | Tyr | Pro | Thr | Tyr | Leu | Tyr | Gln |
|     |     |     |     | 725 |     |     |     |     | 730 |     |     |     |     | 735 |     |
| Lys | Ile | Asp | Glu | Ser | Lys | Leu | Lys | Ala | Tyr | Thr | Arg | Tyr | Gln | Leu | Arg |
|     |     |     | 740 |     |     |     |     | 745 |     |     |     |     | 750 |     |     |
| Gly | Tyr | Ile | Glu | Asp | Ser | Gln | Asp | Leu | Glu | Ile | Tyr | Leu | Ile | Arg | Tyr |
|     |     | 755 |     |     |     |     | 760 |     |     |     |     | 765 |     |     |     |
| Asn | Ala | Lys | His | Glu | Thr | Val | Asn | Val | Pro | Gly | Thr | Gly | Ser | Leu | Trp |
| 770 |     |     |     |     | 775 |     |     |     |     | 780 |     |     |     |     |     |
| Pro | Leu | Ser | Ala | Pro | Ser | Pro | Ile | Gly | Lys | Cys | Ala | His | His | Ser | His |
| 785 |     |     |     |     | 790 |     |     |     |     | 795 |     |     |     |     | 800 |
| His | Phe | Ser | Leu | Asp | Ile | Asp | Val | Gly | Cys | Thr | Asp | Leu | Asn | Glu | Asp |
|     |     |     |     | 805 |     |     |     |     | 810 |     |     |     |     | 815 |     |
| Leu | Gly | Val | Trp | Val | Ile | Phe | Lys | Ile | Lys | Thr | Gln | Asp | Gly | His | Ala |
|     |     |     | 820 |     |     |     |     | 825 |     |     |     |     | 830 |     |     |
| Arg | Leu | Gly | Asn | Leu | Glu | Phe | Leu | Glu | Glu | Lys | Pro | Leu | Val | Gly | Glu |
|     |     | 835 |     |     |     |     | 840 |     |     |     |     | 845 |     |     |     |
| Ala | Leu | Ala | Arg | Val | Lys | Arg | Ala | Glu | Lys | Lys | Trp | Arg | Asp | Lys | Arg |
|     | 850 |     |     |     |     | 855 |     |     |     |     | 860 |     |     |     |     |
| Glu | Lys | Leu | Glu | Trp | Glu | Thr | Asn | Ile | Val | Tyr | Lys | Glu | Ala | Lys | Glu |
| 865 |     |     |     |     | 870 |     |     |     |     | 875 |     |     |     |     | 880 |
| Ser | Val | Asp | Ala | Leu | Phe | Val | Asn | Ser | Gln | Tyr | Asp | Arg | Leu | Gln | Ala |
|     |     |     |     | 885 |     |     |     |     | 890 |     |     |     |     | 895 |     |

| | | | | | | | | | | | | | |
|---|---|---|---|---|---|---|---|---|---|---|---|---|---|
| Asp | Thr | Asn | Ile 900 | Ala | Met | Ile | His 905 | Ala | Asp | Lys | Arg 910 | Val | His | Ser |
| Ile | Arg | Glu 915 | Ala | Tyr | Leu | Pro 920 | Glu | Leu | Ser | Val | Ile 925 | Pro | Gly | Val | Asn |
| Ala | Ala | Ile 930 | Phe | Glu | Glu | Leu 935 | Glu | Gly | Arg | Ile | Phe 940 | Thr | Ala | Phe | Ser |
| Leu 945 | Tyr | Asp | Ala | Arg | Asn 950 | Val | Ile | Lys | Asn | Gly 955 | Asp | Phe | Asn | Asn | Gly 960 |
| Leu | Ser | Cys | Trp | Asn 965 | Val | Lys | Gly | His | Val 970 | Asp | Val | Glu | Glu | Gln 975 | Asn |
| Asn | His | Arg | Ser 980 | Val | Leu | Val | Val | Pro 985 | Glu | Trp | Glu | Ala | Glu 990 | Val | Ser |
| Gln | Glu | Val 995 | Arg | Val | Cys | Pro | Gly 1000 | Arg | Gly | Tyr | Ile | Leu 1005 | Arg | Val | Thr |
| Ala | Tyr | Lys 1010 | Glu | Gly | Tyr | Gly 1015 | Glu | Gly | Cys | Val | Thr 1020 | Ile | His | Glu | Ile |
| Glu 1025 | Asn | Asn | Thr | Asp | Glu 1030 | Leu | Lys | Phe | Ser | Asn 1035 | Cys | Val | Glu | Glu 1040 |
| Val | Tyr | Pro | Asn | Asn 1045 | Thr | Val | Thr | Cys | Asn 1050 | Asp | Tyr | Thr | Ala | Thr | Gln 1055 |
| Glu | Glu | Tyr | Glu 1060 | Gly | Thr | Tyr | Thr | Ser 1065 | Arg | Asn | Arg | Gly | Tyr 1070 | Asp | Gly |
| Ala | Tyr | Glu 1075 | Ser | Asn | Ser | Ser | Val 1080 | Pro | Ala | Asp | Tyr | Ala 1085 | Ser | Ala | Tyr |
| Glu | Glu | Lys 1090 | Ala | Tyr | Thr | Asp 1095 | Gly | Arg | Arg | Asp | Asn 1100 | Pro | Cys | Glu | Ser |
| Asn 1105 | Arg | Gly | Tyr | Gly | Asp 1110 | Tyr | Thr | Pro | Leu | Pro 1115 | Ala | Gly | Tyr | Val | Thr 1120 |
| Lys | Glu | Leu | Glu | Tyr 1125 | Phe | Pro | Glu | Thr | Asp 1130 | Lys | Val | Trp | Ile | Glu 1135 | Ile |
| Gly | Glu | Thr | Glu 1140 | Gly | Thr | Phe | Ile | Val 1145 | Asp | Ser | Val | Glu | Leu 1150 | Leu | Leu |
| Met | Glu | Glu 1155 |

( 2 ) INFORMATION FOR SEQ ID NO:20:

( i ) SEQUENCE CHARACTERISTICS:
        ( A ) LENGTH: 3450 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

```
ATGGATAACA ATCCGAACAT CAATGAATGC ATTCCTTATA ATTGTTTAAG TAACCCTGAA        60
GTAGAAGTAT TAGGTGGAGA AAGAATAGAA ACTGGTTACA CCCCAATCGA TATTTCCTTG       120
TCGCTAACGC AATTTCTTTT GAGTGAATTT GTTCCCGGTG CTGGATTTGT GTTAGGACTA       180
GTTGATATAA TATGGGGAAT TTTTGGTCCC TCTCAATGGG ACGCATTTCT TGTACAAATT       240
GAACAGTTAA TTAACCAAAG AATAGAAGAA TTCGCTAGGA ACCAAGCCAT TTCTAGATTA       300
GAAGGACTAA GCAATCTTTA TCAAATTTAC GCAGAATCTT TTAGAGAGTG GGAAGCGGAT       360
CTTAATAATG CACAATTAAG GGAAGATGTG CGTATTCGAT TGCTAATAC AGACGACGCT        420
TTAATAACAG CAATAAATAA TTTTACACTT ACAAGTTTTG AAATCCCTCT TTTATCGGTC       480
TATGTTCAAG CGGCGAATTT ACATTTATCA CTATTAAGAG ACGCTGTATC GTTTGGGCAG       540
GGTTGGGGAC TGGATATAGC TACTGTTAAT AATCATTATA ATAGATTAAT AAATCTTATT       600
```

```
CATAGATATA CGAAACATTG TTTGGACACA TACAATCAAG GATTAGAAAA CTTAAGAGGT    660
ACTAATACTC GACAATGGGC AAGATTCAAT CAGTTTAGGA GAGATTTAAC ACTTACTGTA    720
TTAGATATCG TTGCTCTTTT TCCGAACTAC GATGTTAGAA CATATCCAAT TCAAACGTCA    780
TCCCAATTAA CAAGGGAAAT TTATACAAGT TCAGTAATTG AGGATTCTCC AGTTCTGCT     840
AATATACCTA ATGGTTTTAA TAGGGCGGAA TTTGGAGTTA GACCGCCCCA TCTTATGGAC    900
TTTATGAATT CTTTGTTTGT AACTGCAGAG ACTGTTAGAA GTCAAACTGT GTGGGGAGGA    960
CACTTAGTTA GTTCACGAAA TACGGCTGGT AACCGTATAA ATTTCCCTAG TTACGGGGTC   1020
TTCAATCCTG GTGGCGCCAT TTGGATTGCA GATGAGGATC CACGTCCTTT TTATCGGACA   1080
TTATCAGATC CTGTTTTTGT CCGAGGAGGA TTTGGGAATC CTCATTATGT ACTGGGGCTT   1140
AGGGGAGTAG CATTTCAACA AACTGGTACG AACCACACCC GAACATTTAG AAATAGTGGG   1200
ACCATAGATT CTCTAGATGA ATCCCACCT CAGGATAATA GTGGGCACC TTGGAATGAT      1260
TATAGTCATG TATTAAATCA TGTTACATTT GTACGATGGC CAGGTGAGAT TCAGGAAGT    1320
GATTCATGGA GAGCTCCAAT GTTTCTTGG ACGCACCGTA GTGCAACCCC TACAAATACA    1380
ATTGATCCGG AGAGGATTAC TCAAATACCA TTGGTAAAAG CACATACACT TCAGTCAGGT   1440
ACTACTGTTG TAAGAGGGCC CGGGTTTACG GGAGGAGATA TTCTTCGACG AACAAGTGGA   1500
GGACCATTTG CTTATACTAT TGTTAATATA AATGGGCAAT TACCCCAAAG GTATCGTGCA   1560
AGAATACGCT ATGCCTCTAC TACAAATCTA GAATTTACG TAACGGTTGC AGGTGAACGG    1620
ATTTTTGCTG GTCAATTTAA CAAAACAATG GATACCGGTG ACCCATTAAC ATTCCAATCT   1680
TTTAGTTACG CAACTATTAA TACAGCTTTT ACATTCCCAA TGAGCCAGAG TAGTTTCACA   1740
GTAGGTGCTG ATACTTTTAG TTCAGGGAAT GAAGTTTATA TAGACAGATT TGAATTGATT   1800
CCAGTTACTG CAACATTTGA AGCAGAATAT GATTTAGAAA GAGCACAAAA GGCGGTGAAT   1860
GCGCTGTTTA CTTCTATAAA CCAAATAGGG ATAAAACAG ATGTGACGGA TTATCATATC    1920
GATCGAGTAT CCAATTTAGT TGAGTGTTTA TCTGATGAAT TTTGTCTGGA TGAAAAAAAA   1980
GAATTGTCCG AGAAAGTCAA ACATGCGAAG CGACTTAGTG ATGAGCGGAA TTTACTTCAA   2040
GATCCAAACT TTAGAGGGAT CAATAGACAA CTAGACCGTG GCTGGAGAGG AAGTACGGAT   2100
ATTACCATCC AAGGAGGCGA TGACGTATTC AAAGAGAATT ACGTTACGCT ATTGGGTACC   2160
TTTGATGAGT GCTATCCAAC GTATTTATAT CAAAAAATAG ATGAGTCGAA ATTAAAAGCC   2220
TATACCCGTT ACCAATTAAG AGGGTATATC GAAGATAGTC AAGACTTAGA AATCTATTTA   2280
ATTCGCTACA ATGCCAAACA CGAAACAGTA AATGTGCCAG GTACGGGTTC CTTATGGCCG   2340
CTTTCAGCCC CAAGTCCAAT CGGAAAATGT GCCCATCATT CCCATCATTT CTCCTTGGAC   2400
ATTGATGTTG GATGTACAGA CTTAAATGAG GACTTAGGTG TATGGGTGAT ATTCAAGATT   2460
AAGACGCAAG ATGGCCATGC AAGACTAGGA AATCTAGAAT TTCTCGAAGA GAAACCATTA   2520
GTAGGAGAAG CACTAGCTCG TGTGAAAAGA GCGGAGAAAA ATGGAGAGA CAAACGTGAA    2580
AAATTGGAAT GGGAAACAAA TATTGTTTAT AAAGAGGCAA AGAATCTGT AGATGCTTTA    2640
TTTGTAAACT CTCAATATGA TAGATTACAA GCGGATACCA ACATCGCGAT GATTCATGCG   2700
GCAGATAAAC GCGTTCATAG CATTCGAGAA GCTTATCTGC CTGAGCTGTC TGTGATTCCG   2760
GGTGTCAATG CGGCTATTTT TGAAGAATTA GAAGGGCGTA TTTTCACTGC ATTCTCCCTA   2820
TATGATGCGA GAAATGTCAT TAAAAATGGT GATTTAATA ATGGCTTATC CTGCTGGAAC    2880
GTGAAGGGC ATGTAGATGT AGAAGAACAA AACAACCACC GTTCGGTCCT TGTTGTTCCG    2940
GAATGGGAAG CAGAAGTGTC ACAAGAAGTT CGTGTCTGTC CGGGTCGTGG CTATATCCTT   3000
CGTGTCACAG CGTACAAGGA GGGATATGGA GAAGGTTGCG TAACCATTCA TGAGATCGAG   3060
```

```
AACAATACAG ACGAACTGAA GTTTAGCAAC TGTGTAGAAG AGGAAGTATA TCCAAACAAC      3120

ACGGTAACGT GTAATGATTA TACTGCGACT CAAGAAGAAT ATGAGGGTAC GTACACTTCT      3180

CGTAATCGAG GATATGACGG AGCCTATGAA AGCAATTCTT CTGTACCAGC TGATTATGCA      3240

TCAGCCTATG AAGAAAAAGC ATATACAGAT GGACGAAGAG ACAATCCTTG TGAATCTAAC      3300

AGAGGATATG GGATTACAC ACCACTACCA GCTGGCTATG TGACAAAAGA ATTAGAGTAC       3360

TTCCCAGAAA CCGATAAGGT ATGGATTGAG ATCGGAGAAA CGGAAGGAAC ATTCATCGTG      3420

GACAGCGTGG AATTACTTCT TATGGAGGAA                                      3450
```

(2) INFORMATION FOR SEQ ID NO:21:

(i) SEQUENCE CHARACTERISTICS:
        (A) LENGTH: 1150 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

```
Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Leu Asn Asn Ala Gln Leu Arg Glu
    115                 120                 125

Asp Val Arg Ile Arg Phe Ala Asn Thr Asp Asp Ala Leu Ile Thr Ala
130                 135                 140

Ile Asn Asn Phe Thr Leu Thr Ser Phe Glu Ile Pro Leu Leu Ser Val
145                 150                 155                 160

Tyr Val Gln Ala Ala Asn Leu His Leu Ser Leu Leu Arg Asp Ala Val
                165                 170                 175

Ser Phe Gly Gln Gly Trp Gly Leu Asp Ile Ala Thr Val Asn Asn His
            180                 185                 190

Tyr Asn Arg Leu Ile Asn Leu Ile His Arg Tyr Thr Lys His Cys Leu
    195                 200                 205

Asp Thr Tyr Asn Gln Gly Leu Glu Asn Leu Arg Gly Thr Asn Thr Arg
210                 215                 220

Gln Trp Ala Arg Phe Asn Gln Phe Arg Arg Asp Leu Thr Leu Thr Val
225                 230                 235                 240

Leu Asp Ile Val Ala Leu Phe Pro Asn Tyr Asp Val Arg Thr Tyr Pro
                245                 250                 255

Ile Gln Thr Ser Ser Gln Leu Thr Arg Glu Ile Tyr Thr Ser Ser Val
            260                 265                 270

Ile Glu Asp Ser Pro Val Ser Ala Asn Ile Pro Asn Gly Phe Asn Arg
    275                 280                 285

Ala Glu Phe Gly Val Arg Pro Pro His Leu Met Asp Phe Met Asn Ser
290                 295                 300
```

| | | | | | | | | | | | | | | | |
|---|---|---|---|---|---|---|---|---|---|---|---|---|---|---|---|
| Leu | Phe | Val | Thr | Ala | Glu | Thr | Val | Arg | Ser | Gln | Thr | Val | Trp | Gly | Gly |
| 305 | | | | | 310 | | | | 315 | | | | | | 320 |
| His | Leu | Val | Ser | Ser | Arg | Asn | Thr | Ala | Gly | Asn | Arg | Ile | Asn | Phe | Pro |
| | | | | 325 | | | | | 330 | | | | | | 335 |
| Ser | Tyr | Gly | Val | Phe | Asn | Pro | Gly | Gly | Ala | Ile | Trp | Ile | Ala | Asp | Glu |
| | | | 340 | | | | | 345 | | | | | 350 | | |
| Asp | Pro | Arg | Pro | Phe | Tyr | Arg | Thr | Leu | Ser | Asp | Pro | Val | Phe | Val | Arg |
| | | 355 | | | | 360 | | | | | 365 | | | | |
| Gly | Gly | Phe | Gly | Asn | Pro | His | Tyr | Val | Leu | Gly | Leu | Arg | Gly | Val | Ala |
| | 370 | | | | | 375 | | | | | 380 | | | | |
| Phe | Gln | Gln | Thr | Gly | Thr | Asn | His | Thr | Arg | Thr | Phe | Arg | Asn | Ser | Gly |
| 385 | | | | | 390 | | | | | 395 | | | | | 400 |
| Thr | Ile | Asp | Ser | Leu | Asp | Glu | Ile | Pro | Pro | Gln | Asp | Asn | Ser | Gly | Ala |
| | | | | 405 | | | | | 410 | | | | | 415 | |
| Pro | Trp | Asn | Asp | Tyr | Ser | His | Val | Leu | Asn | His | Val | Thr | Phe | Val | Arg |
| | | | 420 | | | | | 425 | | | | | 430 | | |
| Trp | Pro | Gly | Glu | Ile | Ser | Gly | Ser | Asp | Ser | Trp | Arg | Ala | Pro | Met | Phe |
| | | | 435 | | | | | 440 | | | | | 445 | | |
| Ser | Trp | Thr | His | Arg | Ser | Ala | Thr | Pro | Thr | Asn | Thr | Ile | Asp | Pro | Glu |
| | 450 | | | | | 455 | | | | | 460 | | | | |
| Arg | Ile | Thr | Gln | Ile | Pro | Leu | Val | Lys | Ala | His | Thr | Leu | Gln | Ser | Gly |
| 465 | | | | | 470 | | | | | 475 | | | | | 480 |
| Thr | Thr | Val | Val | Arg | Gly | Pro | Gly | Phe | Thr | Gly | Gly | Asp | Ile | Leu | Arg |
| | | | | 485 | | | | | 490 | | | | | 495 | |
| Arg | Thr | Ser | Gly | Gly | Pro | Phe | Ala | Tyr | Thr | Ile | Val | Asn | Ile | Asn | Gly |
| | | | 500 | | | | | 505 | | | | | 510 | | |
| Gln | Leu | Pro | Gln | Arg | Tyr | Arg | Ala | Arg | Ile | Arg | Tyr | Ala | Ser | Thr | Thr |
| | | 515 | | | | | 520 | | | | | 525 | | | |
| Asn | Leu | Arg | Ile | Tyr | Val | Thr | Val | Ala | Gly | Glu | Arg | Ile | Phe | Ala | Gly |
| | 530 | | | | | 535 | | | | | 540 | | | | |
| Gln | Phe | Asn | Lys | Thr | Met | Asp | Thr | Gly | Asp | Pro | Leu | Thr | Phe | Gln | Ser |
| 545 | | | | | 550 | | | | | 555 | | | | | 560 |
| Phe | Ser | Tyr | Ala | Thr | Ile | Asn | Thr | Ala | Phe | Thr | Phe | Pro | Met | Ser | Gln |
| | | | | 565 | | | | | 570 | | | | | 575 | |
| Ser | Ser | Phe | Thr | Val | Gly | Ala | Asp | Thr | Phe | Ser | Ser | Gly | Asn | Glu | Val |
| | | | 580 | | | | | 585 | | | | | 590 | | |
| Tyr | Ile | Asp | Arg | Phe | Glu | Leu | Ile | Pro | Val | Thr | Ala | Thr | Phe | Glu | Ala |
| | | | 595 | | | | | 600 | | | | | 605 | | |
| Glu | Tyr | Asp | Leu | Glu | Arg | Ala | Gln | Lys | Ala | Val | Asn | Ala | Leu | Phe | Thr |
| | 610 | | | | | 615 | | | | | 620 | | | | |
| Ser | Ile | Asn | Gln | Ile | Gly | Ile | Lys | Thr | Asp | Val | Thr | Asp | Tyr | His | Ile |
| 625 | | | | | 630 | | | | | 635 | | | | | 640 |
| Asp | Arg | Val | Ser | Asn | Leu | Val | Glu | Cys | Leu | Ser | Asp | Glu | Phe | Cys | Leu |
| | | | | 645 | | | | | 650 | | | | | 655 | |
| Asp | Glu | Lys | Lys | Glu | Leu | Ser | Glu | Lys | Val | Lys | His | Ala | Lys | Arg | Leu |
| | | | 660 | | | | | 665 | | | | | 670 | | |
| Ser | Asp | Glu | Arg | Asn | Leu | Leu | Gln | Asp | Pro | Asn | Phe | Arg | Gly | Ile | Asn |
| | | | 675 | | | | | 680 | | | | | 685 | | |
| Arg | Gln | Leu | Asp | Arg | Gly | Trp | Arg | Gly | Ser | Thr | Asp | Ile | Thr | Ile | Gln |
| | 690 | | | | | 695 | | | | | 700 | | | | |
| Gly | Gly | Asp | Asp | Val | Phe | Lys | Glu | Asn | Tyr | Val | Thr | Leu | Leu | Gly | Thr |
| 705 | | | | | 710 | | | | | 715 | | | | | 720 |
| Phe | Asp | Glu | Cys | Tyr | Pro | Thr | Tyr | Leu | Tyr | Gln | Lys | Ile | Asp | Glu | Ser |
| | | | | 725 | | | | | 730 | | | | | 735 | |
| Lys | Leu | Lys | Ala | Tyr | Thr | Arg | Tyr | Gln | Leu | Arg | Gly | Tyr | Ile | Glu | Asp |

|     |     |     |     |     | 740 |     |     |     |     | 745 |     |     |     |     | 750 |
| --- | --- | --- | --- | --- | --- | --- | --- | --- | --- | --- | --- | --- | --- | --- | --- |
| Ser | Gln | Asp | Leu | Glu | Ile | Tyr | Leu | Ile | Arg | Tyr | Asn | Ala | Lys | His | Glu |
|     |     |     |     | 755 |     |     |     | 760 |     |     |     | 765 |     |     |     |
| Thr | Val | Asn | Val | Pro | Gly | Thr | Gly | Ser | Leu | Trp | Pro | Leu | Ser | Ala | Pro |
|     |     | 770 |     |     |     | 775 |     |     |     |     | 780 |     |     |     |     |
| Ser | Pro | Ile | Gly | Lys | Cys | Ala | His | Ser | His | His | Phe | Ser | Leu | Asp |
| 785 |     |     |     |     | 790 |     |     |     |     | 795 |     |     |     | 800 |
| Ile | Asp | Val | Gly | Cys | Thr | Asp | Leu | Asn | Glu | Asp | Leu | Gly | Val | Trp | Val |
|     |     |     |     | 805 |     |     |     |     | 810 |     |     |     |     | 815 |     |
| Ile | Phe | Lys | Ile | Lys | Thr | Gln | Asp | Gly | His | Ala | Arg | Leu | Gly | Asn | Leu |
|     |     |     | 820 |     |     |     |     | 825 |     |     |     |     | 830 |     |     |
| Glu | Phe | Leu | Glu | Glu | Lys | Pro | Leu | Val | Gly | Glu | Ala | Leu | Ala | Arg | Val |
|     |     | 835 |     |     |     |     | 840 |     |     |     |     | 845 |     |     |     |
| Lys | Arg | Ala | Glu | Lys | Lys | Trp | Arg | Asp | Lys | Arg | Glu | Lys | Leu | Glu | Trp |
|     | 850 |     |     |     |     |     | 855 |     |     |     |     | 860 |     |     |     |
| Glu | Thr | Asn | Ile | Val | Tyr | Lys | Glu | Ala | Lys | Glu | Ser | Val | Asp | Ala | Leu |
| 865 |     |     |     |     |     | 870 |     |     |     |     | 875 |     |     |     | 880 |
| Phe | Val | Asn | Ser | Gln | Tyr | Asp | Arg | Leu | Gln | Ala | Asp | Thr | Asn | Ile | Ala |
|     |     |     |     | 885 |     |     |     |     | 890 |     |     |     |     | 895 |     |
| Met | Ile | His | Ala | Ala | Asp | Lys | Arg | Val | His | Ser | Ile | Arg | Glu | Ala | Tyr |
|     |     |     |     | 900 |     |     |     |     | 905 |     |     |     |     | 910 |     |
| Leu | Pro | Glu | Leu | Ser | Val | Ile | Pro | Gly | Val | Asn | Ala | Ala | Ile | Phe | Glu |
|     |     |     |     | 915 |     |     |     |     | 920 |     |     |     |     | 925 |     |
| Glu | Leu | Glu | Gly | Arg | Ile | Phe | Thr | Ala | Phe | Ser | Leu | Tyr | Asp | Ala | Arg |
|     |     | 930 |     |     |     |     | 935 |     |     |     |     | 940 |     |     |     |
| Asn | Val | Ile | Lys | Asn | Gly | Asp | Phe | Asn | Asn | Gly | Leu | Ser | Cys | Trp | Asn |
| 945 |     |     |     |     |     | 950 |     |     |     |     | 955 |     |     |     | 960 |
| Val | Lys | Gly | His | Val | Asp | Val | Glu | Glu | Gln | Asn | Asn | His | Arg | Ser | Val |
|     |     |     |     | 965 |     |     |     |     | 970 |     |     |     |     | 975 |     |
| Leu | Val | Val | Pro | Glu | Trp | Glu | Ala | Glu | Val | Ser | Gln | Val | Arg | Val |
|     |     |     | 980 |     |     |     |     | 985 |     |     |     |     | 990 |     |
| Cys | Pro | Gly | Arg | Gly | Tyr | Ile | Leu | Arg | Val | Thr | Ala | Tyr | Lys | Glu | Gly |
|     |     |     | 995 |     |     |     |     | 1000 |     |     |     |     | 1005 |     |     |
| Tyr | Gly | Glu | Gly | Cys | Val | Thr | Ile | His | Glu | Ile | Glu | Asn | Asn | Thr | Asp |
|     |     | 1010 |     |     |     |     | 1015 |     |     |     |     | 1020 |     |     |     |
| Glu | Leu | Lys | Phe | Ser | Asn | Cys | Val | Glu | Glu | Val | Tyr | Pro | Asn | Asn |
| 1025 |     |     |     |     | 1030 |     |     |     |     | 1035 |     |     |     | 1040 |
| Thr | Val | Thr | Cys | Asn | Asp | Tyr | Thr | Ala | Thr | Gln | Glu | Glu | Tyr | Glu | Gly |
|     |     |     |     | 1045 |     |     |     |     | 1050 |     |     |     |     | 1055 |     |
| Thr | Tyr | Thr | Ser | Arg | Asn | Arg | Gly | Tyr | Asp | Gly | Ala | Tyr | Glu | Ser | Asn |
|     |     |     |     | 1060 |     |     |     |     | 1065 |     |     |     |     | 1070 |     |
| Ser | Ser | Val | Pro | Ala | Asp | Tyr | Ala | Ser | Ala | Tyr | Glu | Glu | Lys | Ala | Tyr |
|     |     |     | 1075 |     |     |     |     | 1080 |     |     |     |     | 1085 |     |     |
| Thr | Asp | Gly | Arg | Arg | Asp | Asn | Pro | Cys | Glu | Ser | Asn | Arg | Gly | Tyr | Gly |
|     |     | 1090 |     |     |     |     | 1095 |     |     |     |     | 1100 |     |     |     |
| Asp | Tyr | Thr | Pro | Leu | Pro | Ala | Gly | Tyr | Val | Thr | Lys | Glu | Leu | Glu | Tyr |
| 1105 |     |     |     |     | 1110 |     |     |     |     | 1115 |     |     |     | 1120 |
| Phe | Pro | Glu | Thr | Asp | Lys | Val | Trp | Ile | Glu | Ile | Gly | Glu | Thr | Glu | Gly |
|     |     |     |     | 1125 |     |     |     |     | 1130 |     |     |     |     | 1135 |     |
| Thr | Phe | Ile | Val | Asp | Ser | Val | Glu | Leu | Leu | Leu | Met | Glu | Glu |
|     |     |     |     | 1140 |     |     |     | 1145 |     |     |     |     | 1150 |

( 2 ) INFORMATION FOR SEQ ID NO:22:

( i ) SEQUENCE CHARACTERISTICS:
        ( A ) LENGTH: 3444 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:22:

| | | | | | | |
|---|---|---|---|---|---|---|
| ATGGAGAATA | ATATTCAAAA | TCAATGCGTA | CCTTACAATT | GTTTAAATAA | TCCTGAAGTA | 60 |
| GAAATATTAA | ATGAAGAAAG | AAGTACTGGC | AGATTACCGT | TAGATATATC | CTTATCGCTT | 120 |
| ACACGTTTCC | TTTTGAGTGA | ATTTGTTCCA | GGTGTGGGAG | TTGCGTTTGG | ATTATTTGAT | 180 |
| TTAATATGGG | GTTTTATAAC | TCCTTCTGAT | TGGAGCTTAT | TTCTTTTACA | GATTGAACAA | 240 |
| TTGATTGAGC | AAAGAATAGA | AACATTGGAA | AGGAACCGGG | CAATTACTAC | ATTACGAGGG | 300 |
| TTAGCAGATA | GCTATGAAAT | TTATATTGAA | GCACTAAGAG | AGTGGGAAGC | AAATCCTAAT | 360 |
| AATGCACAAT | TAAGGGAAGA | TGTGCGTATT | CGATTTGCTA | ATACAGACGA | CGCTTTAATA | 420 |
| ACAGCAATAA | ATAATTTTAC | ACTTACAAGT | TTTGAAATCC | CTCTTTTATC | GGTCTATGTT | 480 |
| CAAGCGGCGA | ATTTACATTT | ATCACTATTA | AGAGACGCTG | TATCGTTTGG | GCAGGGTTGG | 540 |
| GGACTGGATA | TAGCTACTGT | TAATAATCAT | TATAATAGAT | TAATAAATCT | TATTCATAGA | 600 |
| TATACGAAAC | ATTGTTTGGA | CACATACAAT | CAAGGATTAG | AAAACTTAAG | AGGTACTAAT | 660 |
| ACTCGACAAT | GGGCAAGATT | CAATCAGTTT | AGGAGAGATT | TAACACTTAC | TGTATTAGAT | 720 |
| ATCGTTGCTC | TTTTTCCGAA | CTACGATGTT | AGAACATATC | CAATTCAAAC | GTCATCCCAA | 780 |
| TTAACAAGGG | AAATTTATAC | AAGTTCAGTA | ATTGAGGATT | CTCCAGTTTC | TGCTAATATA | 840 |
| CCTAATGGTT | TTAATAGGGC | GGAATTTGGA | GTTAGACCGC | CCCATCTTAT | GGACTTTATG | 900 |
| AATTCTTTGT | TTGTAACTGC | AGAGACTGTT | AGAAGTCAAA | CTGTGTGGGG | AGGACACTTA | 960 |
| GTTAGTTCAC | GAAATACGGC | TGGTAACCGT | ATAAATTTCC | CTAGTTACGG | GGTCTTCAAT | 1020 |
| CCTGGTGGCG | CCATTTGGAT | TGCAGATGAG | GATCCACGTC | CTTTTATCG | GACATTATCA | 1080 |
| GATCCTGTTT | TTGTCCGAGG | AGGATTTGGG | AATCCTCATT | ATGTACTGGG | GCTTAGGGGA | 1140 |
| GTAGCATTTC | AACAAACTGG | TACGAACCAC | ACCCGAACAT | TTAGAAATAG | TGGGACCATA | 1200 |
| GATTCTCTAG | ATGAAATCCC | ACCTCAGGAT | AATAGTGGGG | CACCTTGGAA | TGATTATAGT | 1260 |
| CATGTATTAA | ATCATGTTAC | ATTTGTACGA | TGGCCAGGTG | AGATTTCAGG | AAGTGATTCA | 1320 |
| TGGAGAGCTC | CAATGTTTTC | TTGGACGCAC | CGTAGTGCAA | CCCCTACAAA | TACAATTGAT | 1380 |
| CCGGAGAGGA | TTACTCAAAT | ACCATTGGTA | AAAGCACATA | CACTTCAGTC | AGGTACTACT | 1440 |
| GTTGTAAGAG | GGCCCGGGTT | TACGGGAGGA | GATATTCTTC | GACGAACAAG | TGGAGGACCA | 1500 |
| TTTGCTTATA | CTATTGTTAA | TATAAATGGG | CAATTACCCC | AAAGGTATCG | TGCAAGAATA | 1560 |
| CGCTATGCCT | CTACTACAAA | TCTAAGAATT | TACGTAACGG | TTGCAGGTGA | ACGGATTTTT | 1620 |
| GCTGGTCAAT | TTAACAAAAC | AATGGATACC | GGTGACCCAT | TAACATTCCA | ATCTTTTAGT | 1680 |
| TACGCAACTA | TTAATACAGC | TTTTACATTC | CCAATGAGCC | AGAGTAGTTT | CACAGTAGGT | 1740 |
| GCTGATACTT | TTAGTTCAGG | GAATGAAGTT | TATATAGACA | GATTTGAATT | GATTCCAGTT | 1800 |
| ACTGCAACAT | TTGAAGCAGA | ATATGATTTA | GAAAGAGCAC | AAAAGGCGGT | GAATGCGCTG | 1860 |
| TTTACTTCTA | TAAACCAAAT | AGGGATAAAA | ACAGATGTGA | CGGATTATCA | TATCGATCGA | 1920 |
| GTATCCAATT | TAGTTGAGTG | TTTATCTGAT | GAATTTGTC | TGGATGAAAA | AAAAGAATTG | 1980 |
| TCCGAGAAAG | TCAAACATGC | GAAGCGACTT | AGTGATGAGC | GGAATTTACT | TCAAGATCCA | 2040 |
| AACTTTAGAG | GGATCAATAG | ACAACTAGAC | CGTGGCTGGA | GAGGAAGTAC | GGATATTACC | 2100 |
| ATCCAAGGAG | GCGATGACGT | ATTCAAAGAG | AATTACGTTA | CGCTATTGGG | TACCTTTGAT | 2160 |
| GAGTGCTATC | CAACGTATTT | ATATCAAAAA | ATAGATGAGT | CGAAATTAAA | AGCCTATACC | 2220 |
| CGTTACCAAT | TAAGAGGGTA | TATCGAAGAT | AGTCAAGACT | TAGAAATCTA | TTTAATTCGC | 2280 |

```
TACAATGCCA AACACGAAAC AGTAAATGTG CCAGGTACGG GTTCCTTATG GCCGCTTTCA    2340
GCCCCAAGTC CAATCGGAAA ATGTGCCCAT CATTCCCATC ATTTCTCCTT GGACATTGAT    2400
GTTGGATGTA CAGACTTAAA TGAGGACTTA GGTGTATGGG TGATATTCAA GATTAAGACG    2460
CAAGATGGCC ATGCAAGACT AGGAAATCTA GAATTTCTCG AAGAGAAACC ATTAGTAGGA    2520
GAAGCACTAG CTCGTGTGAA AAGAGCGGAG AAAAAATGGA GAGACAAACG TGAAAAATTG    2580
GAATGGGAAA CAAATATTGT TTATAAAGAG GCAAAGAAT CTGTAGATGC TTTATTTGTA    2640
AACTCTCAAT ATGATAGATT ACAAGCGGAT ACCAACATCG CGATGATTCA TGCGGCAGAT    2700
AAACGCGTTC ATAGCATTCG AGAAGCTTAT CTGCCTGAGC TGTCTGTGAT TCCGGGTGTC    2760
AATGCGGCTA TTTTTGAAGA ATTAGAAGGG CGTATTTTCA CTGCATTCTC CCTATATGAT    2820
GCGAGAAATG TCATTAAAAA TGGTGATTTT AATAATGGCT TATCCTGCTG GAACGTGAAA    2880
GGGCATGTAG ATGTAGAAGA ACAAAACAAC CACCGTTCGG TCCTTGTTGT TCCGGAATGG    2940
GAAGCAGAAG TGTCACAAGA AGTTCGTGTC TGTCCGGGTC GTGGCTATAT CCTTCGTGTC    3000
ACAGCGTACA AGGAGGGATA TGGAGAAGGT TGCGTAACCA TCATGAGAT CGAGAACAAT    3060
ACAGACGAAC TGAAGTTTAG CAACTGTGTA GAAGAGGAAG TATATCCAAA CAACACGGTA    3120
ACGTGTAATG ATTATACTGC GACTCAAGAA GAATATGAGG GTACGTACAC TTCTCGTAAT    3180
CGAGGATATG ACGGAGCCTA TGAAAGCAAT TCTTCTGTAC CAGCTGATTA TGCATCAGCC    3240
TATGAAGAAA AAGCATATAC AGATGGACGA AGAGACAATC CTTGTGAATC TAACAGAGGA    3300
TATGGGGATT ACACACCACT ACCAGCTGGC TATGTGACAA AAGAATTAGA GTACTTCCCA    3360
GAAACCGATA AGGTATGGAT TGAGATCGGA GAAACGGAAG GAACATTCAT CGTGGACAGC    3420
GTGGAATTAC TTCTTATGGA GGAA                                           3444
```

(2) INFORMATION FOR SEQ ID NO:23:

(i) SEQUENCE CHARACTERISTICS:
        (A) LENGTH: 1148 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:23:

```
Met Glu Asn Asn Ile Gln Asn Gln Cys Val Pro Tyr Asn Cys Leu Asn
 1               5                  10                  15

Asn Pro Glu Val Glu Ile Leu Asn Glu Glu Arg Ser Thr Gly Arg Leu
            20                  25                  30

Pro Leu Asp Ile Ser Leu Ser Leu Thr Arg Phe Leu Leu Ser Glu Phe
        35                  40                  45

Val Pro Gly Val Gly Val Ala Phe Gly Leu Phe Asp Leu Ile Trp Gly
    50                  55                  60

Phe Ile Thr Pro Ser Asp Trp Ser Leu Phe Leu Leu Gln Ile Glu Gln
65                  70                  75                  80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
145                 150                 155                 160
```

Gln Ala Ala Asn Leu His Leu Ser Leu Leu Arg Asp Ala Val Ser Phe
                165                 170                 175

Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
            195                 200                 205

Tyr Asn Gln Gly Leu Glu Asn Leu Arg Gly Thr Asn Thr Arg Gln Trp
    210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
                245                 250                 255

Thr Ser Ser Gln Leu Thr Arg Glu Ile Tyr Thr Ser Ser Val Ile Glu
                260                 265                 270

Asp Ser Pro Val Ser Ala Asn Ile Pro Asn Gly Phe Asn Arg Ala Glu
            275                 280                 285

Phe Gly Val Arg Pro Pro His Leu Met Asp Phe Met Asn Ser Leu Phe
    290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Arg Ile Asn Phe Pro Ser Tyr
                325                 330                 335

Gly Val Phe Asn Pro Gly Gly Ala Ile Trp Ile Ala Asp Glu Asp Pro
            340                 345                 350

Arg Pro Phe Tyr Arg Thr Leu Ser Asp Pro Val Phe Val Arg Gly Gly
    355                 360                 365

Phe Gly Asn Pro His Tyr Val Leu Gly Leu Arg Gly Val Ala Phe Gln
    370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
                405                 410                 415

Asn Asp Tyr Ser His Val Leu Asn His Val Thr Phe Val Arg Trp Pro
            420                 425                 430

Gly Glu Ile Ser Gly Ser Asp Ser Trp Arg Ala Pro Met Phe Ser Trp
        435                 440                 445

Thr His Arg Ser Ala Thr Pro Thr Asn Thr Ile Asp Pro Glu Arg Ile
    450                 455                 460

Thr Gln Ile Pro Leu Val Lys Ala His Thr Leu Gln Ser Gly Thr Thr
465                 470                 475                 480

Val Val Arg Gly Pro Gly Phe Thr Gly Gly Asp Ile Leu Arg Arg Thr
                485                 490                 495

Ser Gly Gly Pro Phe Ala Tyr Thr Ile Val Asn Ile Asn Gly Gln Leu
            500                 505                 510

Pro Gln Arg Tyr Arg Ala Arg Ile Arg Tyr Ala Ser Thr Thr Asn Leu
        515                 520                 525

Arg Ile Tyr Val Thr Val Ala Gly Glu Arg Ile Phe Ala Gly Gln Phe
    530                 535                 540

Asn Lys Thr Met Asp Thr Gly Asp Pro Leu Thr Phe Gln Ser Phe Ser
545                 550                 555                 560

Tyr Ala Thr Ile Asn Thr Ala Phe Thr Phe Pro Met Ser Gln Ser Ser
                565                 570                 575

Phe Thr Val Gly Ala Asp Thr Phe Ser Ser Gly Asn Glu Val Tyr Ile
            580                 585                 590

Asp Arg Phe Glu Leu Ile Pro Val Thr Ala Thr Phe Glu Ala Glu Tyr
    595                 600                 605

| | | | | | | | | | | | | | | |
|---|---|---|---|---|---|---|---|---|---|---|---|---|---|---|
| Asp | Leu | Glu | Arg | Ala | Gln | Lys | Ala | Val | Asn | Ala | Leu | Phe | Thr | Ser | Ile |
| | 610 | | | | 615 | | | | 620 | | | | | |
| Asn | Gln | Ile | Gly | Ile | Lys | Thr | Asp | Val | Thr | Asp | Tyr | His | Ile | Asp | Arg |
| 625 | | | | | 630 | | | | | 635 | | | | | 640 |
| Val | Ser | Asn | Leu | Val | Glu | Cys | Leu | Ser | Asp | Glu | Phe | Cys | Leu | Asp | Glu |
| | | | | 645 | | | | | 650 | | | | | 655 | |
| Lys | Lys | Glu | Leu | Ser | Glu | Lys | Val | Lys | His | Ala | Lys | Arg | Leu | Ser | Asp |
| | | | 660 | | | | | 665 | | | | | 670 | | |
| Glu | Arg | Asn | Leu | Leu | Gln | Asp | Pro | Asn | Phe | Arg | Gly | Ile | Asn | Arg | Gln |
| | | 675 | | | | | 680 | | | | | 685 | | | |
| Leu | Asp | Arg | Gly | Trp | Arg | Gly | Ser | Thr | Asp | Ile | Thr | Ile | Gln | Gly | Gly |
| | 690 | | | | | 695 | | | | | 700 | | | | |
| Asp | Asp | Val | Phe | Lys | Glu | Asn | Tyr | Val | Thr | Leu | Leu | Gly | Thr | Phe | Asp |
| 705 | | | | | 710 | | | | | 715 | | | | | 720 |
| Glu | Cys | Tyr | Pro | Thr | Tyr | Leu | Tyr | Gln | Lys | Ile | Asp | Glu | Ser | Lys | Leu |
| | | | | 725 | | | | | 730 | | | | | 735 | |
| Lys | Ala | Tyr | Thr | Arg | Tyr | Gln | Leu | Arg | Gly | Tyr | Ile | Glu | Asp | Ser | Gln |
| | | | 740 | | | | | 745 | | | | | 750 | | |
| Asp | Leu | Glu | Ile | Tyr | Leu | Ile | Arg | Tyr | Asn | Ala | Lys | His | Glu | Thr | Val |
| | | 755 | | | | | 760 | | | | | 765 | | | |
| Asn | Val | Pro | Gly | Thr | Gly | Ser | Leu | Trp | Pro | Leu | Ser | Ala | Pro | Ser | Pro |
| | 770 | | | | | 775 | | | | | 780 | | | | |
| Ile | Gly | Lys | Cys | Ala | His | His | Ser | His | His | Phe | Ser | Leu | Asp | Ile | Asp |
| 785 | | | | | 790 | | | | | 795 | | | | | 800 |
| Val | Gly | Cys | Thr | Asp | Leu | Asn | Glu | Asp | Leu | Gly | Val | Trp | Val | Ile | Phe |
| | | | | 805 | | | | | 810 | | | | | 815 | |
| Lys | Ile | Lys | Thr | Gln | Asp | Gly | His | Ala | Arg | Leu | Gly | Asn | Leu | Glu | Phe |
| | | | 820 | | | | | 825 | | | | | 830 | | |
| Leu | Glu | Glu | Lys | Pro | Leu | Val | Gly | Glu | Ala | Leu | Ala | Arg | Val | Lys | Arg |
| | | 835 | | | | | 840 | | | | | 845 | | | |
| Ala | Glu | Lys | Lys | Trp | Arg | Asp | Lys | Arg | Glu | Lys | Leu | Glu | Trp | Glu | Thr |
| | 850 | | | | | 855 | | | | | 860 | | | | |
| Asn | Ile | Val | Tyr | Lys | Glu | Ala | Lys | Glu | Ser | Val | Asp | Ala | Leu | Phe | Val |
| 865 | | | | | 870 | | | | | 875 | | | | | 880 |
| Asn | Ser | Gln | Tyr | Asp | Arg | Leu | Gln | Ala | Asp | Thr | Asn | Ile | Ala | Met | Ile |
| | | | | 885 | | | | | 890 | | | | | 895 | |
| His | Ala | Ala | Asp | Lys | Arg | Val | His | Ser | Ile | Arg | Glu | Ala | Tyr | Leu | Pro |
| | | | 900 | | | | | 905 | | | | | 910 | | |
| Glu | Leu | Ser | Val | Ile | Pro | Gly | Val | Asn | Ala | Ala | Ile | Phe | Glu | Glu | Leu |
| | | 915 | | | | | 920 | | | | | 925 | | | |
| Glu | Gly | Arg | Ile | Phe | Thr | Ala | Phe | Ser | Leu | Tyr | Asp | Ala | Arg | Asn | Val |
| | 930 | | | | | 935 | | | | | 940 | | | | |
| Ile | Lys | Asn | Gly | Asp | Phe | Asn | Asn | Gly | Leu | Ser | Cys | Trp | Asn | Val | Lys |
| 945 | | | | | 950 | | | | | 955 | | | | | 960 |
| Gly | His | Val | Asp | Val | Glu | Glu | Gln | Asn | Asn | His | Arg | Ser | Val | Leu | Val |
| | | | | 965 | | | | | 970 | | | | | 975 | |
| Val | Pro | Glu | Trp | Glu | Ala | Glu | Val | Ser | Gln | Glu | Val | Arg | Val | Cys | Pro |
| | | | 980 | | | | | 985 | | | | | 990 | | |
| Gly | Arg | Gly | Tyr | Ile | Leu | Arg | Val | Thr | Ala | Tyr | Lys | Glu | Gly | Tyr | Gly |
| | | 995 | | | | | 1000 | | | | | 1005 | | | |
| Glu | Gly | Cys | Val | Thr | Ile | His | Glu | Ile | Glu | Asn | Asn | Thr | Asp | Glu | Leu |
| | | 1010 | | | | | 1015 | | | | | 1020 | | | |
| Lys | Phe | Ser | Asn | Cys | Val | Glu | Glu | Glu | Val | Tyr | Pro | Asn | Asn | Thr | Val |
| 1025 | | | | | 1030 | | | | | 1035 | | | | | 1040 |
| Thr | Cys | Asn | Asp | Tyr | Thr | Ala | Thr | Gln | Glu | Glu | Tyr | Glu | Gly | Thr | Tyr |

|   |   |   |   | 1045 |   |   |   | 1050 |   |   |   | 1055 |   |
|---|---|---|---|---|---|---|---|---|---|---|---|---|---|

Thr Ser Arg Asn Arg Gly Tyr Asp Gly Ala Tyr Glu Ser Asn Ser Ser
          1060                1065               1070

Val Pro Ala Asp Tyr Ala Ser Ala Tyr Glu Glu Lys Ala Tyr Thr Asp
          1075               1080              1085

Gly Arg Arg Asp Asn Pro Cys Glu Ser Asn Arg Gly Tyr Gly Asp Tyr
          1090               1095              1100

Thr Pro Leu Pro Ala Gly Tyr Val Thr Lys Glu Leu Glu Tyr Phe Pro
1105              1110              1115                   1120

Glu Thr Asp Lys Val Trp Ile Glu Ile Gly Glu Thr Glu Gly Thr Phe
                1125             1130                  1135

Ile Val Asp Ser Val Glu Leu Leu Leu Met Glu Glu
                1140              1145

( 2 ) INFORMATION FOR SEQ ID NO:24:

( i ) SEQUENCE CHARACTERISTICS:
        ( A ) LENGTH: 3522 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

```
ATGGAAAATA ATATTCAAAA TCAATGCGTA CCTTACAATT GTTTAAATAA TCCTGAAGTA      60
GAAATACTGA ACGAAGAACG CAGCACCGGC CGCCTGCCGC TGGACATCAG CCTGAGCCTT     120
ACACGTTTCC TTTTGAGTGA ATTTGTTCCA GGTGTGGGAG TTGCGTTTGG ATTATTTGAT     180
TTAATATGGG GTTTTATAAC TCCTTCTGAT GGAGCTTAT TTCTTTTACA GATTGAACAA      240
TTGATTGAGC AAAGAATAGA AACATTGGAA AGGAACCGGG CAATTACTAC ATTACGAGGG     300
TTAGCAGATA GCTATGAAAT TTATATTGAA GCACTAAGAG AGTGGGAAGC AAATCCTAAT     360
AATGCACAAT TAAGGGAAGA TGTGCGTATT CGATTTGCTA ATACAGACGA CGCTTTAATA     420
ACAGCAATAA ATAATTTTAC ACTTACAAGT TTTGAAATCC CTCTTTTATC GGTCTATGTT     480
CAAGCGGCGA ATTTACATTT ATCACTATTA GAGACGCTG TATCGTTTGG GCAGGGTTGG      540
GGACTGGATA TAGCTACTGT TAATAATCAT TATAATAGAT TAATAAATCT TATTCATAGA     600
TATACGAAAC ATTGTTTGGA CACATACAAT CAAGGATTAG AAAACTTAAG AGGTACTAAT     660
ACTCGACAAT GGGCAAGATT CAATCAGTTT AGGAGAGATT TAACACTTAC TGTATTAGAT     720
ATCGTTGCTC TTTTTCCGAA CTACGATGTT AGAACATATC CAATTCAAAC GTCATCCCAA     780
TTAACAAGGG AAATTTATAC AAGTTCAGTA ATTGAGGATT CTCCAGTTTC TGCTAATATA     840
CCTAATGGTT TTAATAGGGC GGAATTTGGA GTTAGACCGC CCATCTTAT GGACTTTATG      900
AATTCTTTGT TTGTAACTGC AGAGACTGTT AGAAGTCAAA CTGTGTGGGG AGGACACTTA     960
GTTAGTTCAC GAAATACGGC TGGTAACCGT ATAAATTTCC CTAGTTACGG GGTCTTCAAT    1020
CCTGGTGGCG CCATTTGGAT TGCAGATGAG GATCCACGTC CTTTTATCG GACATTATCA     1080
GATCCTGTTT TTGTCCGAGG AGGATTTGGG AATCCTCATT ATGTACTGGG CTTAGGGGA     1140
GTAGCATTTC AACAAACTGG TACGAACCAC ACCCGAACAT TTAGAAATAG TGGGACCATA    1200
GATTCTCTAG ATGAAATCCC ACCTCAGGAT AATAGTGGGG CACCTTGGAA TGATTATAGT    1260
CATGTATTAA ATCATGTTAC ATTTGTACGA TGGCCAGGTG AGATTTCAGG AAGTGATTCA    1320
TGGAGAGCTC CAATGTTTTC TTGGACGCAC CGTAGTGCAA CCCCTACAAA TACAATTGAT    1380
CCGGAGAGGA TTACTCAAAT ACCATTGGTA AAAGCACATA CACTTCAGTC AGGTACTACT    1440
GTTGTAAGAG GGCCCGGGTT TACGGGAGGA GATATTCTTC GACGAACAAG TGGAGGACCA    1500
```

```
TTTGCTTATA CTATTGTTAA TATAAATGGG CAATTACCCC AAAGGTATCG TGCAAGAATA   1560
CGCTATGCCT CTACTACAAA TCTAAGAATT TACGTAACGG TTGCAGGTGA ACGGATTTTT   1620
GCTGGTCAAT TTAACAAAAC AATGGATACC GGTGACCCAT TAACATTCCA ATCTTTTAGT   1680
TACGCAACTA TTAATACAGC TTTTACATTC CCAATGAGCC AGAGTAGTTT CACAGTAGGT   1740
GCTGATACTT TTAGTTCAGG GAATGAAGTT TATATAGACA GATTTGAATT GATTCCAGTT   1800
ACTGCAACAT TTGAAGCAGA ATATGATTTA GAAAGAGCAC AAAAGGCGGT GAATGCGCTG   1860
TTTACTTCTA TAAACCAAAT AGGGATAAAA ACAGATGTGA CGGATTATCA TATTGATCAA   1920
GTATCCAATT TAGTGGATTG TTTATCAGAT GAATTTTGTC TGGATGAAAA GCGAGAATTG   1980
TCCGAGAAAG TCAAACATGC GAAGCGACTC AGTGATGAGC GGAATTTACT TCAAGATCCA   2040
AACTTCAAAG GCATCAATAG GCAACTAGAC CGTGGTTGGA GAGGAAGTAC GGATATTACC   2100
ATCCAAAGAG GAGATGACGT ATTCAAAGAA AATTATGTCA CACTACCAGG TACCTTTGAT   2160
GAGTGCTATC CAACGTATTT ATATCAAAAA ATAGATGAGT CGAAATTAAA ACCCTATACT   2220
CGTTATCAAT TAAGAGGGTA TATCGAGGAT AGTCAAGACT TAGAAATCTA TTTGATCCGC   2280
TATAATGCAA AACACGAAAC AGTAAATGTG CTAGGTACGG GTTCTTTATG GCCGCTTTCA   2340
GTCCAAAGTC CAATCAGAAA GTGTGGAGAA CCGAATCGAT GCGCGCCACA CCTTGAATGG   2400
AATCCTGATC TAGATTGTTC CTGCAGAGAC GGGGAAAAAT GTGCACATCA TTCGCATCAT   2460
TTCTCCTTGG ACATTGATGT TGGATGTACA GACTTAAATG AGGACTTAGA TGTATGGGTG   2520
ATATTCAAGA TTAAGACGCA AGATGGCCAT GCAAGACTAG GAAATCTAGA GTTTCTCGAA   2580
GAGAAACCAT TAGTCGGGGA AGCACTAGCT CGTGTGAAAA GAGCAGAGAA AAAATGGAGA   2640
GATAAACGTG AAAAATTGGA ATTGGAAACA AATATTGTTT ATAAAGAGGC AAAAGAATCT   2700
GTAGATGCTT TATTTGTAAA CTCTCAATAT GATCAATTAC AAGCGGATAC GAATATTGCC   2760
ATGATTCATG CGGCAGATAA ACGTGTTCAT AGAATTCGGG AAGCGTATCT TCCAGAGTTA   2820
TCTGTGATTC CGGGTGTAAA TGTAGACATT TTCGAAGAAT TAAAAGGGCG TATTTTCACT   2880
GCATTCTTCC TATATGATGC GAGAAATGTC ATTAAAAACG GTGATTTCAA TAATGGCTTA   2940
TCATGCTGGA ACGTGAAAGG GCATGTAGAT GTAGAAGAAC AAAACAACCA CCGTTCGGTC   3000
CTTGTTGTTC CGGAATGGGA AGCAGAAGTG TCACAAGAAG TTCGTGTCTG TCCGGGTCGT   3060
GGCTATATCC TTCGTGTCAC AGCGTACAAG GAGGGATATG GAGAAGGTTG CGTAACCATT   3120
CATGAGATCG AGAACAATAC AGACGAACTG AAGTTTAGCA ACTGCGTAGA AGAGGAAGTC   3180
TATCCAAACA ACACGGTAAC GTGTAATGAT TATACTGCAA ATCAAGAAGA ATACGGGGGT   3240
GCGTACACTT CCCGTAATCG TGGATATGAC GAAACTTATG GAAGCAATTC TTCTGTACCA   3300
GCTGATTATG CGTCAGTCTA TGAAGAAAAA TCGTATACAG ATGGACGAAG AGACAATCCT   3360
TGTGAATCTA ACAGAGGATA TGGGGATTAC ACACCACTAC CAGCTGGCTA TGTGACAAAA   3420
GAATTAGAGT ACTTCCCAGA AACCGATAAG GTATGGATTG AGATCGGAGA AACGGAAGGA   3480
ACATTCATCG TGGACAGCGT GGAATTACTC CTTATGGAGG AA                      3522
```

( 2 ) INFORMATION FOR SEQ ID NO:25:

( i ) SEQUENCE CHARACTERISTICS:
        ( A ) LENGTH: 1174 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:25:

```
Met Glu Asn Asn Ile Gln Asn Gln Cys Val Pro Tyr Asn Cys Leu Asn
 1               5                  10                  15
```

| | | | | | | | | | | | | | | |
|---|---|---|---|---|---|---|---|---|---|---|---|---|---|---|
| Asn | Pro | Glu | Val | Glu | Ile | Leu | Asn | Glu | Glu | Arg | Ser | Thr | Gly | Arg | Leu |
| | | | 20 | | | | | 25 | | | | | 30 | | |
| Pro | Leu | Asp | Ile | Ser | Leu | Ser | Leu | Thr | Arg | Phe | Leu | Leu | Ser | Glu | Phe |
| | | | 35 | | | | | 40 | | | | | 45 | | |
| Val | Pro | Gly | Val | Gly | Val | Ala | Phe | Gly | Leu | Phe | Asp | Leu | Ile | Trp | Gly |
| | | | 50 | | | | | 55 | | | | | 60 | | |
| Phe | Ile | Thr | Pro | Ser | Asp | Trp | Ser | Leu | Phe | Leu | Leu | Gln | Ile | Glu | Gln |
| 65 | | | | | 70 | | | | | 75 | | | | | 80 |
| Leu | Ile | Glu | Gln | Arg | Ile | Glu | Thr | Leu | Glu | Arg | Asn | Arg | Ala | Ile | Thr |
| | | | | 85 | | | | | 90 | | | | | 95 | |
| Thr | Leu | Arg | Gly | Leu | Ala | Asp | Ser | Tyr | Glu | Ile | Tyr | Ile | Glu | Ala | Leu |
| | | | 100 | | | | | 105 | | | | | 110 | | |
| Arg | Glu | Trp | Glu | Ala | Pro | Asn | Asn | Ala | Gln | Leu | Arg | Glu | Asp | Val | |
| | | | 115 | | | | | 120 | | | | | 125 | | |
| Arg | Ile | Arg | Phe | Ala | Asn | Thr | Asp | Asp | Ala | Leu | Ile | Thr | Ala | Ile | Asn |
| | | | 130 | | | | | 135 | | | | | 140 | | |
| Asn | Phe | Thr | Leu | Thr | Ser | Phe | Glu | Ile | Pro | Leu | Leu | Ser | Val | Tyr | Val |
| 145 | | | | | 150 | | | | | 155 | | | | | 160 |
| Gln | Ala | Ala | Asn | Leu | His | Leu | Ser | Leu | Leu | Arg | Asp | Ala | Val | Ser | Phe |
| | | | | 165 | | | | | 170 | | | | | 175 | |
| Gly | Gln | Gly | Trp | Gly | Leu | Asp | Ile | Ala | Thr | Val | Asn | Asn | His | Tyr | Asn |
| | | | 180 | | | | | 185 | | | | | 190 | | |
| Arg | Leu | Ile | Asn | Leu | Ile | His | Arg | Tyr | Thr | Lys | His | Cys | Leu | Asp | Thr |
| | | | 195 | | | | | 200 | | | | | 205 | | |
| Tyr | Asn | Gln | Gly | Leu | Glu | Asn | Leu | Arg | Gly | Thr | Asn | Thr | Arg | Gln | Trp |
| | | | 210 | | | | | 215 | | | | | 220 | | |
| Ala | Arg | Phe | Asn | Gln | Phe | Arg | Arg | Asp | Leu | Thr | Leu | Thr | Val | Leu | Asp |
| 225 | | | | | 230 | | | | | 235 | | | | | 240 |
| Ile | Val | Ala | Leu | Phe | Pro | Asn | Tyr | Asp | Val | Arg | Thr | Tyr | Pro | Ile | Gln |
| | | | | 245 | | | | | 250 | | | | | 255 | |
| Thr | Ser | Ser | Gln | Leu | Thr | Arg | Glu | Ile | Tyr | Thr | Ser | Ser | Val | Ile | Glu |
| | | | 260 | | | | | 265 | | | | | 270 | | |
| Asp | Ser | Pro | Val | Ser | Ala | Asn | Ile | Pro | Asn | Gly | Phe | Asn | Arg | Ala | Glu |
| | | | 275 | | | | | 280 | | | | | 285 | | |
| Phe | Gly | Val | Arg | Pro | Pro | His | Leu | Met | Asp | Phe | Met | Asn | Ser | Leu | Phe |
| | | | 290 | | | | | 295 | | | | | 300 | | |
| Val | Thr | Ala | Glu | Thr | Val | Arg | Ser | Gln | Thr | Val | Trp | Gly | Gly | His | Leu |
| 305 | | | | | 310 | | | | | 315 | | | | | 320 |
| Val | Ser | Ser | Arg | Asn | Thr | Ala | Gly | Asn | Arg | Ile | Asn | Phe | Pro | Ser | Tyr |
| | | | | 325 | | | | | 330 | | | | | 335 | |
| Gly | Val | Phe | Asn | Pro | Gly | Gly | Ala | Ile | Trp | Ile | Ala | Asp | Glu | Asp | Pro |
| | | | 340 | | | | | 345 | | | | | 350 | | |
| Arg | Pro | Phe | Tyr | Arg | Thr | Leu | Ser | Asp | Pro | Val | Phe | Val | Arg | Gly | Gly |
| | | | 355 | | | | | 360 | | | | | 365 | | |
| Phe | Gly | Asn | Pro | His | Tyr | Val | Leu | Gly | Leu | Arg | Gly | Val | Ala | Phe | Gln |
| | | | 370 | | | | | 375 | | | | | 380 | | |
| Gln | Thr | Gly | Thr | Asn | His | Thr | Arg | Thr | Phe | Arg | Asn | Ser | Gly | Thr | Ile |
| 385 | | | | | 390 | | | | | 395 | | | | | 400 |
| Asp | Ser | Leu | Asp | Glu | Ile | Pro | Pro | Gln | Asp | Asn | Ser | Gly | Ala | Pro | Trp |
| | | | | 405 | | | | | 410 | | | | | 415 | |
| Asn | Asp | Tyr | Ser | His | Val | Leu | Asn | His | Val | Thr | Phe | Val | Arg | Trp | Pro |
| | | | 420 | | | | | 425 | | | | | 430 | | |
| Gly | Glu | Ile | Ser | Gly | Ser | Asp | Ser | Trp | Arg | Ala | Pro | Met | Phe | Ser | Trp |
| | | | 435 | | | | | 440 | | | | | 445 | | |
| Thr | His | Arg | Ser | Ala | Thr | Pro | Thr | Asn | Thr | Ile | Asp | Pro | Glu | Arg | Ile |

|     |     |     |     | 450 |     |     |     |     | 455 |     |     |     |     | 460 |     |     |
| --- | --- | --- | --- | --- | --- | --- | --- | --- | --- | --- | --- | --- | --- | --- | --- | --- |
| Thr | Gln | Ile | Pro | Leu | Val | Lys | Ala | His | Thr | Leu | Gln | Ser | Gly | Thr | Thr |
| 465 |     |     |     | 470 |     |     |     |     | 475 |     |     |     |     |     | 480 |
| Val | Val | Arg | Gly | Pro | Gly | Phe | Thr | Gly | Gly | Asp | Ile | Leu | Arg | Arg | Thr |
|     |     |     |     | 485 |     |     |     |     | 490 |     |     |     |     | 495 |     |
| Ser | Gly | Gly | Pro | Phe | Ala | Tyr | Thr | Ile | Val | Asn | Ile | Asn | Gly | Gln | Leu |
|     |     |     | 500 |     |     |     |     | 505 |     |     |     |     | 510 |     |     |
| Pro | Gln | Arg | Tyr | Arg | Ala | Arg | Ile | Arg | Tyr | Ala | Ser | Thr | Thr | Asn | Leu |
|     |     | 515 |     |     |     |     | 520 |     |     |     |     | 525 |     |     |     |
| Arg | Ile | Tyr | Val | Thr | Val | Ala | Gly | Glu | Arg | Ile | Phe | Ala | Gly | Gln | Phe |
|     |     | 530 |     |     |     |     | 535 |     |     |     |     | 540 |     |     |     |
| Asn | Lys | Thr | Met | Asp | Thr | Gly | Asp | Pro | Leu | Thr | Phe | Gln | Ser | Phe | Ser |
| 545 |     |     |     |     | 550 |     |     |     |     | 555 |     |     |     |     | 560 |
| Tyr | Ala | Thr | Ile | Asn | Thr | Ala | Phe | Thr | Phe | Pro | Met | Ser | Gln | Ser | Ser |
|     |     |     |     | 565 |     |     |     |     | 570 |     |     |     |     | 575 |     |
| Phe | Thr | Val | Gly | Ala | Asp | Thr | Phe | Ser | Ser | Gly | Asn | Glu | Val | Tyr | Ile |
|     |     |     | 580 |     |     |     |     | 585 |     |     |     |     | 590 |     |     |
| Asp | Arg | Phe | Glu | Leu | Ile | Pro | Val | Thr | Ala | Thr | Phe | Glu | Ala | Glu | Tyr |
|     |     | 595 |     |     |     |     | 600 |     |     |     |     | 605 |     |     |     |
| Asp | Leu | Glu | Arg | Ala | Gln | Lys | Ala | Val | Asn | Ala | Leu | Phe | Thr | Ser | Ile |
|     | 610 |     |     |     |     | 615 |     |     |     |     | 620 |     |     |     |     |
| Asn | Gln | Ile | Gly | Ile | Lys | Thr | Asp | Val | Thr | Asp | Tyr | His | Ile | Asp | Gln |
| 625 |     |     |     |     | 630 |     |     |     |     | 635 |     |     |     |     | 640 |
| Val | Ser | Asn | Leu | Val | Asp | Cys | Leu | Ser | Asp | Glu | Phe | Cys | Leu | Asp | Glu |
|     |     |     |     | 645 |     |     |     |     | 650 |     |     |     |     | 655 |     |
| Lys | Arg | Glu | Leu | Ser | Glu | Lys | Val | Lys | His | Ala | Lys | Arg | Leu | Ser | Asp |
|     |     |     |     | 660 |     |     |     |     | 665 |     |     |     |     | 670 |     |
| Glu | Arg | Asn | Leu | Leu | Gln | Asp | Pro | Asn | Phe | Lys | Gly | Ile | Asn | Arg | Gln |
|     |     | 675 |     |     |     |     | 680 |     |     |     |     | 685 |     |     |     |
| Leu | Asp | Arg | Gly | Trp | Arg | Gly | Ser | Thr | Asp | Ile | Thr | Ile | Gln | Arg | Gly |
|     | 690 |     |     |     |     | 695 |     |     |     |     | 700 |     |     |     |     |
| Asp | Asp | Val | Phe | Lys | Glu | Asn | Tyr | Val | Thr | Leu | Pro | Gly | Thr | Phe | Asp |
| 705 |     |     |     |     | 710 |     |     |     |     | 715 |     |     |     |     | 720 |
| Glu | Cys | Tyr | Pro | Thr | Tyr | Leu | Tyr | Gln | Lys | Ile | Asp | Glu | Ser | Lys | Leu |
|     |     |     |     | 725 |     |     |     |     | 730 |     |     |     |     | 735 |     |
| Lys | Pro | Tyr | Thr | Arg | Tyr | Gln | Leu | Arg | Gly | Tyr | Ile | Glu | Asp | Ser | Gln |
|     |     |     | 740 |     |     |     |     | 745 |     |     |     |     | 750 |     |     |
| Asp | Leu | Glu | Ile | Tyr | Leu | Ile | Arg | Tyr | Asn | Ala | Lys | His | Glu | Thr | Val |
|     |     | 755 |     |     |     |     | 760 |     |     |     |     | 765 |     |     |     |
| Asn | Val | Leu | Gly | Thr | Gly | Ser | Leu | Trp | Pro | Leu | Ser | Val | Gln | Ser | Pro |
|     | 770 |     |     |     |     | 775 |     |     |     |     | 780 |     |     |     |     |
| Ile | Arg | Lys | Cys | Gly | Glu | Pro | Asn | Arg | Cys | Ala | Pro | His | Leu | Glu | Trp |
| 785 |     |     |     | 790 |     |     |     |     | 795 |     |     |     |     |     | 800 |
| Asn | Pro | Asp | Leu | Asp | Cys | Ser | Cys | Arg | Asp | Gly | Glu | Lys | Cys | Ala | His |
|     |     |     |     | 805 |     |     |     |     | 810 |     |     |     |     | 815 |     |
| His | Ser | His | His | Phe | Ser | Leu | Asp | Ile | Asp | Val | Gly | Cys | Thr | Asp | Leu |
|     |     |     | 820 |     |     |     |     | 825 |     |     |     |     | 830 |     |     |
| Asn | Glu | Asp | Leu | Asp | Val | Trp | Val | Ile | Phe | Lys | Ile | Lys | Thr | Gln | Asp |
|     |     | 835 |     |     |     |     | 840 |     |     |     |     | 845 |     |     |     |
| Gly | His | Ala | Arg | Leu | Gly | Asn | Leu | Glu | Phe | Leu | Glu | Glu | Lys | Pro | Leu |
|     | 850 |     |     |     |     | 855 |     |     |     |     | 860 |     |     |     |     |
| Val | Gly | Glu | Ala | Leu | Ala | Arg | Val | Lys | Arg | Ala | Glu | Lys | Lys | Trp | Arg |
| 865 |     |     |     |     | 870 |     |     |     |     | 875 |     |     |     |     | 880 |
| Asp | Lys | Arg | Glu | Lys | Leu | Glu | Leu | Glu | Thr | Asn | Ile | Val | Tyr | Lys | Glu |
|     |     |     |     | 885 |     |     |     |     | 890 |     |     |     |     | 895 |     |

| | | | | | | | | | | | | | | |
|---|---|---|---|---|---|---|---|---|---|---|---|---|---|---|
|Ala|Lys|Glu|Ser 900|Val|Asp|Ala|Leu|Phe 905|Val|Asn|Ser|Gln|Tyr 910|Asp|Gln|

Ala Lys Glu Ser Val Asp Ala Leu Phe Val Asn Ser Gln Tyr Asp Gln
             900                 905                 910

Leu Gln Ala Asp Thr Asn Ile Ala Met Ile His Ala Ala Asp Lys Arg
             915                 920                 925

Val His Arg Ile Arg Glu Ala Tyr Leu Pro Glu Leu Ser Val Ile Pro
             930                 935                 940

Gly Val Asn Val Asp Ile Phe Glu Glu Leu Lys Gly Arg Ile Phe Thr
945                  950                 955                 960

Ala Phe Phe Leu Tyr Asp Ala Arg Asn Val Ile Lys Asn Gly Asp Phe
                 965                 970                 975

Asn Asn Gly Leu Ser Cys Trp Asn Val Lys Gly His Val Asp Val Glu
             980                 985                 990

Glu Gln Asn Asn His Arg Ser Val Leu Val Val Pro Glu Trp Glu Ala
             995                 1000                1005

Glu Val Ser Gln Glu Val Arg Val Cys Pro Gly Arg Gly Tyr Ile Leu
    1010                1015                1020

Arg Val Thr Ala Tyr Lys Glu Gly Tyr Gly Glu Gly Cys Val Thr Ile
1025                1030                1035                1040

His Glu Ile Glu Asn Asn Thr Asp Glu Leu Lys Phe Ser Asn Cys Val
             1045                1050                1055

Glu Glu Glu Val Tyr Pro Asn Asn Thr Val Thr Cys Asn Asp Tyr Thr
    1060                1065                1070

Ala Asn Gln Glu Glu Tyr Gly Gly Ala Tyr Thr Ser Arg Asn Arg Gly
    1075                1080                1085

Tyr Asp Glu Thr Tyr Gly Ser Asn Ser Ser Val Pro Ala Asp Tyr Ala
    1090                1095                1100

Ser Val Tyr Glu Glu Lys Ser Tyr Thr Asp Gly Arg Arg Asp Asn Pro
1105                1110                1115                1120

Cys Glu Ser Asn Arg Gly Tyr Gly Asp Tyr Thr Pro Leu Pro Ala Gly
                1125                1130                1135

Tyr Val Thr Lys Glu Leu Glu Tyr Phe Pro Glu Thr Asp Lys Val Trp
             1140                1145                1150

Ile Glu Ile Gly Glu Thr Glu Gly Thr Phe Ile Val Asp Ser Val Glu
             1155                1160                1165

Leu Leu Leu Met Glu Glu
1170

( 2 ) INFORMATION FOR SEQ ID NO:26:

( i ) SEQUENCE CHARACTERISTICS:
        ( A ) LENGTH: 3444 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

```
ATGGAAAATA ATATTCAAAA TCAATGCGTA CCTTACAATT GTTTAAATAA TCCTGAAGTA      60
GAAATACTGA ACGAAGAACG CAGCACCGGC CGCCTGCCGC TGGACATCAG CCTGAGCCTT     120
ACACGTTTCC TTTTGAGTGA ATTTGTTCCA GGTGTGGGAG TTGCGTTTGG ATTATTTGAT     180
TTAATATGGG GTTTTATAAC TCCTTCTGAT GGAGCTTAT TTCTTTTACA GATTGAACAA      240
TTGATTGAGC AAAGAATAGA AACATTGGAA AGGAACCGGG CAATTACTAC ATTACGAGGG     300
TTAGCAGATA GCTATGAAAT TTATATTGAA GCACTAAGAG AGTGGGAAGC AAATCCTAAT     360
AATGCACAAT TAAGGGAAGA TGTGCGTATT CGATTGCTA ATACAGACGA CGCTTTAATA      420
ACAGCAATAA ATAATTTTAC ACTTACAAGT TTTGAAATCC CTCTTTTATC GGTCTATGTT     480
```

| 63 | | | | 64 | | |
|---|---|---|---|---|---|---|
| CAAGCGGCGA | ATTTACATTT | ATCACTATTA | AGAGACGCTG | TATCGTTTGG | GCAGGGTTGG | 540 |
| GGACTGGATA | TAGCTACTGT | TAATAATCAT | TATAATAGAT | TAATAAATCT | TATTCATAGA | 600 |
| TATACGAAAC | ATTGTTTGGA | CACATACAAT | CAAGGATTAG | AAAACTTAAG | AGGTACTAAT | 660 |
| ACTCGACAAT | GGGCAAGATT | CAATCAGTTT | AGGAGAGATT | TAACACTTAC | TGTATTAGAT | 720 |
| ATCGTTGCTC | TTTTTCCGAA | CTACGATGTT | AGAACATATC | CAATTCAAAC | GTCATCCCAA | 780 |
| TTAACAAGGG | AAATTTATAC | AAGTTCAGTA | ATTGAGGATT | CTCCAGTTTC | TGCTAATATA | 840 |
| CCTAATGGTT | TTAATAGGGC | GGAATTTGGA | GTTAGACCGC | CCCATCTTAT | GGACTTTATG | 900 |
| AATTCTTTGT | TTGTAACTGC | AGAGACTGTT | AGAAGTCAAA | CTGTGTGGGG | AGGACACTTA | 960 |
| GTTAGTTCAC | GAAATACGGC | TGGTAACCGT | ATAAATTTCC | CTAGTTACGG | GGTCTTCAAT | 1020 |
| CCTGGTGGCG | CCATTTGGAT | TGCAGATGAG | GATCCACGTC | CTTTTATCG | GACATTATCA | 1080 |
| GATCCTGTTT | TGTCCGAGG | AGGATTTGGG | AATCCTCATT | ATGTACTGGG | GCTTAGGGGA | 1140 |
| GTAGCATTTC | AACAAACTGG | TACGAACCAC | ACCCGAACAT | TTAGAAATAG | TGGGACCATA | 1200 |
| GATTCTCTAG | ATGAAATCCC | ACCTCAGGAT | AATAGTGGGG | CACCTTGGAA | TGATTATAGT | 1260 |
| CATGTATTAA | ATCATGTTAC | ATTTGTACGA | TGGCCAGGTG | AGATTTCAGG | AAGTGATTCA | 1320 |
| TGGAGAGCTC | CAATGTTTTC | TTGGACGCAC | CGTAGTGCAA | CCCCTACAAA | TACAATTGAT | 1380 |
| CCGGAGAGGA | TTACTCAAAT | ACCATTGGTA | AAAGCACATA | CACTTCAGTC | AGGTACTACT | 1440 |
| GTTGTAAGAG | GGCCCGGGTT | TACGGGAGGA | GATATTCTTC | GACGAACAAG | TGGAGGACCA | 1500 |
| TTTGCTTATA | CTATTGTTAA | TATAAATGGG | CAATTACCCC | AAAGGTATCG | TGCAAGAATA | 1560 |
| CGCTATGCCT | CTACTACAAA | TCTAAGAATT | TACGTAACGG | TTGCAGGTGA | ACGGATTTT | 1620 |
| GCTGGTCAAT | TTAACAAAAC | AATGGATACC | GGTGACCCAT | TAACATTCCA | ATCTTTTAGT | 1680 |
| TACGCAACTA | TTAATACAGC | TTTTACATTC | CCAATGAGCC | AGAGTAGTTT | CACAGTAGGT | 1740 |
| GCTGATACTT | TTAGTTCAGG | GAATGAAGTT | TATATAGACA | GATTTGAATT | GATTCCAGTT | 1800 |
| ACTGCAACAT | TTGAAGCAGA | ATATGATTTA | GAAAGAGCAC | AAAAGGCGGT | GAATGCGCTG | 1860 |
| TTTACTTCTA | TAAACCAAAT | AGGGATAAAA | ACAGATGTGA | CGGATTATCA | TATCGATCGA | 1920 |
| GTATCCAATT | TAGTTGAGTG | TTTATCTGAT | GAATTTTGTC | TGGATGAAAA | AAAAGAATTG | 1980 |
| TCCGAGAAAG | TCAAACATGC | GAAGCGACTT | AGTGATGAGC | GGAATTTACT | TCAAGATCCA | 2040 |
| AACTTTAGAG | GGATCAATAG | ACAACTAGAC | CGTGGCTGGA | GAGGAAGTAC | GGATATTACC | 2100 |
| ATCCAAGGAG | GCGATGACGT | ATTCAAAGAG | AATTACGTTA | CGCTATTGGG | TACCTTTGAT | 2160 |
| GAGTGCTATC | CAACGTATTT | ATATCAAAAA | ATAGATGAGT | CGAAATTAAA | AGCCTATACC | 2220 |
| CGTTACCAAT | TAAGAGGGTA | TATCGAAGAT | AGTCAAGACT | TAGAAATCTA | TTTAATTCGC | 2280 |
| TACAATGCCA | AACACGAAAC | AGTAAATGTG | CCAGGTACGG | GTTCCTTATG | GCCGCTTTCA | 2340 |
| GCCCCAAGTC | CAATCGGAAA | ATGTGCCCAT | CATTCCCATC | ATTTCTCCTT | GGACATTGAT | 2400 |
| GTTGGATGTA | CAGACTTAAA | TGAGGACTTA | GGTGTATGGG | TGATATTCAA | GATTAAGACG | 2460 |
| CAAGATGGCC | ATGCAAGACT | AGGAAATCTA | GAATTTCTCG | AAGAGAAACC | ATTAGTAGGA | 2520 |
| GAAGCACTAG | CTCGTGTGAA | AAGAGCGGAG | AAAAAATGGA | GAGACAAACG | TGAAAAATTG | 2580 |
| GAATGGGAAA | CAAATATTGT | TTATAAAGAG | GCAAAGAAT | CTGTAGATGC | TTTATTTGTA | 2640 |
| AACTCTCAAT | ATGATAGATT | ACAAGCGGAT | ACCAACATCG | CGATGATTCA | TGCGGCAGAT | 2700 |
| AAACGCGTTC | ATAGCATTCG | AGAAGCTTAT | CTGCCTGAGC | TGTCTGTGAT | TCCGGGTGTC | 2760 |
| AATGCGGCTA | TTTTTGAAGA | ATTAGAAGGG | CGTATTTTCA | CTGCATTCTC | CCTATATGAT | 2820 |
| GCGAGAAATG | TCATTAAAAA | TGGTGATTTT | AATAATGGCT | TATCCTGCTG | GAACGTGAAA | 2880 |
| GGGCATGTAG | ATGTAGAAGA | ACAAAACAAC | CACCGTTCGG | TCCTTGTTGT | TCCGGAATGG | 2940 |
| GAAGCAGAAG | TGTCACAAGA | AGTTCGTGTC | TGTCCGGGTC | GTGGCTATAT | CCTTCGTGTC | 3000 |

```
ACAGCGTACA AGGAGGGATA TGGAGAAGGT TGCGTAACCA TTCATGAGAT CGAGAACAAT    3060
ACAGACGAAC TGAAGTTTAG CAACTGTGTA GAAGAGGAAG TATATCCAAA CAACACGGTA    3120
ACGTGTAATG ATTATACTGC GACTCAAGAA GAATATGAGG GTACGTACAC TTCTCGTAAT    3180
CGAGGATATG ACGGAGCCTA TGAAAGCAAT TCTTCTGTAC AGCTGATTA TGCATCAGCC     3240
TATGAAGAAA AAGCATATAC AGATGGACGA AGAGACAATC CTTGTGAATC TAACAGAGGA    3300
TATGGGGATT ACACACCACT ACCAGCTGGC TATGTGACAA AGAATTAGA GTACTTCCCA     3360
GAAACCGATA AGGTATGGAT TGAGATCGGA GAAACGGAAG GAACATTCAT CGTGGACAGC    3420
GTGGAATTAC TTCTTATGGA GGAA                                           3444
```

(2) INFORMATION FOR SEQ ID NO:27:

(i) SEQUENCE CHARACTERISTICS:
        (A) LENGTH: 1148 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:27:

```
Met Glu Asn Asn Ile Gln Asn Gln Cys Val Pro Tyr Asn Cys Leu Asn
 1               5                  10                  15

Asn Pro Glu Val Glu Ile Leu Asn Glu Glu Arg Ser Thr Gly Arg Leu
                20                  25                  30

Pro Leu Asp Ile Ser Leu Ser Leu Thr Arg Phe Leu Leu Ser Glu Phe
            35                  40                  45

Val Pro Gly Val Gly Val Ala Phe Gly Leu Phe Asp Leu Ile Trp Gly
    50                  55                  60

Phe Ile Thr Pro Ser Asp Trp Ser Leu Phe Leu Leu Gln Ile Glu Gln
 65                  70                  75                  80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Ile Tyr Ile Glu Ala Leu
               100                 105                 110

Arg Glu Trp Glu Ala Asn Pro Asn Asn Ala Gln Leu Arg Glu Asp Val
           115                 120                 125

Arg Ile Arg Phe Ala Asn Thr Asp Asp Ala Leu Ile Thr Ala Ile Asn
   130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
               165                 170                 175

Gly Gln Gly Trp Gly Leu Asp Ile Ala Thr Val Asn Asn His Tyr Asn
           180                 185                 190

Arg Leu Ile Asn Leu Ile His Arg Tyr Thr Lys His Cys Leu Asp Thr
   195                 200                 205

Tyr Asn Gln Gly Leu Glu Asn Leu Arg Gly Thr Asn Thr Arg Gln Trp
   210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
               245                 250                 255

Thr Ser Ser Gln Leu Thr Arg Glu Ile Tyr Thr Ser Ser Val Ile Glu
           260                 265                 270

Asp Ser Pro Val Ser Ala Asn Ile Pro Asn Gly Phe Asn Arg Ala Glu
   275                 280                 285
```

| Phe | Gly | Val | Arg | Pro | Pro | His | Leu | Met | Asp | Phe | Met | Asn | Ser | Leu | Phe |
|---|---|---|---|---|---|---|---|---|---|---|---|---|---|---|---|
| 290 | | | | | 295 | | | | 300 | | | | | | |

| Val | Thr | Ala | Glu | Thr | Val | Arg | Ser | Gln | Thr | Val | Trp | Gly | Gly | His | Leu |
| 305 | | | | 310 | | | | | 315 | | | | | | 320 |

| Val | Ser | Ser | Arg | Asn | Thr | Ala | Gly | Asn | Arg | Ile | Asn | Phe | Pro | Ser | Tyr |
| | | | | 325 | | | | | 330 | | | | | 335 | |

| Gly | Val | Phe | Asn | Pro | Gly | Gly | Ala | Ile | Trp | Ile | Ala | Asp | Glu | Asp | Pro |
| | | | 340 | | | | | 345 | | | | | 350 | | |

| Arg | Pro | Phe | Tyr | Arg | Thr | Leu | Ser | Asp | Pro | Val | Phe | Val | Arg | Gly | Gly |
| | | | 355 | | | | | 360 | | | | | 365 | | |

| Phe | Gly | Asn | Pro | His | Tyr | Val | Leu | Gly | Leu | Arg | Gly | Val | Ala | Phe | Gln |
| | 370 | | | | | 375 | | | | | 380 | | | | |

| Gln | Thr | Gly | Thr | Asn | His | Thr | Arg | Thr | Phe | Arg | Asn | Ser | Gly | Thr | Ile |
| 385 | | | | | 390 | | | | | 395 | | | | | 400 |

| Asp | Ser | Leu | Asp | Glu | Ile | Pro | Pro | Gln | Asp | Asn | Ser | Gly | Ala | Pro | Trp |
| | | | | 405 | | | | | 410 | | | | | 415 | |

| Asn | Asp | Tyr | Ser | His | Val | Leu | Asn | His | Val | Thr | Phe | Val | Arg | Trp | Pro |
| | | | 420 | | | | | 425 | | | | | 430 | | |

| Gly | Glu | Ile | Ser | Gly | Ser | Asp | Ser | Trp | Arg | Ala | Pro | Met | Phe | Ser | Trp |
| | | | 435 | | | | | 440 | | | | | 445 | | |

| Thr | His | Arg | Ser | Ala | Thr | Pro | Thr | Asn | Thr | Ile | Asp | Pro | Glu | Arg | Ile |
| | 450 | | | | | 455 | | | | | 460 | | | | |

| Thr | Gln | Ile | Pro | Leu | Val | Lys | Ala | His | Thr | Leu | Gln | Ser | Gly | Thr | Thr |
| 465 | | | | | 470 | | | | | 475 | | | | | 480 |

| Val | Val | Arg | Gly | Pro | Gly | Phe | Thr | Gly | Gly | Asp | Ile | Leu | Arg | Arg | Thr |
| | | | | 485 | | | | | 490 | | | | | 495 | |

| Ser | Gly | Gly | Pro | Phe | Ala | Tyr | Thr | Ile | Val | Asn | Ile | Asn | Gly | Gln | Leu |
| | | | 500 | | | | | 505 | | | | | 510 | | |

| Pro | Gln | Arg | Tyr | Arg | Ala | Arg | Ile | Arg | Tyr | Ala | Ser | Thr | Thr | Asn | Leu |
| | | | 515 | | | | | 520 | | | | | 525 | | |

| Arg | Ile | Tyr | Val | Thr | Val | Ala | Gly | Glu | Arg | Ile | Phe | Ala | Gly | Gln | Phe |
| | | | 530 | | | | | 535 | | | | | 540 | | |

| Asn | Lys | Thr | Met | Asp | Thr | Gly | Asp | Pro | Leu | Thr | Phe | Gln | Ser | Phe | Ser |
| 545 | | | | | 550 | | | | | 555 | | | | | 560 |

| Tyr | Ala | Thr | Ile | Asn | Thr | Ala | Phe | Thr | Phe | Pro | Met | Ser | Gln | Ser | Ser |
| | | | | 565 | | | | | 570 | | | | | 575 | |

| Phe | Thr | Val | Gly | Ala | Asp | Thr | Phe | Ser | Ser | Gly | Asn | Glu | Val | Tyr | Ile |
| | | | 580 | | | | | 585 | | | | | 590 | | |

| Asp | Arg | Phe | Glu | Leu | Ile | Pro | Val | Thr | Ala | Thr | Phe | Glu | Ala | Glu | Tyr |
| | | 595 | | | | | 600 | | | | | 605 | | | |

| Asp | Leu | Glu | Arg | Ala | Gln | Lys | Ala | Val | Asn | Ala | Leu | Phe | Thr | Ser | Ile |
| | 610 | | | | | 615 | | | | | 620 | | | | |

| Asn | Gln | Ile | Gly | Ile | Lys | Thr | Asp | Val | Thr | Asp | Tyr | His | Ile | Asp | Arg |
| 625 | | | | | 630 | | | | | 635 | | | | | 640 |

| Val | Ser | Asn | Leu | Val | Glu | Cys | Leu | Ser | Asp | Glu | Phe | Cys | Leu | Asp | Glu |
| | | | | 645 | | | | | 650 | | | | | 655 | |

| Lys | Lys | Glu | Leu | Ser | Glu | Lys | Val | Lys | His | Ala | Lys | Arg | Leu | Ser | Asp |
| | | | 660 | | | | | 665 | | | | | 670 | | |

| Glu | Arg | Asn | Leu | Leu | Gln | Asp | Pro | Asn | Phe | Arg | Gly | Ile | Asn | Arg | Gln |
| | | 675 | | | | | 680 | | | | | 685 | | | |

| Leu | Asp | Arg | Gly | Trp | Arg | Gly | Ser | Thr | Asp | Ile | Thr | Ile | Gln | Gly | Gly |
| | 690 | | | | | 695 | | | | | 700 | | | | |

| Asp | Asp | Val | Phe | Lys | Glu | Asn | Tyr | Val | Thr | Leu | Leu | Gly | Thr | Phe | Asp |
| 705 | | | | | 710 | | | | | 715 | | | | | 720 |

| Glu | Cys | Tyr | Pro | Thr | Tyr | Leu | Tyr | Gln | Lys | Ile | Asp | Glu | Ser | Lys | Leu |

725                                    730                                   735
Lys   Ala   Tyr   Thr   Arg   Tyr   Gln   Leu   Arg   Gly   Tyr   Ile   Glu   Asp   Ser   Gln
                  740                           745                     750
Asp   Leu   Glu   Ile   Tyr   Leu   Ile   Arg   Tyr   Asn   Ala   Lys   His   Glu   Thr   Val
            755                           760                           765
Asn   Val   Pro   Gly   Thr   Gly   Ser   Leu   Trp   Pro   Leu   Ser   Ala   Pro   Ser   Pro
      770                           775                           780
Ile   Gly   Lys   Cys   Ala   His   His   Ser   His   His   Phe   Ser   Leu   Asp   Ile   Asp
785                           790                           795                           800
Val   Gly   Cys   Thr   Asp   Leu   Asn   Glu   Asp   Leu   Gly   Val   Trp   Val   Ile   Phe
                        805                           810                           815
Lys   Ile   Lys   Thr   Gln   Asp   Gly   His   Ala   Arg   Leu   Gly   Asn   Leu   Glu   Phe
                  820                           825                           830
Leu   Glu   Glu   Lys   Pro   Leu   Val   Gly   Glu   Ala   Leu   Ala   Arg   Val   Lys   Arg
            835                           840                           845
Ala   Glu   Lys   Lys   Trp   Arg   Asp   Lys   Arg   Glu   Lys   Leu   Glu   Trp   Glu   Thr
      850                           855                           860
Asn   Ile   Val   Tyr   Lys   Glu   Ala   Lys   Glu   Ser   Val   Asp   Ala   Leu   Phe   Val
865                           870                           875                           880
Asn   Ser   Gln   Tyr   Asp   Arg   Leu   Gln   Ala   Asp   Thr   Asn   Ile   Ala   Met   Ile
                        885                           890                           895
His   Ala   Ala   Asp   Lys   Arg   Val   His   Ser   Ile   Arg   Glu   Ala   Tyr   Leu   Pro
                  900                           905                           910
Glu   Leu   Ser   Val   Ile   Pro   Gly   Val   Asn   Ala   Ala   Ile   Phe   Glu   Glu   Leu
            915                           920                           925
Glu   Gly   Arg   Ile   Phe   Thr   Ala   Phe   Ser   Leu   Tyr   Asp   Ala   Arg   Asn   Val
      930                           935                           940
Ile   Lys   Asn   Gly   Asp   Phe   Asn   Asn   Gly   Leu   Ser   Cys   Trp   Asn   Val   Lys
945                           950                           955                           960
Gly   His   Val   Asp   Val   Glu   Glu   Gln   Asn   Asn   His   Arg   Ser   Val   Leu   Val
                        965                           970                           975
Val   Pro   Glu   Trp   Glu   Ala   Glu   Val   Ser   Gln   Glu   Val   Arg   Val   Cys   Pro
                  980                           985                           990
Gly   Arg   Gly   Tyr   Ile   Leu   Arg   Val   Thr   Ala   Tyr   Lys   Glu   Gly   Tyr   Gly
            995                           1000                          1005
Glu   Gly   Cys   Val   Thr   Ile   His   Glu   Ile   Glu   Asn   Asn   Thr   Asp   Glu   Leu
      1010                          1015                          1020
Lys   Phe   Ser   Asn   Cys   Val   Glu   Glu   Val   Tyr   Pro   Asn   Asn   Thr   Val
1025                          1030                          1035                          1040
Thr   Cys   Asn   Asp   Tyr   Thr   Ala   Thr   Gln   Glu   Glu   Tyr   Glu   Gly   Thr   Tyr
                        1045                          1050                          1055
Thr   Ser   Arg   Asn   Arg   Gly   Tyr   Asp   Gly   Ala   Tyr   Glu   Ser   Asn   Ser   Ser
                  1060                          1065                          1070
Val   Pro   Ala   Asp   Tyr   Ala   Ser   Ala   Tyr   Glu   Glu   Lys   Ala   Tyr   Thr   Asp
            1075                          1080                          1085
Gly   Arg   Arg   Asp   Asn   Pro   Cys   Glu   Ser   Asn   Arg   Gly   Tyr   Gly   Asp   Tyr
      1090                          1095                          1100
Thr   Pro   Leu   Pro   Ala   Gly   Tyr   Val   Thr   Lys   Glu   Leu   Glu   Tyr   Phe   Pro
1105                          1110                          1115                          1120
Glu   Thr   Asp   Lys   Val   Trp   Ile   Glu   Ile   Gly   Glu   Thr   Glu   Gly   Thr   Phe
                        1125                          1130                          1135
Ile   Val   Asp   Ser   Val   Glu   Leu   Leu   Leu   Met   Glu   Glu
                  1140                          1145

( 2 ) INFORMATION FOR SEQ ID NO:28:

(i) SEQUENCE CHARACTERISTICS:
   (A) LENGTH: 3522 base pairs
   (B) TYPE: nucleic acid
   (C) STRANDEDNESS: single
   (D) TOPOLOGY: linear (ii) MOLECULE TYPE: DNA (genomic)

(xi) SEQUENCE DESCRIPTION: SEQ ID NO:28:

| | | | | | | |
|---|---|---|---|---|---|---|
| ATGGAAAATA | ATATTCAAAA | TCAATGCGTA | CCTTACAATT | GTTTAAATAA | TCCTGAAGTA | 60 |
| GAAATACTGA | ACGAAGAACG | CAGCACCGGC | CGCCTGCCGC | TGGACATCAG | CCTGAGCCTT | 120 |
| ACACGTTTCC | TTTTGAGTGA | ATTTGTTCCA | GGTGTGGGAG | TTGCGTTTGG | ATTATTTGAT | 180 |
| TTAATATGGG | GTTTTATAAC | TCCTTCTGAT | TGGAGCTTAT | TTCTTTTACA | GATTGAACAA | 240 |
| TTGATTGAGC | AAAGAATAGA | AACATTGGAA | AGGAACCGGG | CAATTACTAC | ATTACGAGGG | 300 |
| TTAGCAGATA | GCTATGAAAT | TTATATTGAA | GCACTAAGAG | AGTGGGAAGC | AAATCCTAAT | 360 |
| AATGCACAAT | TAAGGGAAGA | TGTGCGTATT | CGATTTGCTA | ATACAGACGA | CGCTTTAATA | 420 |
| ACAGCAATAA | ATAATTTTAC | ACTTACAAGT | TTTGAAATCC | CTCTTTATC | GGTCTATGTT | 480 |
| CAAGCGGCGA | ATTTACATTT | ATCACTATTA | AGAGACGCTG | TATCGTTTGG | GCAGGGTTGG | 540 |
| GGACTGGATA | TAGCTACTGT | TAATAATCAT | ATAATAGAT | TAATAAATCT | TATTCATAGA | 600 |
| TATACGAAAC | ATTGTTTGGA | CACATACAAT | CAAGGATTAG | AAAACTTAAG | AGGTACTAAT | 660 |
| ACTCGACAAT | GGGCAAGATT | CAATCAGTTT | AGGAGAGATT | TAACACTTAC | TGTATTAGAT | 720 |
| ATCGTTGCTC | TTTTTCCGAA | CTACGATGTT | AGAACATATC | CAATTCAAAC | GTCATCCCAA | 780 |
| TTAACAAGGG | AAATTTATAC | AAGTTCAGTA | ATTGAGGATT | CTCCAGTTTC | TGCTAATATA | 840 |
| CCTAATGGTT | TTAATAGGGC | GGAATTTGGA | GTTAGACCGC | CCCATCTTAT | GGACTTTATG | 900 |
| AATTCTTTGT | TTGTAACTGC | AGAGACTGTT | AGAAGTCAAA | CTGTGTGGGG | AGGACACTTA | 960 |
| GTTAGTTCAC | GAAATACGGC | TGGTAACCGT | ATAAATTTCC | CTAGTTACGG | GGTCTTCAAT | 1020 |
| CCTGGTGGCG | CCATTTGGAT | TGCAGATGAG | GATCCACGTC | CTTTTATCG | GACATTATCA | 1080 |
| GATCCTGTTT | TTGTCCGAGG | AGGATTTGGG | AATCCTCATT | ATGTACTGGG | GCTTAGGGGA | 1140 |
| GTAGCATTTC | AACAAACTGG | TACGAACCAC | ACCCGAACAT | TTAGAAATAG | TGGGACCATA | 1200 |
| GATTCTCTAG | ATGAAATCCC | ACCTCAGGAT | AATAGTGGGG | CACCTTGGAA | TGATTATAGT | 1260 |
| CATGTATTAA | ATCATGTTAC | ATTTGTACGA | TGGCCAGGTG | AGATTTCAGG | AAGTGATTCA | 1320 |
| TGGAGAGCTC | CAATGTTTTC | TTGGACGCAC | CGTAGTGCAA | CCCCTACAAA | TACAATTGAT | 1380 |
| CCGGAGAGGA | TTACTCAAAT | ACCATTGGTA | AAAGCACATA | CACTTCAGTC | AGGTACTACT | 1440 |
| GTTGTAAGAG | GGCCCGGGTT | TACGGGAGGA | GATATTCTTC | GACGAACAAG | TGGAGGACCA | 1500 |
| TTTGCTTATA | CTATTGTTAA | TATAAATGGG | CAATTACCCC | AAAGGTATCG | TGCAAGAATA | 1560 |
| CGCTATGCCT | CTACTACAAA | TCTAAGAATT | TACGTAACGG | TTGCAGGTGA | ACGGATTTTT | 1620 |
| GCTGGTCAAT | TTAACAAAAC | AATGGATACC | GGTGACCCAT | TAACATTCCA | ATCTTTTAGT | 1680 |
| TACGCAACTA | TTAATACAGC | TTTTACATTC | CCAATGAGCC | AGAGTAGTTT | CACAGTAGGT | 1740 |
| GCTGATACTT | TTAGTTCAGG | GAATGAAGTT | TATATAGACA | GATTTGAATT | GATTCCAGTT | 1800 |
| ACTGCAACAT | TTGAAGCAGA | ATATGATTTA | GAAAGAGCAC | AAAAGGCGGT | GAATGCGCTG | 1860 |
| TTTACTTCTA | TAAACCAAAT | AGGGATAAAA | ACAGATGTGA | CGGATTATCA | TATCGATCGA | 1920 |
| GTGTCCAATT | TAGTTACGTA | TTTATCGGAT | GAATTTTGTC | TGGATGAAAA | GCGAGAATTG | 1980 |
| TCCGAGAAAG | TCAAACATGC | GAAGCGACTC | AGTGATGAAC | GCAATTTACT | CCAAGATTCA | 2040 |
| AATTTCAAAG | ACATTAATAG | GCAACCAGAA | CGTGGGTGGG | GCGGAAGTAC | AGGGATTACC | 2100 |
| ATCCAAGGAG | GGGATGACGT | ATTTAAAGAA | AATTACGTCA | CACTATCAGG | TACCTTTGAT | 2160 |
| GAGTGCTATC | CAACATATTT | GTATCAAAAA | ATCGATGAAT | CAAAATTAAA | AGCCTTTACC | 2220 |

| | | | | |
|---|---|---|---|---|
| CGTTATCAAT | TAAGAGGGTA | TATCGAAGAT | AGTCAAGACT | TAGAAATCTA TTTAATTCGC | 2280 |
| TACAATGCAA | AACATGAAAC | AGTAAATGTG | CCAGGTACGG | GTTCCTTATG GCCGCTTTCA | 2340 |
| GCCCAAAGTC | CAATCGGAAA | GTGTGGAGAG | CCGAATCGAT | GCGCGCCACA CCTTGAATGG | 2400 |
| AATCCTGACT | TAGATTGTTC | GTGTAGGGAT | GGAGAAAAGT | GTGCCCATCA TTCGCATCAT | 2460 |
| TTCTCCTTAG | ACATTGATGT | AGGATGTACA | GACTTAAATG | AGGACCTAGG TGTATGGGTG | 2520 |
| ATCTTTAAGA | TTAAGACGCA | AGATGGGCAC | GCAAGACTAG | GAATCTAGA GTTTCTCGAA | 2580 |
| GAGAAACCAT | TAGTAGGAGA | AGCGCTAGCT | CGTGTGAAAA | GAGCGGAGAA AAAATGGAGA | 2640 |
| GACAAACGTG | AAAAATTGGA | ATGGGAAACA | AATATCGTTT | ATAAAGAGGC AAAAGAATCT | 2700 |
| GTAGATGCTT | TATTTGTAAA | CTCTCAATAT | GATCAATTAC | AAGCGGATAC GAATATTGCC | 2760 |
| ATGATTCATG | CGGCAGATAA | ACGTGTTCAT | AGCATTCGAG | AAGCTTATCT GCCTGAGCTG | 2820 |
| TCTGTGATTC | CGGGTGTCAA | TGCGGCTATT | TTTGAAGAAT | TAGAAGGGCG TATTTTCACT | 2880 |
| GCATTCTCCC | TATATGATGC | GAGAAATGTC | ATTAAAAATG | GTGATTTTAA TAATGGCTTA | 2940 |
| TCCTGCTGGA | ACGTGAAAGG | GCATGTAGAT | GTAGAAGAAC | AAAACAACCA CCGTTCGGTC | 3000 |
| CTTGTTGTTC | CGGAATGGGA | AGCAGAAGTG | TCACAAGAAG | TTCGTGTCTG TCCGGGTCGT | 3060 |
| GGCTATATCC | TTCGTGTCAC | AGCGTACAAG | GAGGGATATG | GAGAAGGTTG CGTAACCATT | 3120 |
| CATGAGATCG | AGAACAATAC | AGACGAACTG | AAGTTTAGCA | ACTGTGTAGA AGAGGAAGTA | 3180 |
| TATCCAAACA | ACACGGTAAC | GTGTAATGAT | TATACTGCGA | CTCAAGAAGA ATATGAGGGT | 3240 |
| ACGTACACTT | CTCGTAATCG | AGGATATGAC | GGAGCCTATG | AAAGCAATTC TTCTGTACCA | 3300 |
| GCTGATTATG | CATCAGCCTA | TGAAGAAAAA | GCATATACAG | ATGGACGAAG AGACAATCCT | 3360 |
| TGTGAATCTA | ACAGAGGATA | TGGGGATTAC | ACACCACTAC | CAGCTGGCTA TGTGACAAAA | 3420 |
| GAATTAGAGT | ACTTCCCAGA | AACCGATAAG | GTATGGATTG | AGATCGGAGA AACGGAAGGA | 3480 |
| ACATTCATCG | TGGACAGCGT | GGAATTACTT | CTTATGGAGG | AA | 3522 |

( 2 ) INFORMATION FOR SEQ ID NO:29:

( i ) SEQUENCE CHARACTERISTICS:
        ( A ) LENGTH: 1174 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:29:

```
Met Glu Asn Asn Ile Gln Asn Gln Cys Val Pro Tyr Asn Cys Leu Asn
 1               5                  10                  15

Asn Pro Glu Val Glu Ile Leu Asn Glu Glu Arg Ser Thr Gly Arg Leu
            20                  25                  30

Pro Leu Asp Ile Ser Leu Ser Leu Thr Arg Phe Leu Leu Ser Glu Phe
        35                  40                  45

Val Pro Gly Val Gly Val Ala Phe Gly Leu Phe Asp Leu Ile Trp Gly
    50                  55                  60

Phe Ile Thr Pro Ser Asp Trp Ser Leu Phe Leu Leu Gln Ile Glu Gln
65                  70                  75                  80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
```

|  | 130 |  |  |  | 135 |  |  |  | 140 |  |  |  |
|---|---|---|---|---|---|---|---|---|---|---|---|---|

Asn Phe Thr Leu Thr Ser Phe Glu Ile Pro Leu Leu Ser Val Tyr Val
145                                 150                           155                     160

Gln Ala Ala Asn Leu His Leu Ser Leu Leu Arg Asp Ala Val Ser Phe
                  165                     170                         175

Gly Gln Gly Trp Gly Leu Asp Ile Ala Thr Val Asn Asn His Tyr Asn
               180                   185                    190

Arg Leu Ile Asn Leu Ile His Arg Tyr Thr Lys His Cys Leu Asp Thr
        195                  200                205

Tyr Asn Gln Gly Leu Glu Asn Leu Arg Gly Thr Asn Thr Arg Gln Trp
210                      215                   220

Ala Arg Phe Asn Gln Phe Arg Arg Asp Leu Thr Leu Thr Val Leu Asp
225                230                 235                240

Ile Val Ala Leu Phe Pro Asn Tyr Asp Val Arg Thr Tyr Pro Ile Gln
               245                   250               255

Thr Ser Ser Gln Leu Thr Arg Glu Ile Tyr Thr Ser Ser Val Ile Glu
            260                265              270

Asp Ser Pro Val Ser Ala Asn Ile Pro Asn Gly Phe Asn Arg Ala Glu
        275               280                 285

Phe Gly Val Arg Pro Pro His Leu Met Asp Phe Met Asn Ser Leu Phe
    290                 295                   300

Val Thr Ala Glu Thr Val Arg Ser Gln Thr Val Trp Gly Gly His Leu
305                  310                315               320

Val Ser Ser Arg Asn Thr Ala Gly Asn Arg Ile Asn Phe Pro Ser Tyr
               325                330              335

Gly Val Phe Asn Pro Gly Gly Ala Ile Trp Ile Ala Asp Glu Asp Pro
            340                345             350

Arg Pro Phe Tyr Arg Thr Leu Ser Asp Pro Val Phe Val Arg Gly Gly
        355                  360                365

Phe Gly Asn Pro His Tyr Val Leu Gly Leu Arg Gly Val Ala Phe Gln
    370                 375                  380

Gln Thr Gly Thr Asn His Thr Arg Thr Phe Arg Asn Ser Gly Thr Ile
385                  390                395              400

Asp Ser Leu Asp Glu Ile Pro Pro Gln Asp Asn Ser Gly Ala Pro Trp
            405                410              415

Asn Asp Tyr Ser His Val Leu Asn His Val Thr Phe Val Arg Trp Pro
            420                425             430

Gly Glu Ile Ser Gly Ser Asp Ser Trp Arg Ala Pro Met Phe Ser Trp
        435                 440                445

Thr His Arg Ser Ala Thr Pro Thr Asn Thr Ile Asp Pro Glu Arg Ile
450                  455                460

Thr Gln Ile Pro Leu Val Lys Ala His Thr Leu Gln Ser Gly Thr Thr
465                  470                475              480

Val Val Arg Gly Pro Gly Phe Thr Gly Gly Asp Ile Leu Arg Arg Thr
            485                490              495

Ser Gly Gly Pro Phe Ala Tyr Thr Ile Val Asn Ile Asn Gly Gln Leu
        500                  505              510

Pro Gln Arg Tyr Arg Ala Arg Ile Arg Tyr Ala Ser Thr Thr Asn Leu
        515                520              525

Arg Ile Tyr Val Thr Val Ala Gly Glu Arg Ile Phe Ala Gly Gln Phe
    530                 535                540

Asn Lys Thr Met Asp Thr Gly Asp Pro Leu Thr Phe Gln Ser Phe Ser
545                  550                555              560

Tyr Ala Thr Ile Asn Thr Ala Phe Thr Phe Pro Met Ser Gln Ser Ser
            565                570             575

| | | | | | | | | | | | | | | |
|---|---|---|---|---|---|---|---|---|---|---|---|---|---|---|
|Phe|Thr|Val|Gly|Ala|Asp|Thr|Phe|Ser|Ser|Gly|Asn|Glu|Val|Tyr|Ile
| | | |580| | | |585| | | |590| | | |
|Asp|Arg|Phe|Glu|Leu|Ile|Pro|Val|Thr|Ala|Thr|Phe|Glu|Ala|Glu|Tyr
| | |595| | | |600| | | |605| | | | |
|Asp|Leu|Glu|Arg|Ala|Gln|Lys|Ala|Val|Asn|Ala|Leu|Phe|Thr|Ser|Ile
| |610| | | |615| | | |620| | | | | |
|Asn|Gln|Ile|Gly|Ile|Lys|Thr|Asp|Val|Thr|Asp|Tyr|His|Ile|Asp|Arg
|625| | | |630| | | |635| | | | | | |640
|Val|Ser|Asn|Leu|Val|Thr|Tyr|Leu|Ser|Asp|Glu|Phe|Cys|Leu|Asp|Glu
| | | |645| | | |650| | | | | |655| |
|Lys|Arg|Glu|Leu|Ser|Glu|Lys|Val|Lys|His|Ala|Lys|Arg|Leu|Ser|Asp
| | |660| | | |665| | | |670| | | | |
|Glu|Arg|Asn|Leu|Leu|Gln|Asp|Ser|Asn|Phe|Lys|Asp|Ile|Asn|Arg|Gln
| |675| | | |680| | | |685| | | | | |
|Pro|Glu|Arg|Gly|Trp|Gly|Gly|Ser|Thr|Gly|Ile|Thr|Ile|Gln|Gly|Gly
| |690| | | |695| | | |700| | | | | |
|Asp|Asp|Val|Phe|Lys|Glu|Asn|Tyr|Val|Thr|Leu|Ser|Gly|Thr|Phe|Asp
|705| | | |710| | | |715| | | | | | |720
|Glu|Cys|Tyr|Pro|Thr|Tyr|Leu|Tyr|Gln|Lys|Ile|Asp|Glu|Ser|Lys|Leu
| | | |725| | | |730| | | | | |735| |
|Lys|Ala|Phe|Thr|Arg|Tyr|Gln|Leu|Arg|Gly|Tyr|Ile|Glu|Asp|Ser|Gln
| | |740| | | |745| | | |750| | | | |
|Asp|Leu|Glu|Ile|Tyr|Leu|Ile|Arg|Tyr|Asn|Ala|Lys|His|Glu|Thr|Val
| |755| | | |760| | | |765| | | | | |
|Asn|Val|Pro|Gly|Thr|Gly|Ser|Leu|Trp|Pro|Leu|Ser|Ala|Gln|Ser|Pro
|770| | | |775| | | |780| | | | | | |
|Ile|Gly|Lys|Cys|Gly|Glu|Pro|Asn|Arg|Cys|Ala|Pro|His|Leu|Glu|Trp
|785| | | |790| | | |795| | | | | | |800
|Asn|Pro|Asp|Leu|Asp|Cys|Ser|Cys|Arg|Asp|Gly|Glu|Lys|Cys|Ala|His
| | | |805| | | |810| | | | | |815| |
|His|Ser|His|His|Phe|Ser|Leu|Asp|Ile|Asp|Val|Gly|Cys|Thr|Asp|Leu
| | | |820| | | |825| | | | | |830| |
|Asn|Glu|Asp|Leu|Gly|Val|Trp|Val|Ile|Phe|Lys|Ile|Lys|Thr|Gln|Asp
| | |835| | | |840| | | |845| | | | |
|Gly|His|Ala|Arg|Leu|Gly|Asn|Leu|Glu|Phe|Leu|Glu|Glu|Lys|Pro|Leu
|850| | | |855| | | |860| | | | | | |
|Val|Gly|Glu|Ala|Leu|Ala|Arg|Val|Lys|Arg|Ala|Glu|Lys|Lys|Trp|Arg
|865| | | |870| | | |875| | | | | | |880
|Asp|Lys|Arg|Glu|Lys|Leu|Glu|Trp|Glu|Thr|Asn|Ile|Val|Tyr|Lys|Glu
| | | |885| | | |890| | | | | |895| |
|Ala|Lys|Glu|Ser|Val|Asp|Ala|Leu|Phe|Val|Asn|Ser|Gln|Tyr|Asp|Gln
| | |900| | | |905| | | |910| | | | |
|Leu|Gln|Ala|Asp|Thr|Asn|Ile|Ala|Met|Ile|His|Ala|Ala|Asp|Lys|Arg
| |915| | | |920| | | |925| | | | | |
|Val|His|Ser|Ile|Arg|Glu|Ala|Tyr|Leu|Pro|Glu|Leu|Ser|Val|Ile|Pro
| |930| | | |935| | | |940| | | | | |
|Gly|Val|Asn|Ala|Ala|Ile|Phe|Glu|Glu|Leu|Glu|Gly|Arg|Ile|Phe|Thr
|945| | | |950| | | |955| | | | | | |960
|Ala|Phe|Ser|Leu|Tyr|Asp|Ala|Arg|Asn|Val|Ile|Lys|Asn|Gly|Asp|Phe
| | | |965| | | |970| | | | | |975| |
|Asn|Asn|Gly|Leu|Ser|Cys|Trp|Asn|Val|Lys|Gly|His|Val|Asp|Val|Glu
| | |980| | | | |985| | | | |990| | |
|Glu|Gln|Asn|Asn|His|Arg|Ser|Val|Leu|Val|Val|Pro|Glu|Trp|Glu|Ala
| |995| | | |1000| | | |1005| | | | | |
|Glu|Val|Ser|Gln|Glu|Val|Arg|Val|Cys|Pro|Gly|Arg|Gly|Tyr|Ile|Leu
| |1010| | | |1015| | | |1020| | | | | |

```
Arg Val Thr Ala Tyr Lys Glu Gly Tyr Gly Glu Gly Cys Val Thr Ile
1025                1030                1035                1040

His Glu Ile Glu Asn Asn Thr Asp Glu Leu Lys Phe Ser Asn Cys Val
                1045                1050                1055

Glu Glu Glu Val Tyr Pro Asn Asn Thr Val Thr Cys Asn Asp Tyr Thr
            1060                1065                1070

Ala Thr Gln Glu Glu Tyr Glu Gly Thr Tyr Thr Ser Arg Asn Arg Gly
            1075                1080            1085

Tyr Asp Gly Ala Tyr Glu Ser Asn Ser Ser Val Pro Ala Asp Tyr Ala
            1090            1095            1100

Ser Ala Tyr Glu Glu Lys Ala Tyr Thr Asp Gly Arg Arg Asp Asn Pro
1105            1110            1115            1120

Cys Glu Ser Asn Arg Gly Tyr Gly Asp Tyr Thr Pro Leu Pro Ala Gly
                1125            1130            1135

Tyr Val Thr Lys Glu Leu Glu Tyr Phe Pro Glu Thr Asp Lys Val Trp
            1140            1145            1150

Ile Glu Ile Gly Glu Thr Glu Gly Thr Phe Ile Val Asp Ser Val Glu
            1155            1160            1165

Leu Leu Leu Met Glu Glu
            1170
```

( 2 ) INFORMATION FOR SEQ ID NO:30:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:30:

```
Xaa Xaa Ile Asp Xaa Xaa Glu Xaa Xaa Xaa Xaa Xaa
            5               10
```

( 2 ) INFORMATION FOR SEQ ID NO:31:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:31:

```
Tyr Pro Asn Asn Thr Val Thr Cys
            5
```

( 2 ) INFORMATION FOR SEQ ID NO:32:

( i ) SEQUENCE CHARACTERISTICS:
        ( A ) LENGTH: 1174 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:32:

```
Met Glu Asn Asn Ile Gln Asn Gln Cys Val Pro Tyr Asn Cys Leu Asn
1               5               10              15

Asn Pro Glu Val Glu Ile Leu Asn Glu Glu Arg Ser Thr Gly Arg Leu
            20              25              30

Pro Leu Asp Ile Ser Leu Ser Leu Thr Arg Phe Leu Leu Ser Glu Phe
```

|     |     |     |     |     |     |     |     |     |     |     |     |     |     |     |
|---|---|---|---|---|---|---|---|---|---|---|---|---|---|---|
| Val | Pro | Gly | Val | Gly | Val | Ala | Phe | Gly | Leu | Phe | Asp | Leu | Ile | Trp | Gly |
|     | 50  |     |     |     | 55  |     |     |     |     | 60  |     |     |     |     |     |
| Phe | Ile | Thr | Pro | Ser | Asp | Trp | Ser | Leu | Phe | Leu | Leu | Gln | Ile | Glu | Gln |
| 65  |     |     |     |     | 70  |     |     |     | 75  |     |     |     |     |     | 80  |
| Leu | Ile | Glu | Gln | Arg | Ile | Glu | Thr | Leu | Glu | Arg | Asn | Arg | Ala | Ile | Thr |
|     |     |     |     | 85  |     |     |     |     | 90  |     |     |     |     | 95  |     |
| Thr | Leu | Arg | Gly | Leu | Ala | Asp | Ser | Tyr | Glu | Ile | Tyr | Ile | Glu | Ala | Leu |
|     |     |     | 100 |     |     |     |     | 105 |     |     |     |     | 110 |     |     |
| Arg | Glu | Trp | Glu | Ala | Asn | Pro | Asn | Asn | Ala | Gln | Leu | Arg | Glu | Asp | Val |
|     |     | 115 |     |     |     |     | 120 |     |     |     |     | 125 |     |     |     |
| Arg | Ile | Arg | Phe | Ala | Asn | Thr | Asp | Asp | Ala | Leu | Ile | Thr | Ala | Ile | Asn |
|     | 130 |     |     |     |     | 135 |     |     |     |     |     | 140 |     |     |     |
| Asn | Phe | Thr | Leu | Thr | Ser | Phe | Glu | Ile | Pro | Leu | Leu | Ser | Val | Tyr | Val |
| 145 |     |     |     |     | 150 |     |     |     |     | 155 |     |     |     |     | 160 |
| Gln | Ala | Ala | Asn | Leu | His | Leu | Ser | Leu | Leu | Arg | Asp | Ala | Val | Ser | Phe |
|     |     |     |     | 165 |     |     |     |     | 170 |     |     |     |     | 175 |     |
| Gly | Gln | Gly | Trp | Gly | Leu | Asp | Ile | Ala | Thr | Val | Asn | Asn | His | Tyr | Asn |
|     |     |     | 180 |     |     |     |     | 185 |     |     |     |     | 190 |     |     |
| Arg | Leu | Ile | Asn | Leu | Ile | His | Arg | Tyr | Thr | Lys | His | Cys | Leu | Asp | Thr |
|     |     | 195 |     |     |     |     | 200 |     |     |     |     | 205 |     |     |     |
| Tyr | Asn | Gln | Gly | Leu | Glu | Asn | Leu | Arg | Gly | Thr | Asn | Thr | Arg | Gln | Trp |
|     | 210 |     |     |     |     | 215 |     |     |     |     | 220 |     |     |     |     |
| Ala | Arg | Phe | Asn | Gln | Phe | Arg | Arg | Asp | Leu | Thr | Leu | Thr | Val | Leu | Asp |
| 225 |     |     |     |     | 230 |     |     |     |     | 235 |     |     |     |     | 240 |
| Ile | Val | Ala | Leu | Phe | Pro | Asn | Tyr | Asp | Val | Arg | Thr | Tyr | Pro | Ile | Gln |
|     |     |     |     | 245 |     |     |     |     | 250 |     |     |     |     | 255 |     |
| Thr | Ser | Ser | Gln | Leu | Thr | Arg | Glu | Ile | Tyr | Thr | Ser | Ser | Val | Ile | Glu |
|     |     |     | 260 |     |     |     |     | 265 |     |     |     |     | 270 |     |     |
| Asp | Ser | Pro | Val | Ser | Ala | Asn | Ile | Pro | Asn | Gly | Phe | Asn | Arg | Ala | Glu |
|     |     | 275 |     |     |     |     | 280 |     |     |     |     | 285 |     |     |     |
| Phe | Gly | Val | Arg | Pro | Pro | His | Leu | Met | Asp | Phe | Met | Asn | Ser | Leu | Phe |
|     | 290 |     |     |     |     | 295 |     |     |     |     | 300 |     |     |     |     |
| Val | Thr | Ala | Glu | Thr | Val | Arg | Ser | Gln | Thr | Val | Trp | Gly | Gly | His | Leu |
| 305 |     |     |     |     | 310 |     |     |     |     | 315 |     |     |     |     | 320 |
| Val | Ser | Ser | Arg | Asn | Thr | Ala | Gly | Asn | Arg | Ile | Asn | Phe | Pro | Ser | Tyr |
|     |     |     |     | 325 |     |     |     |     | 330 |     |     |     |     | 335 |     |
| Gly | Val | Phe | Asn | Pro | Gly | Gly | Ala | Ile | Trp | Ile | Ala | Asp | Glu | Asp | Pro |
|     |     |     | 340 |     |     |     |     | 345 |     |     |     |     | 350 |     |     |
| Arg | Pro | Phe | Tyr | Arg | Thr | Leu | Ser | Asp | Pro | Val | Phe | Val | Arg | Gly | Gly |
|     |     | 355 |     |     |     |     | 360 |     |     |     |     | 365 |     |     |     |
| Phe | Gly | Asn | Pro | His | Tyr | Val | Leu | Gly | Leu | Arg | Gly | Val | Ala | Phe | Gln |
|     | 370 |     |     |     |     | 375 |     |     |     |     | 380 |     |     |     |     |
| Gln | Thr | Gly | Thr | Asn | His | Thr | Arg | Thr | Phe | Arg | Asn | Ser | Gly | Thr | Ile |
| 385 |     |     |     |     | 390 |     |     |     |     | 395 |     |     |     |     | 400 |
| Asp | Ser | Leu | Asp | Glu | Ile | Pro | Pro | Gln | Asp | Asn | Ser | Gly | Ala | Pro | Trp |
|     |     |     |     | 405 |     |     |     |     | 410 |     |     |     |     | 415 |     |
| Asn | Asp | Tyr | Ser | His | Val | Leu | Asn | His | Val | Thr | Phe | Val | Arg | Trp | Pro |
|     |     |     | 420 |     |     |     |     | 425 |     |     |     |     | 430 |     |     |
| Gly | Glu | Ile | Ser | Gly | Ser | Asp | Ser | Trp | Arg | Ala | Pro | Met | Phe | Ser | Trp |
|     |     | 435 |     |     |     |     | 440 |     |     |     |     | 445 |     |     |     |
| Thr | His | Arg | Ser | Ala | Thr | Pro | Thr | Asn | Thr | Ile | Asp | Pro | Glu | Arg | Ile |
|     | 450 |     |     |     |     | 455 |     |     |     |     | 460 |     |     |     |     |
| Thr | Gln | Ile | Pro | Leu | Val | Lys | Ala | His | Thr | Leu | Gln | Ser | Gly | Thr | Thr |
| 465 |     |     |     |     | 470 |     |     |     |     | 475 |     |     |     |     | 480 |

| | | | | | | | | | | | | | | |
|---|---|---|---|---|---|---|---|---|---|---|---|---|---|---|
| Val | Val | Arg | Gly | Pro<br>485 | Gly | Phe | Thr | Gly<br>490 | Gly | Asp | Ile | Leu | Arg<br>495 | Thr |
| Ser | Gly | Gly | Pro<br>500 | Phe | Ala | Tyr | Thr | Ile<br>505 | Val | Asn | Ile | Asn<br>510 | Gly | Gln | Leu |
| Pro | Gln | Arg<br>515 | Tyr | Arg | Ala | Arg | Ile<br>520 | Arg | Tyr | Ala | Ser | Thr<br>525 | Thr | Asn | Leu |
| Arg | Ile<br>530 | Tyr | Val | Thr | Val | Ala<br>535 | Gly | Glu | Arg | Ile | Phe<br>540 | Ala | Gly | Gln | Phe |
| Asn<br>545 | Lys | Thr | Met | Asp | Thr<br>550 | Gly | Asp | Pro | Leu | Thr<br>555 | Phe | Gln | Ser | Phe | Ser<br>560 |
| Tyr | Ala | Thr | Ile | Asn<br>565 | Thr | Ala | Phe | Thr | Phe<br>570 | Pro | Met | Ser | Gln<br>575 | Ser | Ser |
| Phe | Thr | Val | Gly<br>580 | Ala | Asp | Thr | Phe | Ser<br>585 | Ser | Gly | Asn | Glu | Val<br>590 | Tyr | Ile |
| Asp | Arg | Phe<br>595 | Glu | Leu | Ile | Pro | Val<br>600 | Thr | Ala | Thr | Phe | Glu<br>605 | Ala | Glu | Tyr |
| Asp | Leu<br>610 | Glu | Arg | Ala | Gln | Lys<br>615 | Ala | Val | Asn | Ala | Leu<br>620 | Phe | Thr | Ser | Ile |
| Asn<br>625 | Gln | Ile | Gly | Ile | Lys<br>630 | Thr | Asp | Val | Thr | Asp<br>635 | Tyr | His | Ile | Asp<br>640 | Gln |
| Val | Ser | Asn | Leu | Val<br>645 | Asp | Cys | Leu | Ser | Asp<br>650 | Glu | Phe | Cys | Leu | Asp<br>655 | Glu |
| Lys | Arg | Glu | Leu<br>660 | Ser | Glu | Lys | Val | Lys<br>665 | His | Ala | Lys | Arg | Leu<br>670 | Ser | Asp |
| Glu | Arg | Asn<br>675 | Leu | Leu | Gln | Asp | Pro<br>680 | Asn | Phe | Lys | Gly | Ile<br>685 | Asn | Arg | Gln |
| Leu | Asp<br>690 | Arg | Gly | Trp | Arg | Gly<br>695 | Ser | Thr | Asp | Ile | Thr<br>700 | Ile | Gln | Arg | Gly |
| Asp<br>705 | Asp | Val | Phe | Lys | Glu<br>710 | Asn | Tyr | Val | Thr | Leu<br>715 | Pro | Gly | Thr | Phe | Asp<br>720 |
| Glu | Cys | Tyr | Pro | Thr<br>725 | Tyr | Leu | Tyr | Gln | Lys<br>730 | Ile | Asp | Glu | Ser | Lys<br>735 | Leu |
| Lys | Pro | Tyr | Thr<br>740 | Arg | Tyr | Gln | Leu | Arg<br>745 | Gly | Tyr | Ile | Glu | Asp<br>750 | Ser | Gln |
| Asp | Leu | Glu<br>755 | Ile | Tyr | Leu | Ile | Arg<br>760 | Tyr | Asn | Ala | Lys | His<br>765 | Glu | Thr | Val |
| Asn | Val<br>770 | Leu | Gly | Thr | Gly | Ser<br>775 | Leu | Trp | Pro | Leu | Ser<br>780 | Val | Gln | Ser | Pro |
| Ile<br>785 | Arg | Lys | Cys | Gly | Glu<br>790 | Pro | Asn | Arg | Cys | Ala<br>795 | Pro | His | Leu | Glu | Trp<br>800 |
| Asn | Pro | Asp | Leu | Asp<br>805 | Cys | Ser | Cys | Arg | Asp<br>810 | Gly | Glu | Lys | Cys | Ala<br>815 | His |
| His | Ser | His | His | Phe<br>820 | Ser | Leu | Asp | Ile<br>825 | Asp | Val | Gly | Cys | Thr<br>830 | Asp | Leu |
| Asn | Glu | Asp<br>835 | Leu | Asp | Val | Trp | Val<br>840 | Ile | Phe | Lys | Ile | Lys<br>845 | Thr | Gln | Asp |
| Gly | His<br>850 | Ala | Arg | Leu | Gly | Asn<br>855 | Leu | Glu | Phe | Leu | Glu<br>860 | Glu | Lys | Pro | Leu |
| Val<br>865 | Gly | Glu | Ala | Leu | Ala<br>870 | Arg | Val | Lys | Arg | Ala<br>875 | Glu | Lys | Lys | Trp | Arg<br>880 |
| Asp | Lys | Arg | Glu | Lys<br>885 | Leu | Glu | Leu | Glu | Thr<br>890 | Asn | Ile | Val | Tyr | Lys<br>895 | Glu |
| Ala | Lys | Glu | Ser<br>900 | Val | Asp | Ala | Leu | Phe<br>905 | Val | Asn | Ser | Gln | Tyr<br>910 | Asp | Gln |
| Leu | Gln | Ala | Asp | Thr<br>915 | Asn | Ile | Ala | Met<br>920 | Ile | His | Ala | Ala | Asp<br>925 | Lys | Arg |

Val His Arg Ile Arg Glu Ala Tyr Leu Pro Glu Leu Ser Val Ile Pro
930                     935             940

Gly Val Asn Val Asp Ile Phe Glu Glu Leu Lys Gly Arg Ile Phe Thr
945                 950             955                     960

Ala Phe Phe Leu Tyr Asp Ala Arg Asn Val Ile Lys Asn Gly Asp Phe
            965                 970                 975

Asn Asn Gly Leu Ser Cys Trp Asn Val Lys Gly His Val Asp Val Glu
            980                 985             990

Glu Gln Asn Asn His Arg Ser Val Leu Val Val Pro Glu Trp Glu Ala
        995             1000            1005

Glu Val Ser Gln Glu Val Arg Val Cys Pro Gly Arg Gly Tyr Ile Leu
    1010            1015            1020

Arg Val Thr Ala Tyr Lys Glu Gly Tyr Gly Glu Gly Cys Val Thr Ile
1025            1030            1035                    1040

His Glu Ile Glu Asn Asn Thr Asp Glu Leu Lys Phe Ser Asn Cys Val
            1045            1050            1055

Glu Glu Glu Val Tyr Pro Asn Asn Thr Val Thr Cys Asn Asp Tyr Thr
            1060            1065            1070

Ala Asn Gln Glu Glu Tyr Gly Gly Ala Tyr Thr Ser Arg Asn Arg Gly
            1075            1080            1085

Tyr Asp Glu Thr Tyr Gly Ser Asn Ser Ser Val Pro Ala Asp Tyr Ala
            1090            1095            1100

Ser Val Tyr Glu Glu Lys Ser Tyr Thr Asp Gly Arg Arg Asp Asn Pro
1105            1110            1115                    1120

Cys Glu Ser Asn Arg Gly Tyr Gly Asp Tyr Thr Pro Leu Pro Ala Gly
            1125            1130            1135

Tyr Val Thr Lys Glu Leu Glu Tyr Phe Pro Glu Thr Asp Lys Val Trp
            1140            1145            1150

Ile Glu Ile Gly Glu Thr Glu Gly Thr Phe Ile Val Asp Ser Val Glu
            1155            1160            1165

Leu Leu Leu Met Glu Glu
            1170

( 2 ) INFORMATION FOR SEQ ID NO:33:

( i ) SEQUENCE CHARACTERISTICS:
( A ) LENGTH: 1155 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:33:

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
            85                  90                  95

Ile Ser Arg Leu Glu Gly Leu Ser Asn Leu Tyr Gln Ile Tyr Ala Glu
            100                 105                 110

| | | | | | | | | | | | | | | |
|---|---|---|---|---|---|---|---|---|---|---|---|---|---|---|
| Ser | Phe | Arg | Glu | Trp | Glu | Ala | Asp | Pro | Thr | Asn | Pro | Ala | Leu | Arg | Glu |
| | | 115 | | | | 120 | | | | | 125 | | | | |
| Glu | Met | Arg | Ile | Gln | Phe | Asn | Asp | Met | Asn | Ser | Ala | Leu | Thr | Thr | Ala |
| | | 130 | | | | 135 | | | | | 140 | | | | |
| Ile | Pro | Leu | Phe | Ala | Val | Gln | Asn | Tyr | Gln | Val | Pro | Leu | Leu | Ser | Val |
| 145 | | | | | 150 | | | | | 155 | | | | | 160 |
| Tyr | Val | Gln | Ala | Ala | Asn | Leu | His | Leu | Ser | Val | Leu | Arg | Asp | Val | Ser |
| | | | | 165 | | | | 170 | | | | | | 175 | |
| Val | Phe | Gly | Gln | Arg | Trp | Gly | Phe | Asp | Ala | Ala | Thr | Ile | Asn | Ser | Arg |
| | | | 180 | | | | | 185 | | | | | 190 | | |
| Tyr | Asn | Asp | Leu | Thr | Arg | Leu | Ile | Gly | Asn | Tyr | Thr | Asp | His | Ala | Val |
| | | 195 | | | | | 200 | | | | | 205 | | | |
| Arg | Trp | Tyr | Asn | Thr | Gly | Leu | Glu | Arg | Val | Trp | Gly | Pro | Asp | Ser | Arg |
| 210 | | | | | 215 | | | | | | 220 | | | | |
| Asp | Trp | Ile | Arg | Tyr | Asn | Gln | Phe | Arg | Arg | Glu | Leu | Thr | Leu | Thr | Val |
| 225 | | | | | 230 | | | | | 235 | | | | | 240 |
| Leu | Asp | Ile | Val | Ser | Leu | Phe | Pro | Asn | Tyr | Asp | Ser | Arg | Thr | Tyr | Pro |
| | | | | 245 | | | | | 250 | | | | | 255 | |
| Ile | Arg | Thr | Val | Ser | Gln | Leu | Thr | Arg | Glu | Ile | Tyr | Thr | Asn | Pro | Val |
| | | | 260 | | | | | 265 | | | | | 270 | | |
| Leu | Glu | Asn | Phe | Asp | Gly | Ser | Phe | Arg | Gly | Ser | Ala | Gln | Gly | Ile | Glu |
| | | 275 | | | | | 280 | | | | | 285 | | | |
| Gly | Ser | Ile | Arg | Ser | Pro | His | Leu | Met | Asp | Ile | Leu | Asn | Ser | Ile | Thr |
| | 290 | | | | | 295 | | | | | 300 | | | | |
| Ile | Tyr | Thr | Asp | Ala | His | Arg | Gly | Glu | Tyr | Tyr | Trp | Ser | Gly | His | Gln |
| 305 | | | | | 310 | | | | | 315 | | | | | 320 |
| Ile | Met | Ala | Ser | Pro | Val | Gly | Phe | Ser | Gly | Pro | Glu | Phe | Thr | Phe | Pro |
| | | | | 325 | | | | | 330 | | | | | 335 | |
| Leu | Tyr | Gly | Thr | Met | Gly | Asn | Ala | Ala | Pro | Gln | Gln | Arg | Ile | Val | Ala |
| | | | 340 | | | | | 345 | | | | | 350 | | |
| Gln | Leu | Gly | Gln | Gly | Val | Tyr | Arg | Thr | Leu | Ser | Ser | Thr | Leu | Tyr | Arg |
| | | 355 | | | | | 360 | | | | | 365 | | | |
| Arg | Pro | Phe | Asn | Ile | Gly | Ile | Asn | Asn | Gln | Gln | Leu | Ser | Val | Leu | Asp |
| | 370 | | | | | 375 | | | | | 380 | | | | |
| Gly | Thr | Glu | Phe | Ala | Tyr | Gly | Thr | Ser | Ser | Asn | Leu | Pro | Ser | Ala | Val |
| 385 | | | | | 390 | | | | | 395 | | | | | 400 |
| Tyr | Arg | Lys | Ser | Gly | Thr | Val | Asp | Ser | Leu | Asp | Glu | Ile | Pro | Pro | Gln |
| | | | | 405 | | | | | 410 | | | | | 415 | |
| Asn | Asn | Asn | Val | Pro | Pro | Arg | Gln | Gly | Phe | Ser | His | Arg | Leu | Ser | His |
| | | | | 420 | | | | | 425 | | | | | 430 | |
| Val | Ser | Met | Phe | Arg | Ser | Gly | Phe | Ser | Asn | Ser | Ser | Val | Ser | Ile | Ile |
| | | | 435 | | | | | 440 | | | | | 445 | | |
| Arg | Ala | Pro | Met | Phe | Ser | Trp | Ile | His | Arg | Ser | Ala | Glu | Phe | Asn | Asn |
| | 450 | | | | | 455 | | | | | 460 | | | | |
| Ile | Ile | Pro | Ser | Ser | Gln | Ile | Thr | Gln | Ile | Pro | Leu | Thr | Lys | Ser | Thr |
| 465 | | | | | 470 | | | | | 475 | | | | | 480 |
| Asn | Leu | Gly | Ser | Gly | Thr | Ser | Val | Val | Lys | Gly | Pro | Gly | Phe | Thr | Gly |
| | | | | 485 | | | | | 490 | | | | | 495 | |
| Gly | Asp | Ile | Leu | Arg | Arg | Thr | Ser | Pro | Gly | Gln | Ile | Ser | Thr | Leu | Arg |
| | | | | 500 | | | | | 505 | | | | | 510 | |
| Val | Asn | Ile | Thr | Ala | Pro | Leu | Ser | Gln | Arg | Tyr | Arg | Val | Arg | Ile | Arg |
| | | | 515 | | | | | 520 | | | | | 525 | | |
| Tyr | Ala | Ser | Thr | Thr | Asn | Leu | Gln | Phe | His | Thr | Ser | Ile | Asp | Gly | Arg |
| | | 530 | | | | | 535 | | | | | 540 | | | |
| Pro | Ile | Asn | Gln | Gly | Asn | Phe | Ser | Ala | Thr | Met | Ser | Ser | Gly | Ser | Asn |
| 545 | | | | | 550 | | | | | 555 | | | | | 560 |

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
            595                 600                 605

Val Thr Phe Glu Ala Glu Tyr Asp Leu Glu Arg Ala Gln Lys Ala Val
        610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
            660                 665                 670

His Ala Lys Arg Leu Ser Asp Glu Arg Asn Leu Leu Gln Asp Pro Asn
            675                 680                 685

Phe Arg Gly Ile Asn Arg Gln Leu Asp Arg Gly Trp Arg Gly Ser Thr
            690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
            740                 745                 750

Gly Tyr Ile Glu Asp Ser Gln Asp Leu Glu Ile Tyr Leu Ile Arg Tyr
            755                 760                 765

Asn Ala Lys His Glu Thr Val Asn Val Pro Gly Thr Gly Ser Leu Trp
770                 775                 780

Pro Leu Ser Ala Pro Ser Pro Ile Gly Lys Cys Ala His His Ser His
785                 790                 795                 800

His Phe Ser Leu Asp Ile Asp Val Gly Cys Thr Asp Leu Asn Glu Asp
            805                 810                 815

Leu Gly Val Trp Val Ile Phe Lys Ile Lys Thr Gln Asp Gly His Ala
            820                 825                 830

Arg Leu Gly Asn Leu Glu Phe Leu Glu Glu Lys Pro Leu Val Gly Glu
            835                 840                 845

Ala Leu Ala Arg Val Lys Arg Ala Glu Lys Lys Trp Arg Asp Lys Arg
        850                 855                 860

Glu Lys Leu Glu Trp Glu Thr Asn Ile Val Tyr Lys Glu Ala Lys Glu
865                 870                 875                 880

Ser Val Asp Ala Leu Phe Val Asn Ser Gln Tyr Asp Arg Leu Gln Ala
                885                 890                 895

Asp Thr Asn Ile Ala Met Ile His Ala Ala Asp Lys Arg Val His Ser
            900                 905                 910

Ile Arg Glu Ala Tyr Leu Pro Glu Leu Ser Val Ile Pro Gly Val Asn
            915                 920                 925

Ala Ala Ile Phe Glu Glu Leu Glu Gly Arg Ile Phe Thr Ala Phe Ser
        930                 935                 940

Leu Tyr Asp Ala Arg Asn Val Ile Lys Asn Gly Asp Phe Asn Asn Gly
945                 950                 955                 960

Leu Ser Cys Trp Asn Val Lys Gly His Val Asp Val Glu Glu Gln Asn
                965                 970                 975

Asn His Arg Ser Val Leu Val Val Pro Glu Trp Glu Ala Glu Val Ser
            980                 985                 990

Gln Glu Val Arg Val Cys Pro Gly Arg Gly Tyr Ile Leu Arg Val Thr

```
                           995                      1000                      1005
Ala  Tyr  Lys  Glu  Gly  Tyr  Gly  Glu  Gly  Cys  Val  Thr  Ile  His  Glu  Ile
              1010                      1015                      1020
Glu  Asn  Asn  Thr  Asp  Glu  Leu  Lys  Phe  Ser  Asn  Cys  Val  Glu  Glu  Glu
1025                     1030                      1035                      1040
Val  Tyr  Pro  Asn  Asn  Thr  Val  Thr  Cys  Asn  Asp  Tyr  Thr  Ala  Thr  Gln
              1045                      1050                      1055
Glu  Glu  Tyr  Glu  Gly  Thr  Tyr  Thr  Ser  Arg  Asn  Arg  Gly  Tyr  Asp  Gly
              1060                      1065                      1070
Ala  Tyr  Glu  Ser  Asn  Ser  Ser  Val  Pro  Ala  Asp  Tyr  Ala  Ser  Ala  Tyr
              1075                      1080                      1085
Glu  Glu  Lys  Ala  Tyr  Thr  Asp  Gly  Arg  Arg  Asp  Asn  Pro  Cys  Glu  Ser
              1090                      1095                      1100
Asn  Arg  Gly  Tyr  Gly  Asp  Tyr  Thr  Pro  Leu  Pro  Ala  Gly  Tyr  Val  Thr
1105                     1110                      1115                      1120
Lys  Glu  Leu  Glu  Tyr  Phe  Pro  Glu  Thr  Asp  Lys  Val  Trp  Ile  Glu  Ile
              1125                      1130                      1135
Gly  Glu  Thr  Glu  Gly  Thr  Phe  Ile  Val  Asp  Ser  Val  Glu  Leu  Leu  Leu
              1140                      1145                      1150
Met  Glu  Glu
              1155
```

( 2 ) INFORMATION FOR SEQ ID NO:34:

( i ) SEQUENCE CHARACTERISTICS:
        ( A ) LENGTH: 1182 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:34:

```
Met  Asp  Asn  Asn  Pro  Asn  Ile  Asn  Glu  Cys  Ile  Pro  Tyr  Asn  Cys  Leu
1                   5                        10                       15
Ser  Asn  Pro  Glu  Val  Glu  Val  Leu  Gly  Gly  Glu  Arg  Ile  Glu  Thr  Gly
              20                       25                       30
Tyr  Thr  Pro  Ile  Asp  Ile  Ser  Leu  Ser  Leu  Thr  Gln  Phe  Leu  Leu  Ser
              35                       40                       45
Glu  Phe  Val  Pro  Gly  Ala  Gly  Phe  Val  Leu  Gly  Leu  Val  Asp  Ile  Ile
     50                       55                       60
Trp  Gly  Ile  Phe  Gly  Pro  Ser  Gln  Trp  Asp  Ala  Phe  Leu  Val  Gln  Ile
65                       70                       75                       80
Glu  Gln  Leu  Ile  Asn  Gln  Arg  Ile  Glu  Glu  Phe  Ala  Arg  Asn  Gln  Ala
                    85                       90                       95
Ile  Ser  Arg  Leu  Glu  Gly  Leu  Ser  Asn  Leu  Tyr  Gln  Ile  Tyr  Ala  Glu
              100                      105                      110
Ser  Phe  Arg  Glu  Trp  Glu  Ala  Asp  Pro  Thr  Asn  Pro  Ala  Leu  Arg  Glu
              115                      120                      125
Glu  Met  Arg  Ile  Gln  Phe  Asn  Asp  Met  Asn  Ser  Ala  Leu  Thr  Thr  Ala
              130                      135                      140
Ile  Pro  Leu  Phe  Ala  Val  Gln  Asn  Tyr  Gln  Val  Pro  Leu  Leu  Ser  Val
145                      150                      155                      160
Tyr  Val  Gln  Ala  Ala  Asn  Leu  His  Leu  Ser  Val  Leu  Arg  Asp  Val  Ser
                    165                      170                      175
Val  Phe  Gly  Gln  Arg  Trp  Gly  Phe  Asp  Ala  Ala  Thr  Ile  Asn  Ser  Arg
              180                      185                      190
Tyr  Asn  Asp  Leu  Thr  Arg  Leu  Ile  Gly  Asn  Tyr  Thr  Asp  Tyr  Ala  Val
              195                      200                      205
```

```
Arg Trp Tyr Asn Thr Gly Leu Glu Arg Val Trp Gly Pro Asp Ser Arg
210                 215                 220
Asp Trp Val Arg Tyr Asn Gln Phe Arg Arg Glu Leu Thr Leu Thr Val
225                 230                 235                 240
Leu Asp Ile Val Ala Leu Phe Pro Asn Tyr Asp Ser Arg Arg Tyr Pro
                    245                 250                 255
Ile Arg Thr Val Ser Gln Leu Thr Arg Glu Ile Tyr Thr Asn Pro Val
                260                 265                 270
Leu Glu Asn Phe Asp Gly Ser Phe Arg Gly Ser Ala Gln Gly Ile Glu
            275                 280                 285
Arg Ser Ile Arg Ser Pro His Leu Met Asp Ile Leu Asn Ser Ile Thr
290                 295                 300
Ile Tyr Thr Asp Ala His Arg Gly Tyr Tyr Tyr Trp Ser Gly His Gln
305                 310                 315                 320
Ile Met Ala Ser Pro Val Gly Phe Ser Gly Pro Glu Phe Thr Phe Pro
                325                 330                 335
Leu Tyr Gly Thr Met Gly Asn Ala Ala Pro Gln Gln Arg Ile Val Ala
            340                 345                 350
Gln Leu Gly Gln Gly Val Tyr Arg Thr Leu Ser Ser Thr Leu Tyr Arg
            355                 360                 365
Arg Pro Phe Asn Ile Gly Ile Asn Asn Gln Gln Leu Ser Val Leu Asp
370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Glu Ile Pro Pro Gln
                405                 410                 415
Asn Asn Asn Val Pro Pro Arg Gln Gly Phe Ser His Arg Leu Ser His
            420                 425                 430
Val Ser Met Phe Arg Ser Gly Phe Ser Asn Ser Ser Val Ser Ile Ile
            435                 440                 445
Arg Ala Pro Met Phe Ser Trp Ile His Arg Ser Ala Glu Phe Asn Asn
450                 455                 460
Ile Ile Ala Ser Asp Ser Ile Thr Gln Ile Pro Ala Val Lys Gly Asn
465                 470                 475                 480
Phe Leu Phe Asn Gly Ser Val Ile Ser Gly Pro Gly Phe Thr Gly Gly
                485                 490                 495
Asp Leu Val Arg Leu Asn Ser Ser Gly Asn Asn Ile Gln Asn Arg Gly
                500                 505                 510
Tyr Ile Glu Val Pro Ile His Phe Pro Ser Thr Ser Thr Arg Tyr Arg
            515                 520                 525
Val Arg Val Arg Tyr Ala Ser Val Thr Pro Ile His Leu Asn Val Asn
            530                 535                 540
Trp Gly Asn Ser Ser Ile Phe Ser Asn Thr Val Pro Ala Thr Ala Thr
545                 550                 555                 560
Ser Leu Asp Asn Leu Gln Ser Ser Asp Phe Gly Tyr Phe Glu Ser Ala
                565                 570                 575
Asn Ala Phe Thr Ser Ser Leu Gly Asn Ile Val Gly Val Arg Asn Phe
            580                 585                 590
Ser Gly Thr Ala Gly Val Ile Ile Asp Arg Phe Glu Phe Ile Pro Val
            595                 600                 605
Thr Ala Thr Leu Glu Ala Glu Tyr Asn Leu Glu Arg Ala Gln Lys Ala
        610                 615                 620
Val Asn Ala Leu Phe Thr Ser Thr Asn Gln Leu Gly Leu Lys Thr Asn
625                 630                 635                 640
Val Thr Asp Tyr His Ile Asp Gln Val Ser Asn Leu Val Thr Tyr Leu
```

| | | | | 645 | | | | 650 | | | | 655 | | |
|---|---|---|---|---|---|---|---|---|---|---|---|---|---|---|
| Ser | Asp | Glu | Phe | Cys | Leu | Asp | Glu | Lys | Arg | Glu | Leu | Ser | Glu | Lys | Val |
| | | | 660 | | | | 665 | | | | 670 | | | | |
| Lys | His | Ala | Lys | Arg | Leu | Ser | Asp | Glu | Arg | Asn | Leu | Leu | Gln | Asp | Ser |
| | | 675 | | | | 680 | | | | 685 | | | | | |
| Asn | Phe | Lys | Asp | Ile | Asn | Arg | Gln | Pro | Glu | Arg | Gly | Trp | Gly | Gly | Ser |
| 690 | | | | | 695 | | | | 700 | | | | | | |
| Thr | Gly | Ile | Thr | Ile | Gln | Gly | Gly | Asp | Asp | Val | Phe | Lys | Glu | Asn | Tyr |
| 705 | | | | 710 | | | | 715 | | | | | | | 720 |
| Val | Thr | Leu | Ser | Gly | Thr | Phe | Asp | Glu | Cys | Tyr | Pro | Thr | Tyr | Leu | Tyr |
| | | | | 725 | | | | 730 | | | | | 735 | | |
| Gln | Lys | Ile | Asp | Glu | Ser | Lys | Leu | Lys | Ala | Phe | Thr | Arg | Tyr | Gln | Leu |
| | | | 740 | | | | 745 | | | | | 750 | | | |
| Arg | Gly | Tyr | Ile | Glu | Asp | Ser | Gln | Asp | Leu | Glu | Ile | Tyr | Leu | Ile | Arg |
| | | 755 | | | | 760 | | | | 765 | | | | | |
| Tyr | Asn | Ala | Lys | His | Glu | Thr | Val | Asn | Val | Pro | Gly | Thr | Gly | Ser | Leu |
| | 770 | | | | 775 | | | | 780 | | | | | | |
| Trp | Pro | Leu | Ser | Ala | Gln | Ser | Pro | Ile | Gly | Lys | Cys | Gly | Glu | Pro | Asn |
| 785 | | | | 790 | | | | 795 | | | | | | | 800 |
| Arg | Cys | Ala | Pro | His | Leu | Glu | Trp | Asn | Pro | Asp | Leu | Asp | Cys | Ser | Cys |
| | | | 805 | | | | 810 | | | | | 815 | | | |
| Arg | Asp | Gly | Glu | Lys | Cys | Ala | His | His | Ser | His | His | Phe | Ser | Leu | Asp |
| | | 820 | | | | 825 | | | | 830 | | | | | |
| Ile | Asp | Val | Gly | Cys | Thr | Asp | Leu | Asn | Glu | Asp | Leu | Gly | Val | Trp | Val |
| | 835 | | | | 840 | | | | 845 | | | | | | |
| Ile | Phe | Lys | Ile | Lys | Thr | Gln | Asp | Gly | His | Ala | Leu | Arg | Leu | Gly | Asn | Leu |
| 850 | | | | 855 | | | | 860 | | | | | | | |
| Glu | Phe | Leu | Glu | Glu | Lys | Pro | Leu | Val | Gly | Glu | Ala | Leu | Ala | Arg | Val |
| 865 | | | | 870 | | | | 875 | | | | | | | 880 |
| Lys | Arg | Ala | Glu | Lys | Lys | Trp | Arg | Asp | Lys | Arg | Glu | Lys | Leu | Glu | Trp |
| | | | 885 | | | | 890 | | | | | 895 | | | |
| Glu | Thr | Asn | Ile | Val | Tyr | Lys | Glu | Ala | Lys | Glu | Ser | Val | Asp | Ala | Leu |
| | | | 900 | | | | 905 | | | | | 910 | | | |
| Phe | Val | Asn | Ser | Gln | Tyr | Asp | Gln | Leu | Gln | Ala | Asp | Thr | Asn | Ile | Ala |
| | | 915 | | | | 920 | | | | 925 | | | | | |
| Met | Ile | His | Ala | Ala | Asp | Lys | Arg | Val | His | Ser | Ile | Arg | Glu | Ala | Tyr |
| | 930 | | | | 935 | | | | 940 | | | | | | |
| Leu | Pro | Glu | Leu | Ser | Val | Ile | Pro | Gly | Val | Asn | Ala | Ala | Ile | Phe | Glu |
| 945 | | | | 950 | | | | 955 | | | | | | | 960 |
| Glu | Leu | Glu | Gly | Arg | Ile | Phe | Thr | Ala | Phe | Ser | Leu | Tyr | Asp | Ala | Arg |
| | | | 965 | | | | 970 | | | | | 975 | | | |
| Asn | Val | Ile | Lys | Asn | Gly | Asp | Phe | Asn | Asn | Gly | Leu | Ser | Cys | Trp | Asn |
| | | | 980 | | | | 985 | | | | | 990 | | | |
| Val | Lys | Gly | His | Val | Asp | Val | Glu | Glu | Gln | Asn | Asn | His | Arg | Ser | Val |
| | | 995 | | | | 1000 | | | | 1005 | | | | | |
| Leu | Val | Val | Pro | Glu | Trp | Glu | Ala | Glu | Val | Ser | Gln | Glu | Val | Arg | Val |
| | 1010 | | | | 1015 | | | | 1020 | | | | | | |
| Cys | Pro | Gly | Arg | Gly | Tyr | Ile | Leu | Arg | Val | Thr | Ala | Tyr | Lys | Glu | Gly |
| 1025 | | | | 1030 | | | | 1035 | | | | | | | 1040 |
| Tyr | Gly | Glu | Gly | Cys | Val | Thr | Ile | His | Glu | Ile | Glu | Asn | Asn | Thr | Asp |
| | | | 1045 | | | | 1050 | | | | | 1055 | | | |
| Glu | Leu | Lys | Phe | Ser | Asn | Cys | Val | Glu | Glu | Glu | Val | Tyr | Pro | Asn | Asn |
| | | | 1060 | | | | 1065 | | | | | 1070 | | | |
| Thr | Val | Thr | Cys | Asn | Asp | Tyr | Thr | Ala | Thr | Gln | Glu | Glu | Tyr | Glu | Gly |
| | | 1075 | | | | 1080 | | | | 1085 | | | | | |

| | | | | | | | | | | | | | | |
|---|---|---|---|---|---|---|---|---|---|---|---|---|---|---|
|Thr|Tyr 1090|Thr|Ser|Arg|Asn|Arg 1095|Gly|Tyr|Asp|Gly|Ala 1100|Tyr|Glu|Ser|Asn|
|Ser 1105|Ser|Val|Pro|Ala|Asp 1110|Tyr|Ala|Ser|Ala|Glu 1115|Glu|Lys|Ala|Tyr 1120|
|Thr|Asp|Gly|Arg|Arg 1125|Asp|Asn|Pro|Cys|Glu 1130|Ser|Asn|Arg|Gly|Tyr 1135|Gly|
|Asp|Tyr|Thr|Pro 1140|Leu|Pro|Ala|Gly|Tyr 1145|Val|Thr|Lys|Glu|Leu 1150|Glu|Tyr|
|Phe|Pro|Glu|Thr 1155|Asp|Lys|Val|Trp 1160|Ile|Glu|Ile|Gly|Glu 1165|Thr|Glu|Gly|
|Thr|Phe 1170|Ile|Val|Asp|Ser|Val 1175|Glu|Leu|Leu|Leu|Met 1180|Glu|Glu|